US007750137B2

(12) United States Patent
Briskin

(10) Patent No.: US 7,750,137 B2
(45) Date of Patent: Jul. 6, 2010

(54) MUCOSAL VASCULAR ADDRESSINS

(75) Inventor: Michael J. Briskin, Lexington, MA (US)

(73) Assignee: Millennium Pharmaceuticals, Inc., Cambridge, MA (US)

(*) Notice: Subject to any disclaimer, the term of this patent is extended or adjusted under 35 U.S.C. 154(b) by 723 days.

(21) Appl. No.: 08/523,004

(22) Filed: Sep. 1, 1995

(65) Prior Publication Data

US 2004/0023373 A1 Feb. 5, 2004

(51) Int. Cl.
*C12N 15/12* (2006.01)
*C12N 5/07* (2006.01)
*C12N 1/21* (2006.01)

(52) U.S. Cl. .................... 536/23.5; 435/325; 435/252.3

(58) Field of Classification Search ................ 536/23.1, 536/23.4, 23.5; 935/9, 11, 22; 435/320, 435/325

See application file for complete search history.

(56) References Cited

U.S. PATENT DOCUMENTS

| 4,699,880 | A | 10/1987 | Goldstein |
| 5,223,392 | A | 6/1993 | Cohen |
| 5,403,919 | A | 4/1995 | Butcher ................. 530/388.22 |
| 5,538,724 | A | 7/1996 | Butcher et al. ........... 424/152.1 |
| 5,599,676 | A | 2/1997 | Vonderheide et al. ........ 435/7.2 |

FOREIGN PATENT DOCUMENTS

| EP | 0 303 463 B1 | 11/1994 |
| WO | 90/07321 | 7/1990 |
| WO | 93/15764 | 8/1993 |
| WO | 93/23526 | 11/1993 |
| WO | 94/13312 | 6/1994 |
| WO | 94/16094 | 7/1994 |
| WO | WO95/19790 | 7/1995 |

OTHER PUBLICATIONS

Ngo et al., Chapter 14, from "The Protein Folding Problem and Tertiary structure Prediction", Eds. Merz et al., Birkhauser Boston 1994, p. 491-495.*
Ringler, D.J. et al., "Cellular Localization of Simian Immuno-deficiency Virus in Lymphoid Tissues I. Immunohistochemistry and Electron Microscopy", *American Journal of Pathology* 134(2):373-383 (1989).
Strober, Warren and Ehrhardt, Rolf O., "Chronic Intestinal Inflammation: An Unexpected Outcome in Cytokine or T Cell Receptor Mutant Mice", *Cell* 75:203-205 (1993).
Sadlack, Benjamin et al., "Ulcerative Colitis-like Disease in Mice with a Disrupted Interleukin-2 Gene", *Cell* 75:253-261 (1993).
Hamann, Alf et al., "Role of $\alpha_4$-Integrins in Lymphocyte Homing to Mucosal Tissues In Vivo", *Journal of Immunology* 152:3282-3293 (1994).
Cooper, Harry S. et al., "Clinicopathologic Study of Dextran Sulfate Sodium Experimental Murine Colitis", *Laboratory Investigation* 69(2):238-249 (1993).

Podolsky, Daniel K. et al., "Attenuation of Colitis in the Cotton-top Tamarin by Anti-α4 integrin Monoclonal Antibody", *J. Clin. Invest.* 92:372-380 (1993).
Okayasu, Isao et al., "A Novel Method in the Induction of Reliable Experimental Acute and Chronic Ulcerative Colitis in Mice", *Gastroenterology* 98:694-702 (1990).
Podolsky, Daniel K., "Inflammatory Bowel Disease (First of Two Parts)", *The New England Journal of Medicine* 325(13):928-937.
Podolsky, Daniel K., "Inflammatory Bowel Disease (Second of Two Parts)", *The New England Journal of Medicine* 325(14):1008-1016 (1991).
Springer, Timothy A., "The Sensation and Regulation of Interactions with the Extracellular Environment: The Cell Biology of Lymphocyte Adhesion Receptors", *Annu. Rev. Cell Biol.* 6:359-402 (1990).
Dueñas, Marta and Borrebaeck, Carl A.K., "Clonal Selection and Amplification of Phage Displayed Antibodies by Linking Antigen Recognition and Phage Replication", *Bio/Technology* 12:999-1002 (1994).
Picker, Louis, J. and Butcher, Eugene C., "Physiological and Molecular Mechanisms of Lymphocyte Homing", *Annu. Rev. Immunol.* 10:561-591 (1992).
Hynes, Richard O., "Integrins: Versatility, Modulation, and Signaling in Cell Adhesion", *Cell* 69:11-25 (1992).
Michie, Sara A. et al., "The Human Peripheral Lymph Node Vascular Addressin, An Inducible Endothelial Antigen Involved in Lymphocyte Homing", *American Journal of Pathology* 143(6):1688-1698 (1993).
Berlin, Cornelia et al., "α4β7 Integrin Mediates Lymphocyte Binding to the Mucosal Vascular Addressin MAdCAM-1", *Cell* 74:185-195 (1993).
Schweighoffer, Tamas et al., "Selective Expression of Integrin α4β7 on a Subset of Human CD4$^+$ Memory T Cells with Hallmarks of Gut-Trophism", *The Journal of Immunology* 151(2):717-729 (1993).
Springer, Timothy A., "Traffic Signals for Lymphocyte Recirculation and Leukocyte Emigration: The Multistep Paradigm", *Cell* 76:301-314 (1994).
Briskin, Michael J. et al., "MAdCAM-1 has homology to immunoglobulin and mucin-like adhesion receptors and to IgA1", *Nature* 363:461-463 (1993).
Salmi, Marko et al., "Aberrant Binding of Lamina Propria Lymphocytes to Vascular Endothelium in Inflammatory Bowel Diseases", *Gastroenterology* 106:596-605 (1994).

(Continued)

*Primary Examiner*—Ron Schwadron
(74) *Attorney, Agent, or Firm*—McDermott Will & Emery LLP

(57) ABSTRACT

The present invention relates to isolated and/or recombinant nucleic acids which encode naturally occurring primate MAdCAMs, wherein said nucleic acid encodes the polypeptide shown in FIG. 1 (SEQ ID NO:2), the polypeptide shown in FIG. 2 (SEQ ID NO:4), or the polypeptide shown in FIG. 3 (SEQ ID NO:6). The invention further relates to recombinant nucleic acid constructs, comprising a nucleic acid which encodes a naturally occurring primate MAdCAM, wherein said nucleic acid encodes a polypeptide having an amino acid sequence as set forth in FIG. 1 (SEQ ID NO:2), FIG. 2 (SEQ ID NO:4), or FIG. 3 (SEQ ID NO:6); to host cells comprising such constructs, useful for the production of recombinant proteins; the use of nucleic acids and/or proteins in assays to identify inhibitors (e.g., antagonists) of primate MAdCAM function; and to antibodies reactive with primate MAdCAM, which are useful in in vitro methods, diagnostic and/or therapeutic applications.

10 Claims, 12 Drawing Sheets

OTHER PUBLICATIONS

Silber, Alexandra et al., "Recruitment of Lymphocytes during Cutaneous Delayed Hypersensitivity in Nonhuman Primates is Dependent on E-Selectin and Vascular Cell Adhesion Molecule 1", *J. Clin. Invest.* 93:1554-1563 (1994).

Salmi, Marko et al., "Dual Binding Capacity of Mucosal Immunoblasts to Mucosal and Synovial Endothelium in Humans: Dissection of the Molecular Mechanisms", *J. Exp. Med.* 181:137-149 (1995).

Andrew, David P. et al., "Distinct but Overlapping Epitopes Are Involved in $\alpha_4\beta_7$-Mediated Adhesion to Vascular Cell Adhesion Molecule-1, Mucosal Addressin-1, Fibronectin, and Lymphocyte Aggregation", *Journal of Immunology* 153:3847-3861 (1994).

Lazarovits, Andrew I. et al., "I.A Monoclonal Antibody, Anti-Act I, Defines a New Late Lymphocyte Activation Antigen", *Journal of Immunology* 133(4):1857-1862 (1984).

Erle, David J. et al., "Expression and Function of the MAdCAM-1 Receptor, Integrin $\alpha 4\beta 7$, on Human Leukocytes[1]", *Journal of Immunology* 153:517-528 (1994).

Berg, E.L., et al., "L-selectin-mediated lymphocyte rolling on MAdCAM-1", *Nature* 366:695-698 (1993).

Berlin, C., et al., "$\alpha 4$ Integrins Mediate Lymphocyte Attachment and Rolling under Physiologic Flow", *Cell* 80:413-422 (1995).

Bednarczyk, J.L., et al., "Identification of a Combinatorial Epitope Expressed by the Integrin $\alpha 4\beta 1$ Heterodimer Involved in the Regulation of Cell Adhesion", *J. Biol. Chem.*, 269(11):8348-8354 (1994).

Chensue, S.W., et al., "Monocyte Chemotactic Protein Expression During Schistosome Egg Granuloma Formation", *Am. J. of Pathology*, 146(1):130-138 (1995).

Huffnagle, G.B., et al., "The Role of Monocyte Chemotactic Protein-1 (MCP-1) in the Recruitment of Monocytes and CD4[+] T Cells During a Pulmonary *Cryptococcus neoformans Infection*", *J. of Immunology*, 155:4790-4797 (1995).

Taub, D.D., et al., "Monocyte Chemotactic Protein-1 (MCP-1), -2, and -3 Are Chemotactic For Human T Lymphocytes", *J. of Clin. Investigation*, 95:1370-1376 (1995).

Loetsoher, P., et al., "Monocyte Chemotactic Proteins MCP-1, MCP-2, and MCP-3 are Major Attractants for Human CD4[+] and CD8[+] T Lymphocytes", *FASEB J.*, 8:1055-1060 (1994).

Carr, M.W., et al., "Monocyte Chemoattractant Protein 1 Acts as a T-lymphocyte Chemoattractant", *Proc. Natl. Acad. Sci.*, USA, 91:3652-3656 (1994).

Yang, Y., et al., "Construction and Adhesive Properties of a Soluble MAdCAM-1-Fc Chimera Expressed in a Baculovirus System: Phylogenetic Conservation of Receptor-Ligand Interaction", *Scand. J. Immunol.*, 42:235-247 (1995).

Adams et al., "Aberrant Homing of Mucosal T Cells and Extra-Intestinal Manifestations of Inflammatory Bowel Disease," Nature, 6:244-251 (2006).

Adams et al., "Complementary DNA Sequencing: Expressed Sequence Tags and Human Genome Project," Science, 252:1651-1656 (1991).

Adams et al., "Initial Assessment of Human Gene Diversity and Expression Patterns Based Upon 83 Million Nucleotides of cDNA Sequence," Nature (Supp), 377:3-174 (1995).

Andrew et al., "TABS, A T Cell Activation Antigen that Induces LFA-1-Dependent Aggregation," The Journal of Immunology, 155:1671-1684 (1995).

Aruffo et al., "Molecular Cloning of a CD28 cDNA by a High-Efficiency COS Cell Expression System," Proc. Natl. Acad. Sci. USA, 84:8573-8577 (1987).

Brossay et al., "Mimicry of a Neutralizing Epitope of the Major Outer Membrane Protein of Chlamydia Trachomatis by Anti-Idiotypic Antibodies," Infection and Immunity, 62:341-347 (1994).

Calvete et al., "Further Studies on the Topography of Human Platelet Glycoprotein llb," Biochem, 273:767-775 (1991).

Chenna et al., "Multiple Sequence Alignment with the Clustal Series of Programs," Nucleic Acids Research, 31:3497-3500 (2003).

Feagan et al., "Treatment of Ulcerative Colitis with a Humanized Antibody to the $\alpha_4\beta_7$ Integrin," The New England Journal of Medicine, 352:2499:2507 (2005).

Grant et al., "MAdCAM-1 Expressed in Chronic Inflammatory Liver Disease Supports Mucosal Lymphocyte Adhesion to Hepatic Endothelium (MAdCAM-1 in Chronic Inflammatory Liver Disease)," Hepatology, 33:1065-1072 (2001).

Herlyn et al., "Anti-Idiotypic Antibodies Bear the Internal Image of a Human Tumor Antigen," Science 232:100-102 (1986).

Marlin et al., "Purified Intercellular Adhesion Molecule-1 (ICAM-1) is a Ligand for Lymphocyte Function-Associated Antigen 1 (LFA-1)," Cell, 51:813-819 (1987).

Pennica et al., "Expression Cloning of Cardiotrophin 1, A Cytokine that Induces Cardiac Myocyte Hypertrophy," Proc. Natl. Acad. Sci., 92:1142-1146 (1995).

Petrovic et al., "LPAM ($\alpha_4\beta_7$ integrin) is an Important Homing Integrin on Alloreactive T Cells in the Development of Intestinal Graft-Versus-Host Disease," Blood, 103:1542-1547 (2004).

Prakash et al., "Cloning and Analysis of Murine cDNA that Encodes a Fibrogenic Lymphokine, Fibrosin," Proc. Natl. Acad. Sci. USA, 92:2154-2158 (1995).

Prasad et al., "Evaluation of Mutagenesis for Epitope Mapping," The Journal of Biological Chemistry, 15:10705-10708 (1993).

Schweighoffer et al., "Selective Expression of Integrin $\alpha_4\beta_7$ on a Subset of Human CD4+ Memory T Cells with Hallmarks of Gut-Trophism," The Journal of Immunology, 151:717-729 (1993).

Silber et al, "Recruitment of Lymphocytes During Cutaneous Delayed Hypersensitivity in Nonhuman Primates is Dependent on E-Selectin and Vascular Cell Adhesion Molecule 1," J. Clin. Invest., 93:1554-1563 (1994).

Yacyshyn et al, "Crohn's Disease, Ulcerative Colitis, and Normal Intestinal Lymphocytes Express Integrins in Dissimilar Patterns," Gastroenterology, 107:1364-1371 (1994).

Yang et al., "Involvement of $\beta_7$ Integrin and Mucosal Addressin Cell Adhesion Molecule-1 (MAdCAM-1) in the Development of Diabetes in Nonobese Diabetic Mice," Diabetes, 46;1542-1547 (1997).

* cited by examiner

```
ATGGATTTCGGACTGGCCCTCCTGCTGGCGGGGCTTCTGGGGCTCCTCCTCGGCCAGTCCCTCCAGGTGAAGCCCCTGCA  80
 M  D F  G  L  A  L  L  L  A  G  L  L  G  L  L  L  G  Q  S  L  Q  V  K  P  L  Q

GGTGGAGCCCCCGGAGCCGGTGGTGGCCGTGGCCTTGGGCGCCTCGCGCCAGCTCACCTGCCGCCTGGCCTGCGCGGACC 160
 V  E  P  P  E  P  V  V  A  V  A  L  G  A  S  R  Q  L  T [C] R  L  A [C] A  D

GCGGGGCCTCGGTGCAGTGGCGGGGCCTGGACACCAGCCTGGGCGCGGTGCAGTCGGACACGGGCCGCAGCGTCCTCACC 240
 R  G  A  S  V  Q  W  R  G  L  D  T  S  L  G  A  V  Q  S  D  T  G  R  S  V  L  T

GTGCGCAACGCCTCGCTGTCGGCGGCCGGGACCCGCGTGTGCGTGGGCTCCTGCGGGGGCCGCACCTTCCAGCACACCGT 320
 V  R [N  A  S] L  S  A  A  G  T  R  V [C] V  G  S [C] G  G  R  T  F  Q  H  T  V

GCAGCTCCTTGTGTACGCCTTCCCGGACCAGCTGACCGTCTCCCCAGCAGCCCTGGTGCCTGGTGACCCGGAGGTGGCCT 400
 Q  L  L  V  Y  A  F  P  D  Q  L  T  V  S  P  A  A  L  V  P  G  D  P  E  V  A

GTACGGCCCACAAAGTCACGCCCGTGGACCCCAACGCGCTCTCCTTCTCCCTGCTCGTCGGGGGCCAGGAACTGGAGGGG 480
[C] T  A  H  K  V  T  P  V  D  P  N  A  L  S  F  S  L  L  V  G  G  Q  E  L  E  G

GCGCAAGCCCTGGGCCCGGAGGTGCAGGAGGAGGAGGAGGAGCCCAGGGGGACGAGGACGTGCTGTTCAGGGTGACAGA  560
 A  Q  A  L  G  P  E  V  Q  E  E  E  E  E  P  Q  G  D  E  D  V  L  F  R  V  T  E

GCGCTGGCGGCTGCCGCCCCTGGGGACCCCTGTCCCGCCCGCCCTCTACTGCCAGGCCACGATGAGGCTGCCTGGCTTGG 640
 R  W  R  L  P  P  L  G  T  P  V  P  P  A  L  Y [C] Q  A  T  M  R  L  P  G  L

AGCTCAGCCACCGCCAGGCCATCCCCGTCCTGCAC AGCCCGACCTCCCCGGAGCCTCCCGACACCACCTCCCCGGAGCCT 720
 E  L  S  H  R  Q  A  I  P  V  L  H | S  P  T  S  P  E  P  P  D  T  T  S  P  E  P

CCCAACACCACCTCCCCGGAGTCTCCCGACACCACCTCCCCGGAGTCTCCCGACACCACCTCCCAGGAGCCTCCCGACAC 800
 P [N  T  T] S  P  E  S  P  D  T  T  S  P  E  S  P  D  T  T  S  Q  E  P  P  D  T

CACCTCCCAGGAGCCTCCCGACACCACCTCCCAGGAGCCTCCCGACACCACCTCCCCGGAGCCTCCCGACAAGACCTCCC 880
 T  S  Q  E  P  P  D  T  T  S  Q  E  P  P  D  T  T  S  P  E  P  P  D  K  T  S

CGGAGCC GCCCCCCAGCAGGGCTCCACACACACCCCCAGGAGCCCAGGCTCCACCAGGACTCGCCGCCCTGAGATCTCC 960
 P  E  P| A  P  Q  Q  G  S  T  H  T  P  R  S  P  G  S  T  R  T  R  R  P  E  I  S

CAGGCTGGGCCCACGCAGGGAGAAGTGATCCCAACAGGCTCGTCCAAACCTGCGGGTGACCAGCTGCCCGCGGCTCTGTG 1040
 Q  A  G  P  T  Q  G  E  V  I  P  T  G  S  S  K  P  A  G  D  Q  L  P  A  A  L  W

GACCAGCAGTGCGGTGCTGGGACTGCTGCTCCTGGCCTTGCCCACGTATCACCTCTGGAAACGCTGCCGGCACCTGGCTG 1120
    T  S  S  A  V  L  G  L  L  L  L  A  L  P  T  Y  H  L  W  K  R  C  R  H  L  A

AGGACGACACCCACCCACCAGCTTCTCTGAGGCTTCTGCCCCAGGTGTCGGCCTGGGCTGGGTTAAGGGGGACCGGCCAG 1200
 E  D  D  T  H  P  P  A  S  L  R  L  L  P  Q  V  S  A  W  A  G  L  R  G  T  G  Q

GTCGGGATCAGCCCCTCCTGAGTGGCCAGCCTTTCCCCCTGTGAAAGCAAAATAGCTTGGACCCCTTCAAGTTGAGAACT 1280
 V  G  I  S  P  S

GGTCAGGGCAAACCTGCCTCCCATTCTACTCAAAGTCATCCCTCTGCTCACAGAGATGGATGCATGTTCTGATTGCCTCT 1360

TTGGAGAAGCTCATCAGAAACTCAAAAGAAGGCCACTGTTTGTCTCACCTACCCATGACCTGAAGCCCCTCCCTGAGTGG 1440

TCCCCACCTTTCTGGACGGAACCACGTACTTTTTACATACATTGATTCATGTCTCACGTCTCCCTAAAAATGCGTAAGAC 1520

CAAGCTGTGCCCTGACCACCCTGGGCCCCTGTCGTCAGGACCTCCTGAGGCTTTGGCAAATAAACCTCCTAAAATGATAA 1600

AAAAAAAAAAAAAAAAAAAAAAAAA 1624
```

FIGURE 1

```
ATGGATTTCGGACTGGCCCTCCTGCTGGCGGGGCTTCTGGGGCTCCTCCTCGGCCAGTCCCTCCAGGTGAAGCCCCTGCA  80
 M  D  F  G  L  A  L  L  L  A  G  L  L  G  L  L  L  G  Q  S  L  Q  V  K  P  L  Q

GGTGGAGCCCCCGGAGCCGGTGGTGGCCGTGGCCTTGGGCGCCTCGCGCCAGCTCACCTGCCGCCTGGCCTGCGCGGACC 160
 V  E  P  P  E  P  V  V  A  V  A  L  G  A  S  R  Q  L  T  [C] R  L  A  [C] A  D

GCGGGGCCTCGGTGCAGTGGCGGGGCCTGGACACCAGCCTGGGCGCGGTGCAGTCGGACACGGGCCGCAGCGTCCTCACC 240
 R  G  A  S  V  Q  W  R  G  L  D  T  S  L  G  A  V  Q  S  D  T  G  R  S  V  L  T

GTGCGCAACGCCTCGCTGTCGGCGGCCGGGACCCGCGTGTGCGTGGGCTCCTGCGGGGGCCGCACCTTCCAGCACACCGT 320
 V  R  [N  A  S] L  S  A  A  G  T  R  V  [C] V  G  S  [C] G  G  R  T  F  Q  H  T  V

GCAGCTCCTTGTGTACGCCTTCCCGGACCAGCTGACCGTCTCCCCAGCAGCCCTGGTGCCTGGTGACCCGGAGGTGGCCT 400
 Q  L  L  V  Y  A  F  P  D  Q  L  T  V  S  P  A  A  L  V  P  G  D  P  E  V  A

GTACGGCCCACAAAGTCACGCCCGTGGACCCCAACGCGCTCTCCTTCTCCCTGCTCGTCGGGGGCCAGGAACTGGAGGGG 480
[C] T  A  H  K  V  T  P  V  D  P  N  A  L  S  F  S  L  L  V  G  G  Q  E  L  E  G

GCGCAAGCCCTGGGCCCGGAGGTGCAGGAGGAGGAGGAGGAGCCCCAGGGGGACGAGGACGTGCTGTTCAGGGTGACAGA 560
 A  Q  A  L  G  P  E  V  Q  E  E  E  E  E  P  Q  G  D  E  D  V  L  F  R  V  T  E

GCGCTGGCGGCTGCCGCCCCTGGGGACCCCTGTCCCGCCCGCCCTCTACTGCCAGGCCACGATGAGGCTGCCTGGCTTGG 640
 R  W  R  L  P  P  L  G  T  P  V  P  P  A  L  Y [C] Q  A  T  M  R  L  P  G  L

AGCTCAGCCACCGCCAGGCCATCCCCGTCCTGCACAGCCCGACCTCCCCGGAGCCTCCCGACACCACCTCCCCGGAGTCT 720
 E  L  S  H  R  Q  A  I  P  V  L  H  S  P  T  S  P  E  P  P  D  T  T  S  P  E  S

CCCGACACCACCTCCCCGGAGTCTCCCGACACCACCTCCCCAGGAGCCTCCCGACACCACCTCCCCGGAGCCTCCCGACAA 800
 P  D  T  T  S  P  E  S  P  D  T  T  S  Q  E  P  P  D  T  T  S  P  E  P  P  D  K

GACCTCCCCGGAGCCGCCCCCCAGCAGGGCTCCACACACACCCCAGGAGCCCAGGCTCCACCAGGACTCGCCGCCCTG 880
 T  S  P  E  P  A  P  Q  Q  G  S  T  H  T  P  R  S  P  G  S  T  R  T  R  R  P

AGATCTCCCAGGCTGGGCCCACGCAGGGAGAAGTGATCCCAACAGGCTCGTCCAAACCTGCGGGTGACCAGCTGCCCGCG 960
 E  I  S  Q  A  G  P  T  Q  G  E  V  I  P  T  G  S  S  K  P  A  G  D  Q  L  P  A

GCTCTGTGGACCAGCAGTGCGGTGCTGGGACTGCTGCTCCTGGCCTTGCCCACCTATCACCTCTGGAAACGCTGCCGGCA 1040
 A  L  W  T  S  S  A  V  L  G  L  L  L  L  A  L  P  T  Y  H  L  W  K  R  C  R  H

CCTGGCTGAGGACGACACCCACCCACCAGCTTCTCTGAGGCTTCTGCCCCAGGTGTCGGCCTGGGCTGGGTTAAGGGGGA 1120
 L  A  E  D  D  T  H  P  P  A  S  L  R  L  L  P  Q  V  S  A  W  A  G  L  R  G

CCGGCCAGGTCGGGATCAGCCCCTCCTGAGTGGCCAGCCTTTCCCCCTGTGAAAGCAAAATAGCTTGGACCCCTTCAAGT 1200
 T  G  Q  V  G  I  S  P  S

TGAGAACTGGTCAGGGCAAACCTGCCTCCCATTCTACTCAAAGTCATCCCTCTGTTCACAGAGATGGATGCATGTTCTGA 1280

TTGCCTCTTTGGAGAAGCTCATCAGAAACTCAAAAGAAGGCCACTGTTTGTCTCACCTACCCATGACCTGAAGCCCCTCC 1360

CTGAGTGGTCCCCACCTTTCTGGACGGAACCACGTACTTTTTACATACATTGATTCATGTCTCACGTCTCCCTAAAAATG 1440

CGTAAGACCAAGCTGTGCCCTGACCACCCTGGGCCCCTGTCGTCAGGACCTCCTGAGGCTTTGGCAAATAAACCTCCTAA 1520

AATGAAAAAAAAAAAAAAA 1539
```

FIGURE 2

```
AGCATGGATCGGGGCCTGGCCCTCCTGCTGGCGGGGCTTCTGGGGCTCCTCCAGCCGGGCTGCGGCCAGTCCCTCCAGGT  80
    M  D  R  G  L  A  L  L  L  A  G  L  L  G  L  L  Q  P  G  C  G  Q  S  L  Q  V
GAAGCCCCTGCAGGTGGAGCCCCCGGAGCCGGTGGTGGCCGTGGCCCTGGGCGCCTCTCGCCAGCTCACCTGCCGCCTGG 160
 K  P  L  Q  V  E  P  P  E  P  V  V  A  V  A  L  G  A  S  R  Q  L  T [C] R  L
ACTGCGCGGACCGCGGGGCCACGGTGCAGTGGCGGGGCCTGGACACCAGCCTGGGCGCGGTGCAGTCGGACGCGGGCCGC 240
 D [C] A  D  R  G  A  T  V  Q  W  R  G  L  D  T  S  L  G  A  V  Q  S  D  A  G  R
AGCGTCCTCACCGTGCGCAACGCCTCGCTGTCGGCGGCCGGGACCCGTGTGTGCGTGGGCTCCTGCGGGGGCCGCACCTT 320
 S  V  L  T  V  R  N  A  S  L  S  A  A  G  T  R  V [C] V  G  S [C] G  G  R  T  F
CCAGCACACCGTGCGGCTCCTTGTGTACGCCTTCCCGGACCAGCTGACCATCTCCCGGCAGCCCTGGTGCCTGGTGACC  400
 Q  H  T  V  R  L  L  V  Y  A  F  P  D  Q  L  T  I  S  P  A  A  L  V  P  G  D
CGGAGGTGGCCTGTACGGCCCACAAAGTCACGCCTGTGGACCCCAATGCGCTCTCCTTCTCCCTGCTCCTGGGGGACCAG 480
 P  E  V  A [C] T  A  H  K  V  T  P  V  D  P  N  A  L  S  F  S  L  L  L  G  D  Q
GAACTGGAGGGGGCCCAGGCTCTGGGCCCGGAGGTGGAGGAGGAGGAGGAGGAGCCCCAGGAGGAGGAGGACGTGCTGTT 560
 E  L  E  G  A  Q  A  L  G  P  E  V  E  E  E  E  E  P  Q  E  E  E  D  V  L  F
CAGGGTGACAGAGCGCTGGCGGCTGCCGACCCTGGCAACCCCTGTCCTGCCCGCGCTCTACTGCCAGGCCACGATGAGGC 640
 R  V  T  E  R  W  R  L  P  T  L  A  T  P  V  L  P  A  L  Y [C] Q  A  T  M  R
TGCCTGGCTTGGAGCTCAGCCACCGCCAGGCCATCCCGGTCCTGCAC GGCCCGACCTCCCGGGAGCCCCCCGACACGACC 720
 L  P  G  L  E  L  S  H  R  Q  A  I  P  V  L  H  G  P  T  S  R  E  P  P  Q  T  T
TCCCCGGAACCCCGGGCCGCGACCTCCCCGGAGACCACCCCCAGCAGGGCTCCACACACAGCCCCAGGAGCCCGGGCTC  800
 S  P  E  P  R  A  A  T  S  P  E  T  T  P  Q  Q  G  S  T  H  S  P  R  S  P  G  S
TACCAGGACTTGCCGCCCTGAGATCTCCCAGGCTGGGCCCACGCAGGGAGAAGTGATCCCAACAGGCTCGTCCAAACCTA 880
 T  R  T  C  R  P  E  I  S  Q  A  G  P  T  G  E  V  I  P  T  G  S  S  K  P
CGGGTGACCAGCTGCCCGCGGCTCTGTGGACCAGCAGTGCGGTGCTGGGACTGCTGCTCCTGGCTTTGCCCACCTACCAC 960
 T  G  D  Q  L  P  A  A  L  W  T  S  S  A  V  L  G  L  L  L  L  A  L  P  T  Y  H
CTCTGGAAACGTTGCCGGCACCTGGCTGAGGACGGCGCCCACCCACCAGCTTCTCTGAGTAGCCAGCCCTTCCCCCTGTG 1040
 L  W  K  R  C  R  H  L  A  E  D  G  A  H  P  P  A  S  L  S  S  Q  P  F  P  L
AAGGGAAAATAGGTTGGACCCCTTCAAGCTGAGAACTGGTCGGGGCAAACCTGCCTCCCATTCTATTCAAAGTCATCGCT 1120

CTGGTCACAGAGAGGGACGCACATTCTGATTGCCTCCTTTGGAAAGGCTCATCAGAAACTCAAAAGAAGGTGATCGTTTG 1200

TCCCGCCTACCCGTGACCTGGAAGCCCCCGCCCCGCTCGAGTGACCCCTGACTTTCTGGACGGAACCAACGTACTTCTTA 1280

CATATATTGATTCATGTGTCATATCTCCCTAAAATGCGTAAAACCAGCTGTGCCCCGACCACCTTGGGCCCCTGCCATCA 1360

GGACCTCCTGAGGCTTTGGCAAATAAACCTCCTAAAAGGATAGAAACTGAAACTTGTGGCCGGGCGCGGTGGCTCAAGCC 1440

TGTAATCCCAGCACTTTGGGAGGCCGAGGTGGGTGGATCACGAGGTCAGGAGATCGAGACCATCCTGGCTAACCCGTGAA 1520

ACCCCGTCTCTACTAAAAAAATACAAAAATTAGCCGGGAGCGGTGGCGGGCGCCTGTAGTCCCAGCTACTCGGGAGGCTG 1600

AGGCAGGAGAATGGCGTGAACCCGGGAGGCGGAGCTTGCAGTGAGCTGAGATCCGGCCACTGCACTCCAGCCTGGGGGAC 1680

AGAGCGAGACTCCGTCTCAAAAAAAAAAAAAAAAAAAAAAA 1721
```

FIGURE 3

MUCOSAL VASCULAR ADDRESSINS

BACKGROUND OF THE INVENTION

Lymphocyte homing from the circulation to the lymphoid tissues and migration to sites of inflammation is regulated by interaction with receptors expressed in postcapillary venules, including high endothelial venules (HEV) found in secondary lymphoid tissues (e.g., mesenteric lymph nodes, Peyer's Patches (PP)) (Bevilacqua, M. P., *Annu. Rev. Immunol.,* 11:767-804 (1993); Butcher, E. C., *Cell,* 67: 1033-1036 (1991); Picker, L. J., et al., *Annu. Rev. Immunol.,* 10:561-591 (1992); and Springer, T. A., *Cell,* 76: 301-314 (1994)). These interactions are tissue specific in nature.

Inflammation (e.g., chronic inflammation) is characterized by infiltration of the affected tissue by leukocytes, such as lymphocytes, lymphoblasts, and mononuclear phagocytes. The remarkable selectivity by which leukocytes preferentially migrate to various tissues during both normal circulation and inflammation results from a series of adhesive and activating events involving multiple receptor-ligand interactions as proposed by Butcher and others (Butcher, E. C., *Cell,* 67: 1033-1036 (1991); vonAndrain, U. H., et al., *Proc. Natl. Acad. Sci. USA,* 88:7538 (1991); Mayadas, T. N., et al., *Cell,* 74:541 (1993); (Springer, T. A., *Cell,* 76:301 (1994)). As an initial step, there is a transient, rolling interaction between leukocytes and endothelium, which results from the interaction of selectins (and by α4 integrins in some instances) with their carbohydrate ligands. This interaction which is characterized by rolling in the direction of flow can be assessed by known methods (Lawrence, M. B. and T. A. Springer, *Cell,* 65:859 (1991); WO 92/21746, Springer et al., (Dec. 10, 1992)). This is followed by activation events mediated by chemoattractants such as chemokines and their receptors, which cause activation of integrin adhesiveness and influence the direction of migration of leukocytes through vascular walls. Such secondary signals in turn trigger the firm adhesion of leukocytes to endothelium via leukocyte integrins and their endothelial ligands (Ig-like receptors and the ECM), and subsequent transendothelial migration from the circulation across the vascular endothelium.

In secondary lymphoid tissues, such as Peyer's patches (PPs) and lymph nodes (e.g., peripheral lymph nodes (PLN)), leukocyte trafficking and homing is regulated by interactions of homing receptors on the surface of leukocytes with endothelial cells lining the post-capillary venules, notably high endothelial venules (HEV) (Gowans, J. L. and E. J. Knight, *Proc. R. Soc. Lond.,* 159:257 (1964)). Receptors termed vascular addressins, which are present on the endothelial cell surface and regulate the migration and subsequent extravasation of lymphocyte subsets. The vascular addressins show restricted patterns of expression and this tissue specific expression makes an important contribution to the specificity of leukocyte trafficking (Picker, L. J. and E. C. Butcher, *Annu. Rev. Immunol.,* 10:561-591 (1992); Berg, E. L., et al., *Cellular and molecular mechanisms of inflammation,* 2:111 (1991); Butcher, E. C., *Cell,* 67: 1033-1036 (1991)).

Mucosal vascular addressin MAdCAM-1 (Mucosal Addressin Cell Adhesion Molecule-1) is an immunoglobulin superfamily adhesion receptor for lymphocytes, which is distinct from VCAM-1 and ICAM-1. MAdCAM-1 was identified in the mouse as a ~60 kd glycoprotein which is selectively expressed at sites of lymphocyte extravasation. In particular, MAdCAM-1 expression was reported in vascular endothelial cells of mucosal tissues, including gut-associated tissues or lymphoid organs, such as Peyer's patches and venules of the lamina propria of the small and large intestine, and the lactating mammary gland, but not in peripheral lymph nodes. MAdCAM-1 is involved in lymphocyte binding to Peyer's Patches. (Streeter, P. R., et al., *Nature,* 331:41-46 (1988); Nakache, M., et al., *Nature,* 337: 179-181 (1989); Picker, L. J., et al., *Annu. Rev. Immunol.,* 10:561-591 (1992); Briskin, M. J., et al., *Nature,* 363:461 (1993); Berg, E. L., et al., *Nature,* 366:695-698 (1993); Berlin, C., et al., *Cell,* 74:185-195 (1993)). MAdCAM-1 can be induced in vitro by proinflammatory stimuli (Sikorski, E. E., et al., *J. Immunol.,* 151: 5239-5250 (1993)).

MAdCAM-1 specifically binds the lymphocyte integrin α4β7 (also referred to as LPAM-1 (mouse), α4βp (mouse) and CD49d/CD⁻ (human)), which is a lymphocyte homing receptor involved in homing to Peyer's patches (Berlin, C., et al., *Cell,* 80:413-422 (1994); Berlin, C., et al., *Cell,* 74:185-195 (1993); and Erle, D. J., et al., *J. Immunol.,* 153: 517-528 (1994)). In contrast to VCAM-1 and fibronectin, which interact with both α4β1 and α4β7 (Berlin, C., et al., *Cell,* 74:185-195 (1993); Strauch, U. S., et al., *Int. Immunol.,* 6:263 (1994)), MAdCAM-1 is a selective receptor for α4β7.

Inflammatory bowel disease (IBD), such as ulcerative colitis and Crohn's disease, for example, can be a debilitating and progressive disease involving inflammation of the gastrointestinal tract. Affecting an estimated two million people in the United States alone, symptoms include abdominal pain, cramping, diarrhea and rectal bleeding. IBD treatments have included anti-inflammatory drugs (such as, corticosteroids and sulfasalazine), immunosuppressive drugs (such as, 6-mercaptopurine, cyclosporine and azathioprine) and surgery (such as, colectomy). Podolsky, *New Engl. J. Med.,* 325:928-937 (1991) and Podolsky, *New Engl. J. Med.,* 325: 1008-1016 (1991).

Some studies have suggested that the cell adhesion molecule, ICAM-1, mediates leukocyte recruitment to inflammatory sites through adhesion to leukocyte surface ligands, i.e., Mac-1, LFA-1 or α4β2 (Springer, *Nature,* 346:425-434 (1990)). In addition, vascular cell adhesion molecule-1 (VCAM-1), which recognizes the α4β1 integrin (VLA-4), has been reported to play a role in in vivo leukocyte recruitment (Silber et al., *J. Clin. Invest.* 93:1554-1563 (1994)). It has been proposed that IBD can be treated by blocking the interaction of ICAM-1 with LFA-1 or Mac-1, or of VCAM-1 with α4β1 (e.g., WO 93/15764). However, these therapeutic targets are likely to be involved in inflammatory processes in multiple organs, and a functional blockade could cause systemic immune dysfunction.

In contrast to VCAM-1 and ICAM-1, MAdCAM is preferentially expressed in the gastrointestinal tract, binds the α4β7 integrin found on lymphocytes, and participates in the homing of these cells to mucosal sites, such as Peyer's patches in the intestinal wall (Hamann et al., *Journal of Immunology,* 152:3282-3293 (1994)). The use of inhibitors to the binding of MAdCAM to the receptor, α4β7 in the treatment of diseases such as IBD has not been suggested. Moreover, although human α4 and β7 genes and proteins have been identified (Yuan et al., *Int. Immunol.,* 2: 1097-1108 (1990); Erle et al., *J. Biol. Chem.,* 266:11009-11016 (1991); Bevilacqua, M. P., *Annu. Rev. Immunol.,* 11:767-804 (1993); Springer, T. A., *Cell,* 76: 301-314 (1994)), human or primate MAdCAM-1 has not been cloned or characterized.

SUMMARY OF THE INVENTION

The present invention relates to proteins or polypeptides, referred to herein as isolated and/or recombinant (e.g., essentially pure) primate MAdCAMs. In one embodiment, primate MAdCAM can selectively bind to cells which express the α4β7 integrin, particularly lymphocytes. The recombinant proteins of the present invention, including variants, can be produced in host cells as described herein. In addition, antibodies reactive with the proteins of the present invention can be produced using a primate MAdCAM or a variant thereof as immunogen, for example. Such antibodies or fragments thereof are useful in therapeutic, diagnostic and research applications. For example, the antibodies can be used in the purification and study of MAdCAMs, the identification of cells which express MAdCAM, and the detection or quantitation of MAdCAM in a sample.

The invention further relates to isolated and/or recombinant (e.g., essentially pure) nucleic acids which encode a primate MAdCAM, such as human MAdCAMs. In another aspect, the invention relates to recombinant nucleic acid constructs, such as plasmids or retroviral vectors, which contain a nucleic acid which encodes a protein of the present invention or portion thereof. The nucleic acids and constructs can be used to produce recombinant primate MAdCAMs. In another embodiment, the nucleic acid encodes an antisense nucleic acid which can hybridize with a second nucleic acid encoding a primate MAdCAM, and which can inhibit the expression of the protein (e.g., when introduced into cells).

Also encompassed by the present invention are methods of identifying ligands and/or inhibitors (e.g., antagonists) of MAdCAM function. For example, primate MAdCAM or variants thereof can be used in assays (e.g., adhesion assays) designed to identify antagonists which block the binding of MAdCAM to the ligand, α4β7 integrin.

The invention further relates to the treatment of individuals suffering from a disease associated with leukocyte recruitment to the gastrointestinal tract as a result of binding of leukocytes to gut-associated endothelium expressing the molecule MAdCAM, comprising administering to the individual (e.g., a mammal, such as a primate) an effective amount of an agent or compound, such as an antibody, which inhibits the binding of leukocytes to endothelial MAdCAM. The antibody is preferably a monoclonal, chimeric and/or humanized antibody or an antigen binding fragment thereof, and inhibits adhesion of leukocytes expressing an integrin containing the β7 chain (such as α4β7) to endothelium expressing MAdCAM. In one embodiment, the monoclonal antibody or antigen binding fragment thereof has the antigenic specificity of a monoclonal antibody selected from the group consisting of a FIB 21, FIB 30, FIB 504 and ACT-1. Inflammatory bowel diseases, such as but not limited to ulcerative colitis, Crohn's disease, Pouchitis, celiac disease, microscopic or collagenous colitis, and eosinophilic gastroenteritis can be treated according to the claimed method.

BRIEF DESCRIPTION OF THE DRAWINGS

FIG. 1 is an illustration of the nucleotide sequence (SEQ ID NO:1) determined from subclones of cDNA clone 4 encoding human MAdCAM-1, and the sequence of the predicted protein encoded by the open reading frame (MAdCAM-1; SEQ ID NO:2). The predicted signal peptide and transmembrane region are underlined in bold. Cysteine residues of the two Ig-like domains are boxed, as are potential N-linked glycosylation sites. The mucin domain, containing the PPDTTS(Q/P)E repeat (see e.g., amino acid residues 264-271 and 232-239, respectively, of SEQ ID NOS:1 and 2) consisting of 71 amino acids is outlined by a thin bold line (amino acid residues 226-296 of SEQ ID NOS:1 and 2).

FIG. 2 is an illustration of the nucleotide sequence (SEQ ID NO:3) determined from subclones of cDNA clone 20 encoding human MAdCAM-1, and the sequence of the predicted protein encoded by the open reading frame (MAdCAM-1; SEQ ID NO:4). The predicted signal peptide and transmembrane region are underlined in bold. Cysteine residues of the two Ig-like domains are boxed, as are potential N-linked glycosylation sites. The mucin domain, containing the PPDTTS(Q/P)E repeat identified in clone 4 (see e.g., amino acid residues 264-271 and 232-239, respectively, of SEQ ID NOS:1 and 2) consisting of 47 amino acids is outlined by a thin bold line (amino acids 226-272 of SEQ ID NOS:3 and 4).

FIG. 3 is an illustration of the nucleotide sequence (SEQ ID NO:5) determined from subclones of cDNA clone 31D encoding macaque MAdCAM-1, and the sequence of the predicted protein encoded by the open reading frame (MAdCAM-1; SEQ ID NO:6). The predicted signal peptide and transmembrane region are underlined in bold. Cysteine residues of the two Ig-like domains are boxed. The mucin domain, which contains a single copy of the PPDTTS(Q/P)E repeat identified in clone 4 (see e.g., amino acid residues 264-271 and 232-239, respectively, of SEQ ID NOS:1 and 2), is outlined by a thin bold line (amino acid residues 229-292 of SEQ ID NOS:5 and 6).

FIG. 4A illustrates the results of an experiment in which RPMI 8866 cells ($0.5 \times 10^6$/well), which express α4β7 (and not α4β1), bound to CHO/P cells expressing murine or human MAdCAM-1, but did not bind to CHO/P cells transfected with human VCAM-1 or to CHO/P cells transfected with pcDNA-3. FIG. 4B illustrates the results of an experiment in which CHO/P cells transfected with human VCAM-1 bound to Jurkat cells (which express high levels of α4β1), but failed to bind to CHO/P cells transfected with murine or human MAdCAM-1 or to CHO/P cells transfected with pcDNA-3 as a control. Binding is shown as the number of bound RPMI 8866 cells per CHO/P cell (FIG. 4A) or bound Jurkat cells per CHO/P cell (FIG. 4B) in an average of at least four fields (10× objective)+/− standard error. Binding reactions included control IgG, anti-α4β7 (monoclonal antibody ACT-1), or anti-murine MAdCAM-1 (monoclonal antibody MECA-367) as indicated.

DETAILED DESCRIPTION OF THE INVENTION

Proteins and Peptides

Figure 4A:
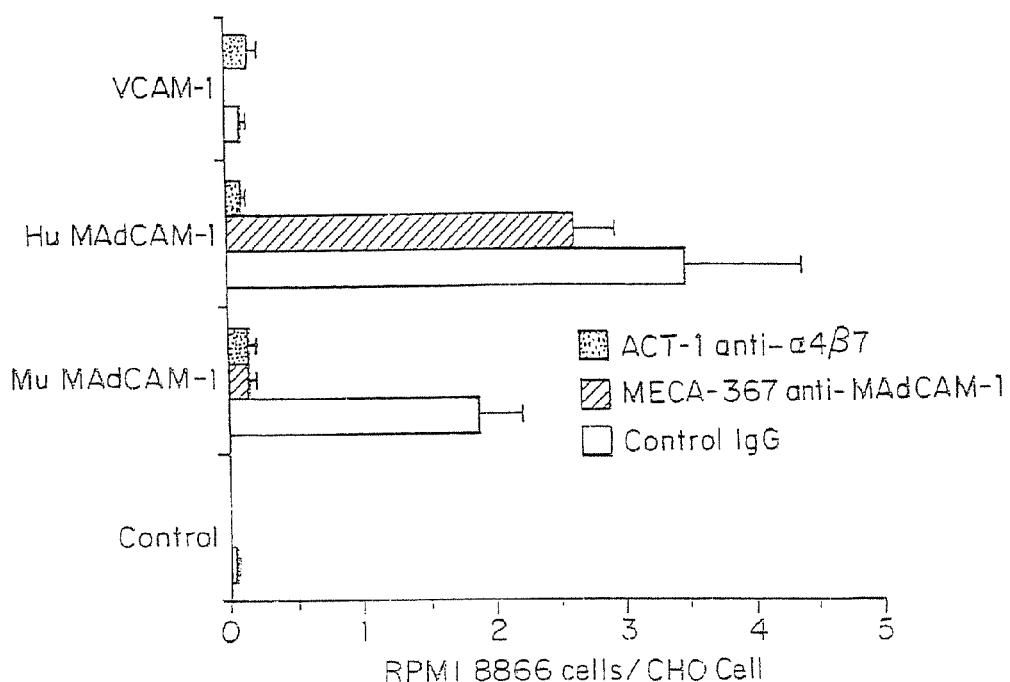
FIGS. 4A-4B are histograms illustrating the selective binding of cells transfected with human MAdCAM-1 to lymphocytes expressing α4β7.

The present invention relates to isolated and/or recombinant (including, e.g., essentially pure) proteins or polypeptides designated primate MAdCAMs (Mucosal Addression Cell Adhesion Molecules) and variants of primate MAdCAMs. In a preferred embodiment, the isolated and/or recombinant proteins of the present invention have at least property, activity or function characteristic of a primate MAdCAM (as defined herein), such as binding function (e.g., the ability to bind an $\alpha 4\beta 7$ integrin), and/or cellular adhesion molecule function (e.g., the ability to mediate cellular adhesion such as $\alpha 4\beta 7$-dependent adhesion in vitro and/or in vivo), and/or an immunological property as defined herein. For example, some proteins of the present invention can selectively bind to an $\alpha 4\beta 7$ integrin and thereby mediate $\alpha 4\beta 7$-dependent cellular adhesion to cells bearing the $\alpha 4\beta 7$ integrin, such as leukocytes (especially lymphocytes such as T or B cells) in vitro and/or in vivo. In one aspect, proteins of the present invention can mediate heterotypic cell adhesion (e.g., of endothelial cells to leukocytes such as lymphocytes).

In another embodiment, proteins of the present invention can bind a primate $\alpha 4\beta 7$ integrin from the same or a different primate species, and/or have cellular adhesion molecule function (e.g., the ability to mediate cellular adhesion such as $\alpha 4\beta 7$-dependent adhesion in vitro and/or in vivo). For example, as shown herein, human and macaque MAdCAM-1 proteins, produced in mammalian cells by expression of cDNA clones, can selectively bind to $\alpha 4\beta 7$ integrin present on human lymphocytes, and can function as cellular adhesion molecules capable of mediating selective adhesion to cells bearing the $\alpha 4\beta 7$ integrin.

Proteins or polypeptides referred to herein as "isolated" are proteins or polypeptides purified to a state beyond that in which they exist in mammalian cells. "Isolated" proteins or polypeptides include proteins or polypeptides obtained by methods described herein, similar methods or other suitable methods, including essentially pure proteins or polypeptides, proteins or polypeptides produced by chemical synthesis (e.g., synthetic peptides), or by combinations of biological and chemical methods, and recombinant proteins or polypeptides which are isolated. The proteins can be obtained in an isolated state of at least about 50% by weight, preferably at least about 75% by weight, and more preferably, in essentially pure form. Proteins or polypeptides referred to herein as "recombinant" are proteins or polypeptides produced by the expression of recombinant nucleic acids.

As used herein "primate MAdCAM" refers to naturally occurring or endogenous primate MAdCAM proteins, to proteins having an amino acid sequence which is the same as that of a naturally occurring or endogenous corresponding primate MAdCAM (e.g., recombinant proteins), and to functional variants of each of the foregoing (e.g., functional fragments and/or mutants produced via mutagenesis and/or recombinant techniques). Accordingly, as defined herein, the term includes mature primate MAdCAM, glycosylated or unglycosylated MAdCAM proteins, polymorphic or allelic variants, and other isoforms of primate MAdCAM (e.g., produced by alternative splicing or other cellular processes), and functional fragments.

Naturally occurring or endogenous primate MAdCAM proteins includes wild type proteins such as mature MAdCAM, polymorphic or allelic variants and other isoforms which occur naturally in primates (e.g., humans or other non-human primates, such as macaque, cotton top tamarin). Such proteins can be recovered from a source which naturally produces primate MAdCAM. These proteins and primate MAdCAM proteins having the same amino acid sequence as a naturally occurring or endogenous corresponding primate MAdCAM, are referred to by the name of the corresponding primate. For example, where the corresponding primate is a human, the protein is designated as a human MAdCAM protein (e.g., a recombinant human MAdCAM produced in a suitable host cell).

"Functional variants" of primate MAdCAMs include functional fragments, functional mutant proteins, and/or functional fusion proteins. Generally, fragments or portions of primate MAdCAM encompassed by the present invention include those having a deletion (i.e., one or more deletions) of an amino acid (i.e., one or more amino acids) relative to the mature primate MAdCAM (such as N-terminal, C-terminal or internal deletions). Fragments or portions in which only contiguous amino acids have been deleted or in which non-contiguous amino acids have been deleted relative to mature primate MAdCAM are also envisioned.

Generally, mutants or derivatives of primate MAdCAMs, encompassed by the present invention include natural or artificial variants differing by the addition, deletion and/or substitution of one or more contiguous or non-contiguous amino acid residues, or modified polypeptides in which one or more residues is modified, and mutants comprising one or more modified residues. Preferred mutants are natural or artificial variants of primate MAdCAM differing by the addition, deletion and/or substitution of one or more contiguous or non-contiguous amino acid residues.

A "functional fragment or portion", "functional mutant" and/or "functional fusion protein" of a primate MAdCAM refers to an isolated and/or recombinant protein or oligopeptide which has at least one property, activity and/or function characteristic of a primate MAdCAM, such as binding function (e.g., the ability to bind an $\alpha 4\beta 7$ integrin), and/or cellular adhesion molecule function (e.g., the ability to mediate cellular adhesion such as $\alpha 4\beta 7$-dependent adhesion in vitro and/or in vivo), and/or retains at least one immunological property of a primate MAdCAM.

As used herein, a protein, polypeptide or oligopeptide having "at least one immunological property" of a primate MAdCAM is one which (a) is bound by at least one antibody of a selected epitopic specificity which binds to a naturally occurring or endogenous primate MAdCAM or to a protein having the same amino acid sequence as the naturally occurring or endogenous primate MAdCAM (e.g., human MAdCAM-1), and/or (b) is an immunogen capable of inducing the formation in a suitable animal of an antibody of a selected epitopic specificity which binds to a naturally occurring or endogenous primate MAdCAM or to a protein having the same amino acid sequence as the naturally occurring or endogenous primate MAdCAM. For example, a suitable fragment can cross-react with an antibody which is raised against and/or reactive with isolated primate MAdCAM.

Suitable fragments or mutants can be identified by screening. For example, the N-terminal, C-terminal, or internal regions of the protein can be deleted in a step-wise fashion and the resulting protein or polypeptide screened using a suitable binding or adhesion assay, such as an assay described herein. Where the resulting protein displays activity in the assay, the resulting protein ("fragment") is functional. Information regarding the structure and function of murine MAdCAM and other adhesion molecules, and of primate MAdCAMs as shown herein, provides a basis for dividing primate MAdCAM into functional domains (see below).

The term variant also encompasses fusion proteins, comprising a primate MAdCAM (e.g., mature human MAdCAM-1) as a first moiety, linked to a second moiety not occurring in the primate MAdCAM as found in nature. Thus, the second moiety can be an amino acid, oligopeptide or polypeptide. The first moiety can be in an N-terminal location, C-terminal location or internal to the fusion protein. In one embodiment, the fusion protein comprises a human MAdCAM or portion thereof as the first moiety, and a second moiety comprising a linker sequence and affinity ligand (e.g., an enzyme, an antigen, epitope tag).

In another embodiment, the fusion protein is a hybrid immunoglobulin, such as a hybrid comprising a primate MAdCAM moiety fused at its C-terminus, to the N-terminus of an immunoglobulin moiety (e.g., one or more immunoglobulin constant regions, preferably of primate origin), such as those prepared according to Capon et al., U.S. Pat. No. 5,428,130). These or other recombinant soluble receptor molecules can be used in assays to identify inhibitors of primate MAdCAM:α4β7 interaction.

Examples of "primate MAdCAM" proteins include proteins encoded by a human or macaque MAdCAM-1 nucleic acid of the present invention, such as a protein having an amino acid sequence as set forth or substantially as set forth in FIG. 1 (SEQ ID NO:2), FIG. 2 (SEQ ID NO:4) or FIG. 3 (SEQ ID NO:6), and functional portions thereof. In a preferred embodiment, a primate MAdCAM or variant has an amino acid sequence which is at least about 55% similar, more preferably at least about 75% similar, and still more preferably at least about 90% similar, to a protein shown in FIG. 1 (SEQ ID NO:2), FIG. 2 (SEQ ID NO:4) or FIG. 3 (SEQ ID NO:6).

MAdCAM Structure

Figure 6:
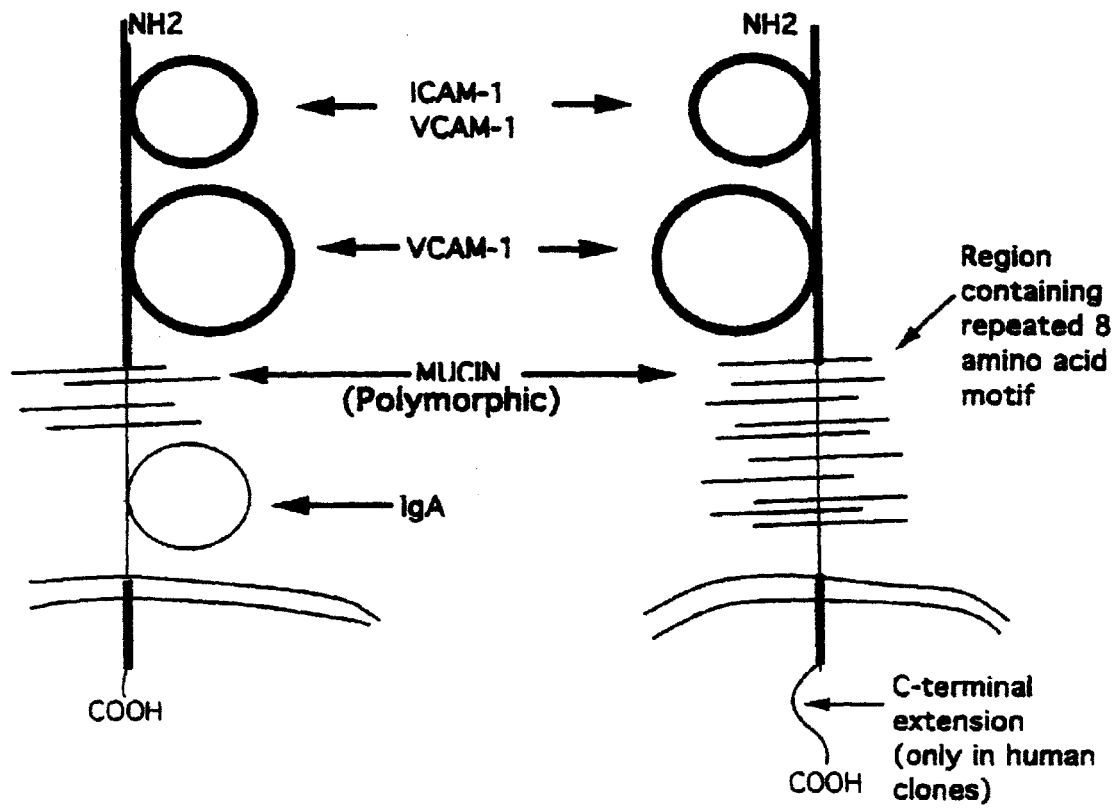
FIG. 6 is an illustration of the deduced domain structures of murine and human MAdCAM-1. The two N-terminal immunoglobulin domains bounded by disulfide bonds (indicated by loops) implicated in cell adhesion, transmembrane regions and a cytoplasmic tail are present in murine, macaque and human proteins. Human MAdCAM-1 has a longer cytoplasmic tail. An eight-amino acid repeat found in the mucin domain is present in 4 or 8 copies in human isoforms, but appears only once in the murine and macaque.

Murine MAdCAM-1, a member of the immunoglobulin supergene family, is a multi-domain molecule, comprising both immunoglobulin-related and mucin-like sequences (Briskin, M. J., et al., Nature, 363:461 (1993)). As indicated in FIG. 6, the murine form contains two amino-terminal immunoglobulin-like domains are homologous to domains of the Ig-like adhesion receptors, ICAM-1 and VCAM-1, and are implicated in integrin binding. The third (membrane proximal) immunoglobulin-like domain, while unrelated to adhesion receptors of this class, shares homology with another mucosal-related immunoglobulin superfamily member, IgA. In addition to the three immunoglobulin-like domains, murine MAdCAM-1 has a serine/threonine-rich mucin-like domain between the second and third Ig-like domains. These structural elements suggest that MAdCAM-1 facilitates more than one function in cell adhesion cascades, and recent studies of murine MAdCAM-1 support a role for MAdCAM-1 in both selectin and integrin binding (Moore, K. L., et al., J. Cell. Biol., 118:445 (1992); Bargatze, R. F., et al., Immunity, 3:99-108 (1995)). Also in this regard, it has been reported that murine MAdCAM-1, when expressed in mesenteric lymph nodes can present L-selectin binding carbohydrates associated with the peripheral node addressin epitope, MECA-79 (Berg, E. L., et al., Nature, 366:695 (1993)).

As described herein human and macaque MAdCAM-1 proteins have two immunoglobulin-like (Ig-like) domains which are homologous to the two amino-terminal immunoglobulin-like integrin binding domains of murine MAdCAM-1 (FIGS. 1-3, and 6). However, the similarity of sequences within the region homologous to the mucin/IgA domain of murine MAdCAM-1 is much less apparent. The membrane proximal regions of the human and macaque receptors exhibit considerable variation (as compared with each other or murine MAdCAM-1) with respect to the length of the mucin-like sequence and the lack of a membrane proximal Ig (IgA like) domain.

Two isoforms of human MAdCAM-1 have been identified which exhibited single amino acid polymorphisms and variation in the number of copies of a serine/threonine/proline rich repeat in the mucin region. These two isoforms appear to be encoded in genomic DNA, suggesting allelic variation and/or alternative processing of this sequence. These two isoforms may serve as alternative mechanisms of regulating α4β7 binding affinity and/or presenting carbohydrates for selectin binding. The presence of these Ig-like and mucin domains in primate MAdCAMs described herein is also consistent with role in selectin as well as integrin binding.

Recent domain swapping experiments in murine MAdCAM-1 have shown that, although domain one of MAdCAM-1 can weakly bind α4β7, adhesion is poor in the absence of strong integrin activation. The two amino-terminal Ig-like domains (which are similar to domains of ICAM-1 and VCAM-1) are sufficient for α4β7 binding activity in an activation independent manner comparable to that of wild type murine MAdCAM-1.

A short motif (GLDTSL) (SEQ ID NO:11) present in domain one of murine MAdCAM-1, is conserved and required for integrin binding in other Ig-like adhesion receptors, including of domain one of ICAM-1, ICAM-2, and ICAM-3, and domains 1 and 4 of VCAM-1 (Staunton, D. E., Cell, 52: 925-33 (1988); Staunton, D. E., et al., Nature, 339: 61 (1989); Osborn, L., et al., Cell, 59:1203 (1989); Fawcett, J., et al., Nature, 360:481 (1992)). This sequence, G-(I/L)-(D/E)-(T/S)-(P/S)-L (SEQ ID NO:12), is located between β sheets c and d of these integrin binding domains. The GLDTSL (SEQ ID NO:11) motif was found in the primate MAdCAMs characterized here.

Mutagenesis of E34 ($Glu^{34}$) in this motif of domain 1 of ICAM-1 (underlined above) and of D40 ($Asp^{40}$) in VCAM-1 (in bold face above) had profound effects on binding of LFA-1 and α4β1, respectively (Osborn, L., et al., J. Cell. Biol, 124:601-608 (1994); Renz, M. E., et al., J. Cell. Biol., 125: 1395-1406 (1994); Staunton, D. E., et al., Cell, 61:243-254 (1990); Vonderheide, R. H., et al., J. Cell. Biol., 125:215-222 (1994)). More recently, a fragment of VCAM-1 comprising the two N-terminal domains was subjected to crystallographic structure determination (Jones, E. Y., et al., Nature, 373:539-544 (1995); Wang, J-H, et al., Proc. Natl. Acad. Sci. USA., 92:5714-5718 (1995)). The conserved motif in VCAM-1 (QIDSPL) (SEQ ID NO:13) appears to be highly exposed on the N-terminal portion of the CD loop of the first Ig domain in a position that appears to be readily accessible to integrins.

A nucleotide substitution in this motif of murine MAdCAM-1, resulting in a change at amino acid 61 from leucine to arginine (L61→R61), abolishes MAdCAM-1 interactions with resting lymphocytes expressing α4β7. Therefore, murine MAdCAM-1 also requires this conserved amino acid motif, GLDTSL (SEQ ID NO:11), within the computer predicted CD loop of its N-terminal domain for binding its integrin ligand, α4β7.

Comparisons of human MAdCAM cDNA clones 4 and 20 (FIGS. 1 and 2) revealed that the amino-terminal 225 amino acids are identical in clones 4 and 20. This region comprises a predicted 18 amino acid hydrophobic leader or signal sequence, and two immunoglobulin-like domains. This region can be aligned with primate and murine MAdCAM-1, and displays the following conserved features: (1) a predicted signal peptide (identical in the human proteins, and similar to the macaque and murine signal peptides); (2) two pairs of cysteine residues in the first Ig-like domain, the cysteines of each pair being separated by 3 amino acids; (3) a sequence of nine a acids (which contains the "LDTSL" motif (SEQ ID NO:14)) in the predicted C-D loop of Ig-like domain 1, and is implicated as a general integrin recognition site (identical in each primate clone); and (4) an uncharacteristically large second immunoglobulin-like domain. The size of the second Ig-like domain, with approximately 70 amino acids between cysteine residues would classify it as a "V" (variable) type domain, in contrast with the C2 type (constant) domains which are more typically found in the Ig-like adhesion receptors (Hunkapiller, T., et al., *Adv. in Immunol.*, 44:1-62 (1989); Williams, A. F., et al., *Annu. Rev. Immunol.*, 6:381-405 (1988)). Within this domain is an extended C'-E loop containing an abundance of negatively charged residues, which is common to each primate, murine and human MAdCAM-1 clone characterized, but which is not seen in related adhesion receptors.

The next region found in clones 4 and 20 is analogous to the mucin domain of murine MAdCAM-1, due to a prevalence of serine, threonine and proline (69% for clone 4 and 76% for clone 20) residues (boxed in FIG. 1 and FIG. 2). This region, although similar in amino acid composition to murine MAdCAM-1, is highly divergent from murine MAdCAM-1. Therefore, selection for conservation of the integrin binding Ig-like domains appears greater than that of the mucin sequences. The human MAdCAM-1 domain is 71 amino acids long in clone 4, and 47 amino acids long in clone 20. This region also contains two polymorphisms: (1) a polymorphism at amino acid 240, which is proline (P) in clone 4 and serine (S) in clone 20; and (2) a polymorphism at amino acid 242, which is asparagine (N) in clone 4 and aspartate (D) in clone 20. In addition, the human mucin domains contain a repeat of 8 amino acids consisting of the sequence PPDTTS (Q/P)E (see e.g., amino acid residues 264-271 and 232-239, respectively, of SEQ ID NOS:1 and 2), which appears eight times in clone 4 and five times in clone 20.

Since the human mucin domain is highly repetitive, truncation of three repeats in clone 20 relative to clone 4 could be the result of processes such as alternative splicing or mutation (e.g., an aberrant recombination event) that maintain the reading frame, yielding a receptor that is functional with respect to integrin binding, and suggesting that some or all of the mucin sequences are dispensable for integrin binding. Consistently, it has been shown that Ig-like domains 1 and 2 of murine MAdCAM-1 are sufficient for activation-independent adhesion to α4β7, indicating that murine mucin sequences are dispensable for integrin binding. Also of interest in this regard, the macaque clone which was isolated lacks most of the repeat region.

The remaining C-terminal 110 amino acids are identical between clones 4 and 20: 47 amino acids precede a predicted hydrophobic transmembrane segment of 20 amino acids, which is followed by a cytoplasmic tail of 43 amino acids. The 47 amino acids immediately C-terminal to the mucin region are in a region corresponding to the IgA-like Ig domain of murine MAdCAM-1. Although the human and macaque proteins are similar in this region, they are divergent from murine MAdCAM-1. Compared with murine MAdCAM-1, the human proteins are 59 amino acids shorter in this region, and lack any characteristics of an Ig-like domain. The transmembrane domains of all the receptors are similar, but the cytoplasmic tail is considerably longer (43 amino acids) in human (26 in primate and 20 in the mouse) MAdCAM-1.

Method of Producing Recombinant Proteins

Another aspect of the invention relates to a method of producing a primate MAdCAM or variant (e.g., portion) thereof. Recombinant protein can be obtained, for example, by the expression of a recombinant DNA molecule encoding a primate MAdCAM or variant thereof in a suitable host cell, for example.

Constructs suitable for the expression of a primate MAdCAM or variant thereof are also provided. The constructs can be introduced into a suitable host cell, and cells which express a recombinant primate MAdCAM or variant thereof, can be produced and maintained in culture. Such cells are useful for a variety of purposes, and can be used in adhesion assays (e.g., in an assay to screen for ligands and/or candidate inhibitors of MAdCAM-mediated adhesion), in the production of protein for characterization, isolation and/or purification, (e.g., affinity purification), and as immunogens, for instance. Suitable host cells can be procaryotic, including bacterial cells such as *E. coli*, *B. subtilis* and or other suitable bacteria, or eucaryotic, such as fungal or yeast cells (e.g., *Pichia pastoris*, Aspergillus species, *Saccharomyces cerevisiae, Schizosaccharomyces pombe, Neurospora crassa*), or other lower eucaryotic cells, and cells of higher eucaryotes such as those from insects (e.g., Sf9 insect cells) or mammals (e.g., Chinese hamster ovary cells (CHO), COS cells, HuT 78 cells, 293 cells). (See, e.g., Ausubel, F. M. et al., eds. *Current Protocols in Molecular Biology*, Greene Publishing Associates and John Wiley & Sons Inc., (1993)). In one embodiment, host cells capable of expressing membrane-bound mature protein are used. In another embodiment, host cells capable of secreting a soluble MAdCAM (e.g., soluble MAdCAM, such as MAdCAM lacking the C-terminal transmembrane region and cytoplasmic tail).

Host cells which produce a recombinant primate MAdCAM or variants thereof can be produced as follows. For example, a nucleic acid encoding all or part of the coding sequence for the desired protein can be inserted into a nucleic acid vector, e.g., a DNA vector, such as a plasmid, virus or other suitable replicon for expression. A variety of vectors are available, including vectors which are maintained in single copy or multiple copy, or which become integrated into the host cell chromosome.

The transcriptional and/or translational signals of a a MAdCAM-1 gene can be used to direct expression. Alternatively, suitable expression vectors for the expression of a nucleic acid encoding all or part of the coding sequence of the desired protein are available. Suitable expression vectors can contain a number of components, including, but not limited to one or more of the following: an origin of replication; a selectable marker gene; one or more expression control elements, such as a transcriptional control element (e.g., a promoter, an enhancer, terminator), and/or one or more translation signals; a signal sequence or leader sequence for membrane targeting or secretion (of primate origin or from a heterologous primate or non-primate species). In a construct, a signal sequence can be provided by the vector, the primate MAdCAM coding sequence, or other source.

A promoter is provided for expression in a suitable host cell. Promoters can be constitutive or inducible. In the vectors, the promoter is operably linked to a nucleic acid encoding the primate MAdCAM or variant thereof, and is capable of directing expression of the encoded polypeptide. A variety of suitable promoters for procaryotic (e.g., lac, tac, T3, T7 promoters for *E. coli*) and eucaryotic (e.g., yeast alcohol dehydrogenase (ADH1), SV40, CMV) hosts are available.

In addition, the expression vectors typically comprise a selectable marker for selection of host cells carrying the vector, in the case of replicable expression vector, an origin or replication. Genes encoding products which confer antibiotic or drug resistance are common selectable markers and may be used in procaryotic (e.g., β-lactamase gene (ampicillin resistance), Tet gene for tetracycline resistance) and eucaryotic cells (e.g., neomycin (G418 or geneticin), gpt (mycophenolic acid), ampicillin, or hygromycin resistance genes). Dihydrofolate reductase marker genes permit selection with methotrexate in a variety of hosts. Genes encoding the gene product of auxotrophic markers of the host (e.g., LEU2, URA3, HIS3) are often used as selectable markers in yeast. Use of viral (e.g., baculovirus) or phage vectors, and vectors which are capable of integrating into the genome of the host cell, such as retroviral vectors, are also contemplated. The present invention also relates to cells carrying these expression vectors.

For example, a nucleic acid encoding a primate MAdCAM or variant thereof can be incorporated into the vector, operably linked to one or more expression control elements, and the construct can be introduced into host cells which are maintained under conditions suitable for expression, whereby the encoded polypeptide is produced. The construct can be introduced into cells by a method appropriate to the host cell selected (e.g., transformation, transfection, electroporation, infection). For production of a protein, host cells comprising the construct are maintained under conditions appropriate for expression, (e.g., in the presence of inducer, suitable media supplemented with appropriate salts, growth factors, antibiotic, nutritional supplements, etc.). The encoded protein (e.g., human MAdCAM-1) can be isolated from the host cells or medium.

Fusion proteins can also be produced in this manner. For example, some embodiments can be produced by the insertion of a primate MAdCAM cDNA or portion thereof into a suitable expression vector, such as Bluescript®II SK+/− (Stratagene), pGEX-4T-2 (Pharmacia), pcDNA-3 (Invitrogen) and pET-15b (Novagen). The resulting construct is then introduced into a suitable host cell for expression. Upon expression, fusion protein can be isolated or purified from a cell lysate by means of a suitable affinity matrix (see e.g., *Current Protocols in Molecular Biology* (Ausubel, F. M. et al., eds., Vol. 2, Suppl. 26, pp. 16.4.1-16.7.8 (1991)). In addition, affinity labels provide a means of detecting a fusion protein. For example, the cell surface expression or presence in a particular cell fraction of a fusion protein comprising an antigen or epitope affinity label can be detected by means of an appropriate antibody.

Nucleic Acids, Constructs and Vectors

The present invention relates to isolated and/or recombinant (including, e.g., essentially pure) nucleic acids having sequences which encode a primate MAdCAM or variant thereof as described herein.

Nucleic acids referred to herein as "isolated" are nucleic acids separated away from the nucleic acids of the genomic DNA or cellular RNA of their source of origin (e.g., as it exists in cells or in a mixture of nucleic acids such as a library), and may have undergone further processing. "Isolated" nucleic acids include nucleic acids obtained by methods described herein, similar methods or other suitable methods, including essentially pure nucleic acids, nucleic acids produced by chemical synthesis, by combinations of biological and chemical methods, and recombinant nucleic acids which are isolated (see e.g., Daugherty, B. L. et al., *Nucleic Acids Res.*, 19(9):2471-2476 (1991); Lewis, A. P. and J. S. Crowe, *Gene*, 101: 297-302 (1991)). Nucleic acids referred to herein as "recombinant" are nucleic acids which have been produced by recombinant DNA methodology, including those nucleic acids that are generated by procedures which rely upon a method of artificial recombination, such as the polymerase chain reaction (PCR) and/or cloning into a vector using restriction enzymes. "Recombinant" nucleic acids are also those that result from recombination events that occur through the natural mechanisms of cells, but are selected for after the introduction to the cells of nucleic acids designed to allow and make probable a desired recombination event.

In one embodiment, the nucleic acid or portion thereof encodes a protein or polypeptide having at least one property, activity or function characteristic of a primate MAdCAM (as defined herein), such as binding function (e.g., the ability to bind an α4β7 integrin), and/or cellular adhesion molecule function (e.g., the ability to mediate cellular adhesion such as α4β7-dependent adhesion in vitro and/or in vivo), and/or an immunological property as defined herein.

The present invention also relates more specifically to isolated and/or recombinant nucleic acids or a portion thereof having sequences which encode human or macaque MAdCAM-1 or variant thereof.

The invention further relates to isolated and/or recombinant nucleic acids that are characterized by:
  (1) their ability to hybridize to (a) a nucleic acid encoding a primate MAdCAM, such as a nucleic acid having a nucleotide sequence as set forth or substantially as set forth in FIG. 1 (SEQ ID NO:1), FIG. 2 (SEQ ID NO:3), or FIG. 3 (SEQ ID NO:5); (b) the complement of any one of (a); or (c) portions of either of the foregoing (e.g., a portion comprising the open reading frame); or
  (2) by their ability to encode a polypeptide having the amino acid sequence of a primate MAdCAM (e.g., SEQ ID NO:2, SEQ ID NO:4, or SEQ ID NO:6); or
  (3) by both characteristics.

In one embodiment, the nucleic acid shares at least about 50% nucleotide sequence similarity to any one of the nucleotide sequences shown in FIG. 1, FIG. 2, or FIG. 3 (SEQ ID NO:1, 3, or 5, respectively) or to one of the MAdCAM coding regions thereof. More preferably, the nucleic acid shares at least about 75% nucleotide sequence similarity, and still more preferably, at least about 90% nucleotide sequence similarity, to any one of the sequences shown in FIG. 1, FIG. 2, or FIG. 3 (SEQ ID NO:1, 3, or 5, respectively) or to one of the MAdCAM coding regions thereof.

Isolated and/or recombinant nucleic acids meeting these criteria comprise nucleic acids having sequences identical to sequences of naturally occurring primate MAdCAMs or variants of the naturally occurring sequences. Such variants include mutants differing by the addition, deletion or substitution of one or more residues, modified nucleic acids in which one or more residues are modified (e.g., DNA or RNA analogs), and mutants comprising one or more modified residues.

Nucleic acids of the present invention, including those which hybridize to a selected nucleic acid as described above, can be detected or isolated under high stringency conditions or moderate stringency conditions, for example. "High stringency conditions" and "moderate stringency conditions" for nucleic acid hybridizations are explained at pages 2.10.1-2.10.16 (see particularly 2.10.8-11) and pages 6.3.1-6 in *Current Protocols in Molecular Biology* (Ausubel, F. M. et al., eds., Vol. 1, Suppl. 26, 1991), the teachings of which are hereby incorporated by reference. Factors such as probe length, base composition, percent mismatch between the hybridizing sequences, temperature and ionic strength influence the stability of nucleic acid hybrids. Thus, high or moderate stringency conditions can be determined empirically, and depend in part upon the characteristics of the known nucleic acid (e.g., DNA) and the other nucleic acids to be assessed for hybridization thereto.

Isolated and/or recombinant nucleic acids that are characterized by their ability to hybridize (e.g. under high or moderate stringency conditions) to (a) a nucleic acid encoding a primate MAdCAM (for example, those nucleic acids depicted in FIG. 1 (SEQ ID NO:1), FIG. 2 (SEQ ID NO:3), and FIG. 3 (SEQ ID NO:5), (b) the complement of such nucleic acids, (c) or a portion thereof, can also encode a protein or polypeptide having at least one property, activity or function characteristic of a primate MAdCAM (as defined herein), such as binding function (e.g., the ability to bind an $\alpha 4\beta 7$ integrin), and/or cellular adhesion molecule function (e.g., the ability to mediate cellular adhesion such as $\alpha 4\beta 7$-dependent adhesion in vitro and/or in vivo), and/or an immunological property as defined herein. Preferred nucleic acids have lengths of at least about 40 nucleotides, more preferably at least about 50, and still more preferably at least about 75 nucleotides.

The binding function of a primate MAdCAM or variant thereof which is encoded by a nucleic acid of the present invention can be detected by standard assays for ligand binding (e.g., assays which monitor formation of a complex between isolated and/or recombinant MAdCAM and an $\alpha 4\beta 7$ integrin) or standard adhesion assays (e.g., in which adhesion between a first cell expressing a recombinant primate MAdCAM, and a second cell bearing an $\alpha 4\beta 7$ integrin is monitored), or other suitable methods. Binding and/or adhesion assays or other suitable methods can also be used in procedures for the identification and/or isolation of nucleic acids which encode a polypeptide of the present invention (see e.g., Example 1). The antigenic properties of proteins or polypeptides encoded by nucleic acids of the present invention can be determined by immunological methods employing antibodies that bind to a primate MAdCAM, such as immunoblotting, immunoprecipitation and immunoassay (e.g., radioimmunoassay, ELISA).

Nucleic acids of the present invention can be used in the production of proteins or polypeptides. For example, a nucleic acid (e.g., DNA) encoding a primate MAdCAM can be incorporated into various constructs and vectors created for further manipulation of sequences or for production of the encoded polypeptide in suitable host cells as described above.

A further embodiment of the invention is antisense nucleic acid, which is complementary, in whole or in part, to a target molecule comprising a sense strand, and can hybridize with the target molecule. The target can be DNA, or its RNA counterpart (i.e., wherein T residues of the DNA are U residues in the RNA counterpart). When introduced into a cell, antisense nucleic acid can inhibit the expression of the gene encoded by the sense strand. Antisense nucleic acids can be produced by standard techniques.

In a particular embodiment, the antisense nucleic acid is wholly or partially complementary to and can hybridize with a target nucleic acid, wherein the target nucleic acid can hybridize to a nucleic acid having the sequence of the complement of the top strand shown in FIG. 1 (SEQ ID NO:1), FIG. 2 (SEQ ID NO:3), or FIG. 3 (SEQ ID NO:5). For example, antisense nucleic acid can be complementary to a target nucleic acid having the sequence shown as the top strand of the open reading frame in FIG. 1 (SEQ ID NO:1), FIG. 2 (SEQ ID NO:3), or FIG. 3 (SEQ ID NO:5), or to a portion thereof sufficient to allow hybridization. In another embodiment, the antisense nucleic acid is wholly or partially complementary to and can hybridize with a target nucleic acid which encodes a primate MAdCAM.

The nucleic acids can also be used as probes, (e.g., in in situ hybridization) to assess associations between inflammatory bowel disease (IBD) (or other conditions) and increased expression of primate MAdCAM in affected tissues.

As described in the Examples, a cDNA clone encoding macaque MAdCAM-1 was isolated by expression cloning, and the cDNA was used as a probe to screen a human cDNA library. Two distinct nucleic acids encoding human MAdCAM-1 were isolated and characterized. Additional human, macaque or other primate genes or cDNAs can be obtained. For example, the genes described here, or sufficient portions thereof, whether isolated and/or recombinant or synthetic, can be used as probes or primers to detect and/or recover additional nucleic acids encoding primate MAdCAMs or variants thereof from a suitable source such as a primate genomic or cDNA library, according to methods described herein or other suitable methods (e.g., by hybridization, PCR, expression cloning or other suitable techniques).

In one embodiment, nucleic acids encoding primate MAdCAM are producible by methods such as PCR amplification. For example, appropriate primers (e.g., a pair of primers or nested primers) can be designed which comprise a sequence which is complementary or substantially complementary to a portion of a primate MAdCAM cDNA described herein. For instance, primers complementary to the 5'- or 3'-ends of the coding sequence and/or flanking the coding sequence can be designed. Such primers can be used in a polymerase chain reaction with a suitable template nucleic acid to obtain nucleic acid encoding primate MAdCAM, for example. Suitable templates include e.g., constructs described herein such as pcD3PMAd, pcD3HuMAd-4 or pcD3HuMAd-20), a cDNA library or another suitable source of primate (e.g., human) cDNA or genomic DNA. Primers can contain portions complementary to flanking sequences of the construct selected as template as appropriate.

Additional genes or cDNAs can be used to express primate MAdCAM, with utilities corresponding to those described herein, can be used in the production of constructs, host cells, and antibodies using methods described herein. The approaches described herein, including, but not limited to, the approaches used to isolate and manipulate macaque and human MAdCAM-1, to construct vectors and host strains, and to produce and use the proteins, to produce antibodies, etc., can be applied to other primates.

Therapeutic Methods and Compositions

The invention further relates to the discovery that diseases associated with leukocyte recruitment to the gastrointestinal tract, such as IBD, or other mucosal tissues can be treated by inhibiting MAdCAM binding to the $\alpha 4\beta 7$ integrin or triggering of $\alpha 4\beta 7$-mediated cellular responses. Compounds or agents which inhibit binding include antibodies or antigen binding fragments thereof which bind MAdCAM and/or the $\alpha 4\beta 7$ integrin. Antibodies which can be used in the method include recombinant or non-recombinant polyclonal, monoclonal, chimeric, humanized and/or anti-idiotypic antibodies.

The present invention also provides antibodies which (1) can bind a "primate MAdCAM" in vitro and/or in vivo; and/ or (2) can inhibit an activity or function characteristic of a "primate MAdCAM", such as binding function (e.g., the ability to bind an α4β7 integrin) and/or cellular adhesion molecule function (e.g., the ability to mediate cellular adhesion such as α4β7-dependent adhesion in vitro and/or in vivo). Such antibodies include antibodies which can bind a human or macaque MAdCAM encoded by cDNA clone 4, cDNA clone 20 or cDNA clone 31D. Also encompassed are antibodies which can bind a naturally occurring or endogenous primate MAdCAM (e.g., human MAdCAM). Preferably the antibodies are capable of selective binding of primate MAdCAM in vitro and/or in vivo (e.g., bind selectively to primate MAdCAM expressed in mucosal tissue and/or spleen (e.g., as assessed immunohistologically)).

In one embodiment, the antibodies can bind primate MAdCAM and inhibit binding of "primate MAdCAM" to an α4β7 integrin (e.g., human), thereby inhibiting cellular adhesion mediated by MAdCAM, preferably selectively. Such an antibody can inhibit α4β7-dependent cellular adhesion to cells bearing an α4β7 integrin, such as leukocytes (especially lymphocytes such as T or B cells) in vitro and/or in vivo. For example, eleven hybridomas were identified which produced antibodies which specifically inhibit the adhesion of RPMI 8866 cells to MAdCAM-1 (Example 2, hybridomas designated 10G4, 8C1, 10G3, 9G12, 9E4, 7H12, 10F2, 10A6, 1E5, 2F5, 7G11). Thus, antibodies which can inhibit cellular adhesion of cells bearing an α4β7 integrin to vascular endothelial cells in mucosal tissues, including gut-associated tissues or lymphoid organs are encompassed by the antibodies of the present invention.

Preferably, the antibodies can bind a primate MAdCAM with high affinity (for example, a Ka in the range of about 1-10 nM, or a Kd in the range of about $1 \times 10^{-8}$ to $1 \times 10^{-10}$ mol$^{-1}$).

The antibodies of the present invention are useful in a variety of applications, including processes, research, diagnostic and therapeutic applications. For instance, they can be used to isolate and/or purify primate MAdCAM or variants thereof (e.g., by affinity purification or other suitable methods), and to study MAdCAM structure (e.g., conformation) and function.

The antibodies of the present invention can also be used to modulate MAdCAM function in diagnostic (e.g., in vitro) or therapeutic applications. For instance, antibodies can act as inhibitors of to inhibit (reduce or prevent) binding function and/or cellular adhesion molecule function of a primate MAdCAM as described.

In addition, antibodies of the present invention can be used to detect and/or measure the level of a primate MAdCAM in a sample (e.g., tissues or body fluids, such as an inflammatory exudate, blood, serum, bowel fluid, or on cells transfected with a nucleic acid of the present invention). For example, a sample (e.g., tissue and/or fluid) can be obtained from a primate and a suitable immunological method can be used to detect and/or measure primate MAdCAM levels, including methods such as enzyme-linked immunosorbent assays (ELISA), including chemiluminescence assays, radioimmunoassay, and immunohistology. In one embodiment, a method of detecting a selected primate MadCAM in a sample is provided, comprising contacting a sample with an antibody which binds an isolated primate MAdCAM under conditions suitable for specific binding of said antibody to the selected primate MAdCAM, and detecting antibody-MAdCAM complexes which are formed.

In an application of the method, antibodies reactive with a primate MAdCAM-1 can be used to analyze normal versus inflamed tissues in human and non-human primates for primate MAdCAM reactivity and/or expression (e.g., immunohistologically). Thus, the antibodies of the present invention permit immunological methods of assessment of expression of primate (e.g., human MAdCAM-1) in normal versus inflamed tissues, through which the presence of disease, disease progress and/or the efficacy of anti-primate MAdCAM-1 therapy in inflammatory disease can be assessed.

Monoclonal antibodies that bind MAdCAM or α4β7 have been described. For example, MECA 367 is an anti-MAdCAM antibody of the IgG2a subtype and is described in Gallatin et al., *Nature*, 304:30 (1983) and Michie et al., *Am. J. Pathol.* 143:1688-1698 (1993). ACT-1 is a monoclonal antibody which binds the α4β7 integrin (Lazarovits et al., *Journal of Immunology*, 133:1857 (1984) and Schweighoffer et al., *Journal of Immunology*, 151:717-729 (1993)). FIB 21 binds the β7 chain is described and characterized in Berlin et al., *Cell* 74:184-195 (1993); Andrew, D. P. et al., *J. Immunol.* 153:3847-3861 (1994)).

Other polyclonal or monoclonal antibodies, such as antibodies which bind to the same or similar epitopes as the antibodies described above, can be made according to methods described herein, methods known in the art or other suitable methods (such as Kohler et al., *Nature*, 256:495-497 (1975), Harlow et al., 1988, Antibodies: A Laboratory Manual, (Cold Spring Harbor, N.Y.) or Current Protocols in Molecular Biology, Vol. 2 (Supplement 27, Summer '94), Ausubel et al., Eds. (John Wiley & Sons: New York, N.Y.), Chapter 11 (1991)). Antibodies can also be produced which can compete with any one of the antibodies produced by the hybridoma cell lines designated 10G4, 8C1, 10G3, 9G12, 9E4, 7H12, 10F2, 10A6, 1E5, 2F5, or 7G11 for binding to a cell bearing an α4β7 integrin, preferably human α4β7 integrin.

For example, antibodies can be raised against an appropriate immunogen in a suitable mammal (e.g., a mouse, rat, rabbit or sheep). Immunogens include, for example, MAdCAM, α4β7, or immunogenic fragments thereof. For example, a primate MAdCAM or a variant thereof can be produced and used as an immunogen to raise antibodies in a suitable immunization protocol.

Antibody-producing cells (e.g., a lymphocyte) can be isolated from, for example, the lymph nodes or spleen of an immunized animal. The cells can then be fused to a suitable immortalized cell (e.g., a myeloma cell line), thereby forming a hybridoma. Fused cells can be isolated employing selective culturing techniques. Cells which produce antibodies with the desired specificity can be selected by a suitable assay (e.g., ELISA) (see e.g., Example 2).

In one embodiment, the immunogen can be an antibody which binds, for example, MAdCAM, α4β7, or immunogenic fragments thereof. The antibody raised thereby can be an anti-idiotypic antibody, which can also be used in the present invention (U.S. Pat. No. 4,699,880).

Single chain antibodies, and chimeric, humanized or primatized (CDR-grafted or resurfaced, such as, according to EP 0,592,406; Padlan et al., Apr. 13, 1994) antibodies, as well as chimeric or CDR-grafted single chain antibodies, comprising portions derived from different species, can also be used in the invention. The various portions of these antibodies can be joined together chemically by conventional techniques, or can be prepared as a contiguous protein using genetic engineering techniques. For example, nucleic acids encoding a chimeric or humanized chain can be expressed to produce a contiguous protein. See, e.g., Cabilly et al., U.S. Pat. No. 4,816,567; Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; and Winter, European Patent No. 0,239,400 B1. See also, Newman, R. et al., *BioTechnology*, 10:1455-1460 (1992), regarding primatized antibody, and Ladner et al., U.S. Pat. No. 4,946,778 and Bird, R. E. et al., *Science*, 242:423-426 (1988)) regarding single chain antibodies.

In addition, functional fragments of antibodies, including fragments of chimeric, humanized, primatized or single chain antibodies, can also be produced. Functional fragments of the foregoing antibodies retain at least one binding function of the full-length antibody from which they are derived and, preferably, retain the ability to inhibit interaction. For example, antibody fragments capable of binding to the α4β7 integrin, MAdCAM or portion thereof include, but are not limited to, Fv, Fab, Fab' and F(ab')$_2$ fragments. Such fragments can be produced by enzymatic cleavage or by recombinant techniques. For instance, papain or pepsin cleavage can generate Fab or F(ab')$_2$ fragments, respectively. Alternatively, antibodies can be produced in a variety of truncated forms using antibody genes in which one or more stop codons has been introduced upstream of the natural stop site. For example, a chimeric gene encoding a F(ab')$_2$ heavy chain portion can be designed to include DNA sequences encoding the CH$_1$ domain and hinge region of the heavy chain.

Antibodies and antigen binding fragments thereof which can be used in the claimed method include antibodies which bind to MAdCAM and/or α4β7, such as anti-β7 chain antibodies. For example, antibodies from the group including FIB 21, FIB 30, FIB 504 and ACT-1 and mixtures thereof can be administered. Alternatively or in addition, antigen fragments of these antibodies can be administered.

Compounds which inhibit the binding of MAdCAM and the α4β7 integrin can be administered according to the claimed method in the treatment of diseases which are associated with leukocyte (such as lymphocyte or monocyte) recruitment to the gastrointestinal tract or other tissues as a result of binding of leukocytes to gut-associated endothelium expressing the molecule MAdCAM. Diseases which can be treated accordingly include inflammatory bowel disease, such as ulcerative colitis, Crohn's disease, Celiac disease (nontropical Sprue), enteropathy associated with seronegative arthropathies, microscopic or collagenous colitis, eosinophilic gastroenteritis, or pouchitis resulting after proctocolectomy and ileoanal anastomosis. In one embodiment, more than one monoclonal antibody which inhibits the binding of leukocytes to endothelial MAdCAM is administered. Alternatively, a monoclonal antibody which inhibits the binding of leukocytes to endothelial ligands is administered in addition to an anti-MAdCAM or anti-β7 antibody. For example, an antibody that inhibits the binding of leukocytes to an endothelial ligand other than MAdCAM, such as an anti-ICAM-1 or anti-VCAM-1 antibody can also be administered. In another embodiment, an additional pharmacologically active ingredient (such as a steroid) can be administered in conjunction with the antibody of the present invention.

A variety of routes of administration are possible including, but not necessarily limited to parenteral (e.g., intravenous, intraarterial, intramuscular, subcutaneous injection), oral (e.g., dietary), topical, inhalation (e.g., intrabronchial, intranasal or oral inhalation, intranasal drops), or rectal, depending on the disease or condition to be treated. Parenteral administration is a preferred mode of administration.

Formulation of a compound to be administered will vary according to the route of administration selected (e.g., solution, emulsion, capsule). An appropriate composition comprising the compound to be administered can be prepared in a physiologically acceptable vehicle or carrier. For solutions or emulsions, suitable carriers include, for example, aqueous or alcoholic/aqueous solutions, emulsions or suspensions, including saline and buffered media. Parenteral vehicles can include sodium chloride solution, Ringer's dextrose, dextrose and sodium chloride, lactated Ringer's or fixed oils. Intravenous vehicles can include various additives, preservatives, or fluid, nutrient or electrolyte replenishers (See, generally, *Remington's Pharmaceutical Science*, 16th Edition, Mack, Ed. 1980). For inhalation, the compound is solubilized and loaded into a suitable dispenser for administration (e.g., an atomizer, nebulizer or pressurized aerosol dispenser).

The compound is administered in an amount which will inhibit binding of MAdCAM to the α4β7 integrin. The compounds can be administered in a single dose or multiple doses. The dosage can be determined by methods known in the art and is dependent, for example, upon the individual's age, sensitivity, tolerance and overall well-being. Suitable dosages can be from 0.1-1.0 mg/kg body weight per treatment.

EXEMPLIFICATION

The present invention will now be illustrated by the following Examples, which are not intended to be limiting in any way.

Introduction

A functional expression approach was used, whereby cells transfected with cDNAs which conferred the ability to adhere to a target lymphocyte cell line expressing high levels of the MAdCAM-1 ligand (α4β7) were identified and the cDNAs recovered. As human tissue sources were scarce, a primate equivalent of MAdCAM-1 was first identified.

For expression cloning, a primate cDNA expression library, derived from mesenteric lymph nodes of a macaque, was made in a eukaryotic expression vector pRSVsport (from Gibco/BRL). A high efficiency transfection system using the CHO/P cell line (Heffernan, M. and J. D. Dennis, *Nucleic Acids Res.*, 19: 85-92 (1991)) was used. The library was separated and individual pools (representing approximately 1,500 clones) were transfected in wells of 24 well tissue culture plates. Cell adhesion assays were performed to identify cDNAs which conferred an adhesive phenotype on T and B cell lines expressing the β4β7 integrin, a known ligand for MAdCAM-1. Adhesion was identified microscopically by resetting of the T and B cell lines on the transfected cells. A pool conferring the desired phenotype was subfractionated until a single full-length cDNA clone designated clone 31D was identified. DNA sequencing of the amino-terminal portion of the cDNA revealed homology of the macaque clone to murine MAdCAM-1 (Briskin, M. J., et al, *Nature* (Lond.), 363:461-464 (1993)) at both the protein and nucleic acid level.

When introduced into CHO/P cells by transient transfection, the cDNA insert obtained from clone 31D directed the expression of a protein which could mediate binding to two cell lines which express α4β7: (1) TK1, a murine T cell lymphoma (Butcher, E. C., et al., *Eur. J. of Immunol.*, 10: 556-561 (1980)); and (2) RPMI 8866, a human B cell lymphoma (Erle, D. J., et al., *J. Immunol.*, 153: 517-528 (1994)). Binding of TK1 cells to cells transfected with the macaque cDNA could be blocked by antibodies to either the α4 (MAb PS/2) or the β7 (MAb FIB 504) integrins, and binding of RPMI 8866 to CHO/P cells transiently transfected with macaque cDNA (clone 31D in pSV-SPORT) was blocked by the anti-α4β7 MAb, ACT-1. In control experiments, a cDNA encoding human VCAM-1 failed to bind the RPMI 8866 human B cell line. Jurkat cells, a T cell line which expresses α4β1 and not α4β7, was shown to bind VCAM-1, but failed to bind transfectants expressing macaque cDNA.

The cDNA encoding a primate (macaque) homolog of murine MAdCAM-1 was used as a probe to obtain a clone encoding a human homolog by hybridization. To obtain a human MAdCAM-1 clone, two cDNA libraries, one derived from histologically normal human mesenteric lymph node (MLN) and one derived from an inflamed MLN lymph node from a patient with Crohn's disease, were constructed in the λZiplox phage vector from Gibco/BRL. cDNA from the macaque clone was used to screen these libraries. Two different human cDNA clones of similar size were isolated. These clones each appeared to be full-length by preliminary sequence analysis. Analysis of human, as well as macaque, MAdCAM-1 cDNAs indicates that each of the encoded proteins has a predicted hydrophobic leader sequence (underlined in FIGS. 1-3), with the remaining portions of the proteins corresponding to predicted mature human or macaque MAdCAM-1, respectively.

To assess function, the human cDNA inserts were subcloned into the pCDNA3 expression vector (Invitrogen) and transient expression assays were used to demonstrate function. The human cDNAs can be expressed as functional proteins, and are capable of mediating specific binding to cells expressing α4β7. Accordingly, these two human cDNA clones are designated as human MAdCAM-1 cDNAs.

Stable transfectants of both the primate and human cDNAs were generated in a mouse pre-B cell line, L1-2 and CHO cells. L1-2 transfectants were used to immunize mice and generate monoclonal antibodies against human MAdCAM-1. Antibodies capable of inhibiting the interaction between MAdCAM-1 and α4β7 were identified. The production of blocking antibodies directed against human MAdCAM-1 is a significant advance, as previous attempts to produce such blocking antibodies having cross-reactivity with the human homolog using murine MAdCAM-1 have failed.

Example 1

Cloning of Macaque and Human MAdCAM-1 cDNAs

RNA Isolation and Selection of Message

Total RNA was isolated from (a) primate (macaque) mesenteric lymph nodes (MLN); (b) histologically normal human mesenteric lymph nodes; (c) human mesenteric lymph nodes (inflamed ileal nodes) from a patient with Crohn's disease; and (d) tissue culture cells by use of the CSTFA™ (cesium trifluoroacetate) reagent (Pharmacia; Cat. #17-087-02). Total RNA from mesenteric lymph node was obtained from two species of macaque (*Macaca fascicularis*, and *Macaca mulatta*), and was combined prior to isolation of poly-A RNA. Tissue was first snap frozen in liquid nitrogen and subjected to dounce homogenization in a solution consisting of 5.5 M guanidinium isothiocyanate, 25 mM sodium citrate, 0.5% sodium laurel sarcosine and 0.2 M 2-mercaptoethanol, while tissue culture cells ($1-5 \times 10^8$) were washed once in phosphate buffered saline (PBS) and homogenized by pipetting. A clarified lysate was then layered on a cushion of CsTFA and total RNA was pelleted by centrifugation for 20 hours at 30,000 RPM.

mRNA was selected by the polyATract mRNA isolation system from Promega. The system uses a biotinylated oligo (dT) primer to hybridize (in solution) to poly A tails of eukaryotic messages. The hybrids were captured and washed at high stringency using streptavidin coupled to paramagnetic particles and a magnetic separation stand. mRNA was selected by a single purification in this system and the yields ranged from 1-2% of the total RNA yield. The integrity of both the total and mRNA was analyzed by gel electrophoresis and ethidium bromide staining.

cDNA Synthesis cDNA was synthesized using the Superscript™ lambda system (Cat. #18256-016) in conjunction with either the λZiplox™ vector (GibcoBRL, Cat. #19643-014) in the case of the human libraries, or the pSV-SPORT-1 vector (GibcoBRL, Cat. #15388-010) in the case of the macaque library. The following modifications from the standard protocol were made. cDNA was labeled only in the first or second strand (but not both) with $\alpha^{32}$P-dCTP and estimates of quantity were made by inspection of ethidium bromide staining of aliquots of cDNA fractions.

DNA Sequencing

The entire macaque and human MAdCAM-1 cDNAs were first isolated in the library vectors pSV-SPORT-1 and pZL1 (rescued from λZiplox™), respectively. Based on restriction mapping, fragments were subcloned into Bluescript® vectors (Stratagene) to facilitate sequencing from internal regions of the cDNAs. After sequence analysis of these clones, oligonucleotide primers were made to complete the sequence. Overlapping sequence of both strands was obtained. Sequence analysis utilized the Sequenase™ 7-deaza-dGTP DNA sequencing kit with sequenase version 2.0 T7 DNA polymerase (United States Biochemical) and $^{35}$S-dCTP (Amersham Life Science and New England Nuclear). The delta TAQ sequencing kit (USB) and gamma $^{32}$P-ATP (Amersham) G-C rich sequence were also used for G-C rich sequences.

Sequences were entered and analyzed using the Lasergene system (DNASTAR, Inc.). Nucleotide sequence alignments were performed by the Clustal method with Weighted residue weight table, using a gap penalty of 10 and a gap length penalty of 10, and default parameters (Pairwise alignment parameters were: ktuple=2, gap penalty=5, window=4, and diagonals saved=4).

Amino acid sequence alignments were performed by the Clustal method with the PAM250 residue weight table, using a gap penalty of 10 and a gap length penalty of 10 and default parameters (Pairwise alignment parameters were: ktuple=1, gap penalty=3, window=4, and diagonals saved=5).

Preparation of Macaque Expression Library

The size fractionation procedure was also modified slightly for construction of the macaque expression library to ensure large (>1.5 kb) inserts. After one round of fractionation, only the first (largest) fraction of cDNA was saved and the remaining fractions were pooled and subjected to a subsequent round of fractionation. The top fraction from the next round was pooled with the top fraction from the previous round and the second fraction from this round was also used. These two fractions were precipitated and put into ligations with the pSV-SPORT-1 vector and a fraction of each ligation was transformed into electrocompetent DH10B bacteria (Gibco) to estimate both the titer of the library and the average insert size. Estimates from ligation of only top largest cDNA fraction revealed the potential of making up 2.4 million independent clones with an average insert size of 1.9 kb and a median size of 2 kb.

The actual library screened consisted of 150,000 independent clones which were plated at a density of 1,500 clones/plate on 100 LB agar plates (to generate 100 pools of 1,500 clones/pool) with ampicillin at 50 µg/ml and grown overnight at 37° C. For purification of individual pools, each plate was overlayed with approximately 2 ml of Luria broth (LB), and the colonies were scraped off of each plate with a standard tissue culture cell scraper, and bacterial suspensions were transferred to microfuge tubes. Prior to purification, a glycerol stock was generated from each pool. Plasmid DNAs were purified using QIAprep spin columns (QIAGEN) according to manufacturer's instructions.

Transfections

CHO/P cells (Heffernan, M. and J. D. Dennis, *Nucleic Acids Res.*, 19:85-92 (1991)) were seeded into 24 well plates approximately 24 hours prior to transfection at a density of 40,000 cells/well. DNAs were transiently transfected using the LipofectAMINE™ reagent (GIBCO; Cat. #18324-012), essentially following the recommended protocol with further optimization for 24-well plates as follows: 200 ng of DNA (representing either a plasmid pool or purified control DNAs) was diluted to 20 µl with Opti-MEM 1 reduced serum media (GIBCO) and diluted into 20 µl of a mixture that consists of 18 µl Opti-MEM 1 and 2 µl of LipofectAMINE™ reagent. This liposome mixture was then incubated for approximately 30 minutes at ambient temperature after which, 200 µl of Opti-MEM 1 was added, and the entire mixture was then overlayed onto a well of CHO/P cells and returned to the incubator. After a 2.5 hour incubation at 37° C., 240 µl of MEM-α (Gibco) media with 20% fetal calf serum (FCS) was added to each well, and the cells were incubated for an additional 18-24 hours at 37° C. The media was then changed to standard MEM-A with 10% FCS, and the adhesion assay was performed approximately 20-24 hours later.

Adhesion Assays for Expression Cloning

For the adhesion assays in the expression cloning screen, the murine T cell lymphoma TK1 which expresses high levels of α4β7 (Butcher, E. C., et al., *Eur. J. Immunol.*, 10: 556-561 (1980)) was used to detect CHO/P cells transfected with cDNAs capable of conferring an adhesive phenotype. TK1 cells were resuspended at a density of $2 \times 10^6$/ml in an assay buffer which consisted of HBSS (Hanks Balanced Salt Solution, without $Ca^{2+}$ or $Mg^{2+}$), supplemented with 2% bovine calf serum, 20 mM HEPES, pH 7.3, 2 mM $Mg^{2+}$, and 2 mM $Ca^{2+}$. Each well transfected with a DNA pool was preincubated with 0.25 ml of a combined supernatant containing monoclonal antibodies to both human VCAM-1 (MAb 2G7; Graber, N. T., et al., *J. Immunol.*, 145:819-830 (1990)) and murine MAdCAM-1 (MAb MECA-367; American Type Culture Collection (Rockville, Md.), Accession No. HB9478; Streeter, P. R., et al., *Nature*, 331:41 (1988)); see also, U.S. Pat. No. 5,403,919 to Butcher) in order to eliminate adhesion mediated by VCAM-1 (which is expressed at high levels in primate lymph nodes) or any potential contaminating murine MAdCAM-1 expression plasmids. After incubation at 4° C. for 15 minutes, 0.25 ml of the TK1 cell suspension ($5 \times 10^5$ TK1 cells) was added to each well, and incubation on a rocking platform was continued for an additional 30 minutes at 4° C. Plates were washed by gently inverting in a large beaker of phosphate buffered saline (PBS) followed by inversion in a beaker of PBS with 1.5% gluteraldehyde for fixation for a minimum of 1 hour. Wells were then examined microscopically (10× objective) for resetting of TK1 cells.

Purification of Macaque Clones

Pools yielding one or more TK1 rosettes were further subfractionated by the following protocol: DNA representative of a positive pool was retransformed into DH10B and plated on ninety-six 100 mm petri dishes at a density of approximately 200 colonies/plate. Nitrocellulose filters were used to generate replica plates, and one set of each plate was then subjected to DNA purification and subsequent adhesion assays as described above. A replica plate representative of a positive pool was then further subfractionated into pools of 5 colonies, which were replica plated and grown overnight in LB media containing ampicillin. After one more round of DNA purification and adhesion assays, individual clones could then be grown up and the clones conferring adhesion of the TK1 cells were identified.

A full-length clone which was shown to encode MAdCAM-1 was obtained and designated clone 31D. Clone 31D, constructed in pSV-SPORT-1 (P25), contains a 5'-SalI to NotI-3' cDNA insert. Transformants of *E. coli* strain DH10B containing clone 31D were obtained. For expression in stable cell lines, this cDNA was subcloned into expression vector pcDNA-3 (Invitrogen), which carries a neo resistance gene suitable for G418 selection. In particular, insert of clone 31D was released by digestion with EcoRI (5') and NotI, and inserted into pcDNA-3 which had been cleaved with EcoRI and NotI to obtain pcD3pMAd.

Results

A cDNA expression library, divided into pools of 1,500 independent clones, was constructed from mRNA purified from macaque mesenteric lymph nodes (MLNs). Each pool was transiently transfected into the CHO/P cell line, and 48 hours after transfection, a cell adhesion assay was performed using the murine T cell lymphoma TK1. As VCAM-1 is expressed in MLNs, assays were done in the presence of anti-VCAM-1 MAb 2G7 (Graber, N. T., et al., *J. Immunol.*, 145:819-830 (1990)). Additionally, assays were performed at 4° C. in order to eliminate adhesion mediated by ICAM cDNAs (TK1 cells express high levels of LFA-1 and LFA-1 is not functional at 4° C.). Microscopic examination of the assays revealed several wells with noticeable rosetting of TK1 cells. Two wells were chosen for further analysis by repeating the transfection and determining whether the binding mediated by the pools could be blocked by anti-β7 or anti-α4 MAbs. TK1 binding to one of the pools was completely inhibited by pre-incubation of TK1 cells with either anti-α4 MAb PS/2 or anti-β7 MAb FIB 504. This pool was subjected to three rounds of subfractionation until a single clone, called 31D, was isolated. Purified clone 31D mediated TK1 cell binding which could be inhibited by anti-α4 or anti-β7 antibodies.

The insert size of clone 31D was approximately 1.8 kb. Sequencing of the amino-terminus revealed several features consistent with a primate equivalent of murine MAdCAM-1. The signal peptides were both 21 amino acids in length. Although the amino acid similarity was found to be only 48%, identity was 71% if non-conservative substitutions were considered. In addition, the protein encoded by clone 31D had a characteristic unique to Ig-family adhesion receptors: two pairs of cysteines separated by 3-4 (3 in this case) amino acids in the first immunoglobulin domain. Finally, 8 amino acids C-terminal to the first double cysteines is a stretch of 9 amino acids that is identical to a sequence in murine MAdCAM-1. Within this region was the sequence LDTSL (SEQ ID NO:14), which aligns with a consensus motif for integrin/Ig family member interactions. Although this motif has general conservation with respect to other Ig adhesion receptors such as ICAM-1, ICAM-2, ICAM-3 and VCAM-1 (Osborn, L., et al., *J. Cell. Biol,* 124:601-608 (1994); Renz, M. E., et al., *J. Cell. Biol.,* 125:1395-1406 (1994)), this exact sequence was previously found only in murine MAdCAM-1. The functional significance of this motif is suggested by the fact that a point mutation which changes the first L (leucine) of the motif at amino acid 61 to an R (arginine) in murine MAdCAM-1 had a dramatic effect on MAdCAM-1: α4β7 binding (not shown). The results of the functional studies together with these sequence characteristics indicate that clone 31D encodes a primate homolog to murine MAdCAM-1.

Screening of a Human Phase Library and Purification of Human Clones

Human phage cDNA libraries were constructed in the λZiPlox™ vector (Gibco/BRL). Human cDNA was made from RNA isolated from either normal or inflamed mesenteric lymph nodes (MLN) as described above. cDNA was synthesized as described above, ligated into the phage vector, and titered on bacterial strain Y1090 (ZL) ("ZL"=Ziplox). Duplicate filters from approximately 500,000 independent clones (50,000 clones/filter) from both the normal and the Crohn's MLN phage libraries were screened with $^{32}$P-labeled full-length macaque MAdCAM-1 cDNA.

To prepare the probe, a ~1.7 kb EcoRI-NotI fragment was excised from clone 31D, and isolated using GeneClean (BIO 101). The fragment was labeled with $\alpha^{32}$P-dCTP by priming with random hexamers (Maniatis et al., In: Molecular Cloning (Cold Spring Harbor Laboratory, Cold Spring Harbor, N.Y., 1990)).

Screening conditions were as follows: 50,000 phage clones were plated on 150 mm petri dishes containing NZYCM agar (Gibco/BRL). After incubation ranging from 7-16 hours, the plates were overlaid with 132 mm nitrocellulose filters (Schleicher and Schuell, Keene, N.H.) for 2 minutes and then five minutes to transfer first and second (duplicate) lifts of phage clones, respectively. Filters were then soaked for 5 minutes in denaturing solution (1.5 M sodium chloride, 0.5 N sodium hydroxide) followed by neutralization in 1.5 M sodium chloride, 0.5 M Tris-HCl, pH 7.5. Filters were air dried for 15 minutes and then baked under vacuum for 2 hours at 80° C.

Filters were pre-hybridized for 2 hours at 55° C. in 2M $Na_2HPO_4$, 0.5% SDS, 5× Denhardt's (1× Denhardt's solution is 0.02% bovine serum albumin, 0.02% ficoll, and 0.02% polyvinyl-pyrolidone), 1 mM EDTA, and 50 µg/ml denatured salmon sperm DNA, and subsequently hybridized overnight at 55° C. in the same buffer. Filters were washed once at room temperature in 2×SSC, 0.1% SDS (1×SSC is 0.15 M sodium chloride, 0.015 M sodium citrate), followed by three to four washes at 65° C. in 0.1×SSC and 0.1% SDS. Filters were monitored with a Geiger counter to see that the background was reduced.

Positive clones were plaque purified, and the plasmid pZL1 containing the cDNA inserts was rescued using the CRE LOX recombination system (GIBCO) (plasmid pZL1 is contained within the body of the lambda Ziplox vector). In particular, a purified phage plaque was suspended in 200 µl of phage buffer (20 mM Tris HCl, pH 7.5, 145 mM NaCl, 8 mM $MgSO_4.7H_2O$, 0.01% gelatin) for 5 minutes at room temperature. 20 µl of the phage suspension was then added to 100 µl of an overnight culture of DH10B (ZL) and incubated for an additional 5 minutes. Dilutions of the mixture were then plated on LB plates supplemented with ampicillin at 50 µg/ml and 10 mM $MgCl_2$, and incubated overnight at 30° C. Single colonies, now containing the cDNA inserted into the pZL1 vector were grown as standard overnight cultures and plasmids were then purified using Qiagen plasmid purification reagents.

Identification of Distinct Functional Human MAdCAM-1 cDNA Clones

Two human cDNA libraries from histologically normal human mesenteric lymph nodes, and inflamed mesenteric lymph nodes from a patient with Crohn's disease were screened using the entire macaque MAdCAM-1 cDNA as a probe. One cross-hybridizing clone was isolated from the normal library, and two cross-hybridizing clones were isolated from the Crohn's library. One of the two clones isolated from the Crohn's library was about 1.3 kb, appeared to be incomplete at the 5'-end, and was not sequenced. The clone from the normal library (clone 4) was slightly larger (1624 bp) than the longer clone (1558 bp) isolated from the Crohn's library (clone 20). Although these two cDNAs differ in size by approximately 100 bp, their 5' and 3' untranslated sequences were almost identical in length. Each clone appeared full-length, as they both contained an amino-terminal signal sequence that was almost identical to the macaque sequence.

Additionally, preliminary sequencing demonstrated the same distinguishing characteristics of the amino-terminal Ig-like domain as the primate cDNA. Since the differences in the size of these clones could not be attributed to the length of the untranslated sequences, it seemed likely that the variation resided in the coding region.

In order to determine whether each clone encoded functional human MAdCAM-1, the inserts of each clone were subcloned into the pCDNA-3 expression vector (Invitrogen), which carries a neo resistance gene suitable for G418 selection. The human cDNAs (which were made using NotI oligo-dT primers at the 3'-end, and SalI adapters at the 5'-end) were ligated into the λZipLox vector, which contains plasmid pZL1. pZL1 vectors with cDNA inserts were rescued as described above. For subcloning, the inserts of clones 4 and 20 were each released by digestion from the PZL1 backbone with EcoRI and NotI. The EcoRI-NotI (5'→3') fragments were isolated by Geneclean (Bio 101) following electrophoresis on a 1% agarose gel, and the fragments were ligated into pcDNA-3 which had been cleaved with EcoRI and NotI. The ligation mixture was used to transform a DH10B E. coli Max efficiency strain (GIBCO), and transformants were obtained following selection on LB agar supplemented with 50 µg/ml ampicillin (Amp). Plasmids designated pcD3huMAd4 (insert from clone 4) and pcD3huMAd20 (insert from clone 20) were obtained and analyzed by restriction digestion.

Figure 5:
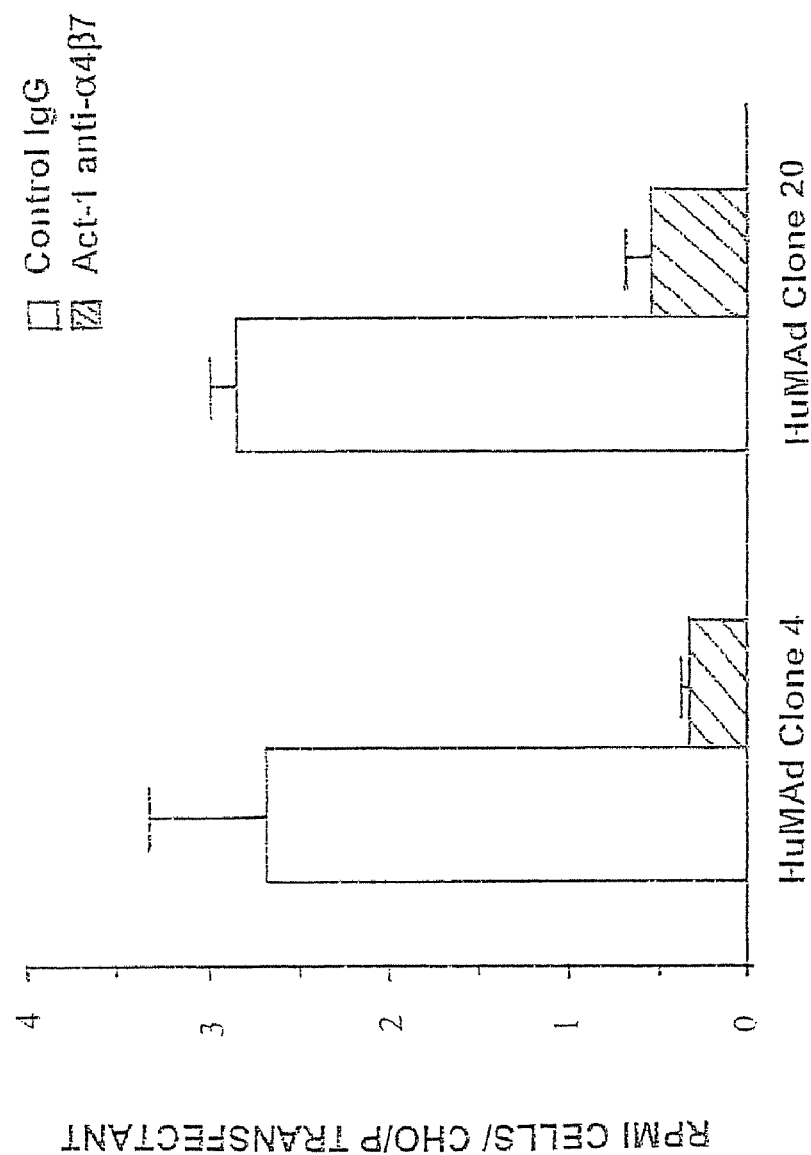
FIG. 5 is a histogram illustrating that human MAdCAM-1 encoded by clones 4 and 20 binds RPMI 8866 cells and that binding is inhibited by the ACT-1 antibody. Bars represent an average of four fields from a single experiment with standard deviations as shown.

Clone pcD3huMAd4 (insert from clone 4) or pcD3huMAd20 (insert from clone 20) was transiently transfected into CHO/P cells. Each clone directed the expression of a functional protein which could mediate binding and adhesion, as assessed by adhesion of CHO/P transfectants to the human B cell lymphoma RPMI 8866 (FIG. 5) or to TK1 cells (not shown).

Adhesion of the CHO/P transfectants to RPMI 8866 cells was blocked by preincubation with anti-α4β7 MAb ACT-1, but not by control IgG. Adhesion of transfectants to TK1 cells was blocked by anti-β7 MAb Fib 504. These results indicate that clone 4 (from a normal mesenteric node library) and clone 20 (from a Crohn's library) each encode functional MAdCAM-1 proteins. To further characterize these distinct cDNAs, both clones were completely sequenced.

Results

The cDNAs from Clones 4 and 20, encoding human MAdCAM-1, are 1628 bp and 1543 bp, respectively, in length. cDNA from Clone 4 (FIG. 1; SEQ ID NO:1) contains an open reading frame of 1218 bp encoding a predicted protein of 406 amino acids (SEQ ID NO:2), and a 3' untranslated region of 410 bp, but contains no 5' untranslated region. cDNA from Clone 20 (FIG. 2; SEQ ID NO:3) contains 4 bp of 5' untranslated sequence, an open reading frame of 1146 bp encoding a predicted protein of 382 amino acids (SEQ ID NO:4), and a 3' untranslated region of 393 bp. The predicted molecular masses of the encoded proteins, after cleavage of a predicted signal sequence of 18 amino acids are 38,375 and 40,910 daltons.

Multiple alignments were performed to analyze the degree of similarity between the different cloned species of MAdCAM-1. Nucleotide alignments revealed 81.9% sequence similarity between mouse and rat MAdCAM-1 cDNAs, 41.8% similarity between mouse and macaque cDNAs, 42.1% similarity between murine and human (Clone 4) MAdCAM-1 cDNAs, and 41.8% similarity between murine and human (Clone 20) MAdCAM-1 cDNAs. Alignment of the nucleotide sequences of macaque MAdCAM-1 with human Clone 4 and Clone 20 cDNAs revealed sequence similarities of 70.7% and 75.0%, respectively.

The amino acid sequence similarities were determined to be 78.5% between mouse and rat MAdCAM-1, 44.3% between mouse and macaque, and 39% between murine and MAdCAM-1 encoded by human Clone 4.

Comparisons of cDNA clones 4 and 20 revealed a region which is homologous to the mucin domain of murine MAdCAM-1, due to a prevalence of serine, threonine and proline (69% for clone 4 and 76% for clone 20) residues (boxed in FIG. 1 and FIG. 2). This region, although similar in amino acid composition to murine MAdCAM-1, is highly divergent from murine MAdCAM-1. The domain is 71 amino acids long in clone 4, and 47 amino acids long in clone 20. This region also contains two polymorphisms: (1) a polymorphism at amino acid 240, which is proline (P) in clone 4 and serine (S) in clone 20; and (2) a polymorphism at amino acid 242, which is asparagine (N) in clone 4 and aspartate (D) in clone 20. In addition, the human mucin domains contain a repeat of 8 amino acids consisting of the sequence PPDTTS(Q/P)E (see e.g., amino acid residues 264-271 and 232-239, respectively, of SEQ ID NOS:1 and 2), which appears eight times in clone 4 and five times in clone 20.

To assess the origin of clones 4 and 20, PCR primers flanking the repeat were used to amplify human genomic DNA. The following primers were used:

```
                              (Primer #1, SEQ ID NO:7)
5'-CTC TAC TGC CAG GCC ACG-3'

(Primer #2, SEQ ID NO:8)
5'-AGC CTG GGA GAT CTC AGG G-3'

(Primer #3, SEQ ID NO:9)
5'-GCC ACG ATG AGG CTG CCT GG-3'

(Primer #4, SEQ ID NO:10)
5'-GTG GAG CCT GGG CTC CTG GG-3'
```

The primers were nested primers. In the first reaction, primers 1 and 2 were used. For the second amplification reaction, a 1:1000 dilution of the first reaction was prepared, and 1 µl was used with primers 3 and 4. Amplification reactions contained either 0.5 µg of genomic DNA, 10 picograms of control plasmids (pcD3HuMAd4 or pcD3HuMAd20), or approximately 1 ng of double-stranded cDNA that was prepared previously for the ZipLox libraries. Genomic DNA was obtained from three sources (Promega; ClonTech, and by purification from Jurkat cells). The conditions of amplification were: one cycle for 5 minutes at 94° C.; 25 cycles at 94° C. for 45 seconds; 60° C. for 45 seconds and 72° C. for one minute followed by one cycle for 5 minutes at 72° C.

The amplification reactions from genomic DNA yielded two bands which comigrated with the individual products of PCR reactions using either clone 4 or clone 20 cDNA as template. This data suggests that the two cDNA clones are isoforms encoded by genomic DNA, and are probably generated by alternative splicing or by transcription of two different alleles. Extensive polymorphism and sequence divergence has been documented in other mucin sequences (e.g., Hilkens, J. et al., *Trends, Biochem. Sci*, 17: 359-363 (1992)). For example, repetitive portions of intestinal mucins are not well-conserved between rodents and humans (Gum, J. G. et al., *J. Biol. Chem.*, 266: 22733-22738 (1991)). One caveat is that, based on an analysis of murine genomic structure, the human genomic DNA could contain an intron in this region. If so, the PCR primers used in this experiment would span the intron, and amplification of human genomic DNA would not be expected to produce bands of the same size as those produced by amplification of the cDNA controls. Isolation and analysis of human MAdCAM-1 genomic clones can conclusively exclude the possibility of a cloning artifact.

The comparison of murine, macaque, and two isoforms of human MAdCAM-1 indicates that the amino-terminal portions of these receptors exhibit domain structures likely to be involved in recognition of α4β7. In contrast, the regions of these receptors in a location corresponding to the location of the mucin/IgA domain of murine MAdCAM-1 display similar amino acid compositions (serine, threonine, proline-rich mucin regions), but are more divergent from one another.

Expression of Human MAdCAM-1 RNA

Northern analysis was carried out using human multiple tissue Northerns I and II (commercially prepared by Clontech), or 2 µg of poly A+ RNA from cell lines and tissues that were prepared as described above. RNA was denatured and electrophoresed through a 1% agarose formaldehyde gel and transferred to a PVDF (Immobilon, Millipore) membrane by standard capillary blot procedures. RNA samples were stained with ethidium bromide to initially ensure that the quality and quantity of each cell or tissue RNA was equivalent. After transfer, RNA was fixed to membranes by UV crosslinking (Stratalinker, Stratagene) and this blot and the commercially prepared blots were pre-hybridized at 68° C. for 1 hour in ExpressHyb (Clontech). The cDNA insert from clone 4 was labeled with $\alpha^{32}$P-dCTP by priming with random hexamers (Maniatis et al., In *Molecular Cloning: A Laboratory Manual*, Cold Spring Harbor Laboratory, Cold Spring Harbor, N.Y., (199)). Hybridization was performed at 68° C. for 1 hour in ExpressHyb with denatured probe at a concentration of $2\times10^6$ cpm/ml.

Blots were then washed in 0.1×SSC, 0.1% SDS for 60 minutes at 65° C. with one change of wash at 30 minutes. The exposure time was 48 hours with an intensifying screen. After this exposure, the blot was stripped by washing for 10 minutes in 0.5% SDS and rehybridized under the same conditions with a β-actin cDNA. The exposure time was 2 hours.

Results

Northern blots were probed for MAdCAM-1 expression using the entire cDNA insert from clone 4 as a probe. A single RNA species of approximately 1.6 kb was highly expressed in the small intestine and was expressed to a lesser extent in the colon and spleen. No significant expression was observed in other tissues examined under these conditions, including thymus, prostate, ovaries, testes and peripheral blood leukocytes (PBL). This tissue-specific pattern of expression is consistent with studies in the mouse showing restricted expression of MAdCAM-1 in Peyer's Patches, MLN (mesenteric lymph node), intestinal lamina propria and some expression in the marginal sinus around splenic white pulp nodules in the spleen (Hemler, M. E., *Annu. Rev. Immunol.*, 8:365 (1990); Berg, E. L., et al., *Cellular and molecular mechanisms of inflammation*, 2:111 (1991); Briskin, M. J., et al., *Nature*, 363:461 (1993)). These data indicate that human MAdCAM-1 expression is tissue-specific with expression in mucosal tissues and spleen; a thorough immunohistochemical analysis of tissue distribution can be performed using monoclonal antibodies against human MAdCAM-1 (see below).

Example 2

Characterization of MAdCAM-1 Clones

Functional Adhesion Assays
Plasmids:
The following plasmids were used in the functional adhesion assays: (1) pSV-SPORT-1 (Gibco/BRL) or pcDNA-3 (Invitrogen) were used as controls; (2) murine MAdCAM-1 in pCDM8 (pCDMAD-7; Briskin, M. J., et al., *Nature*, 363:461 (1993)); (3) seven domain human VCAM-1 (Polte, T., et al., *Nucleic Acids Res.*, 18:5901 (1990)) in pcDNA3 (pCD3VCAM); and (4) human MAdCAM-1 in pcDNA-3 (pCDhuMAd4) (see above).
Monoclonal Antibodies:
The following monoclonal antibodies (MAb) were used in the functional adhesion assays: (1) anti-murine MAdCAM-1 MAb MECA-367 (American Type Culture Collection (Rockville, Md.), Accession No. HB9478; Streeter, P. R., et al., *Nature*, 331:41 (1988); and U.S. Pat. No. 5,403,919 to Butcher); (2) anti-human VCAM-1 MAb 2G7 (American Type Culture Collection (Rockville, Md.); Graber, N. T., et al., *J. Immunol.*, 145:819-830 (1990)); (3) anti-murine $\alpha 4\beta 7$ MAb DATK 32 (Andrew, D. P., et al., *J. Immunol.*, 153:3847-3861 (1994)); (4) anti-murine $\beta 7$ MAb FIB 504; (5) anti-human $\alpha 4\beta 7$ MAb ACT-1 (Lazarovits, A. I., et al., *J. Immunol.*, 133:1857 (1984)); (6) anti-human integrin $\beta 1$ (CD29) (Becton Dickinson; Cat. #550034); and (7) murine IgG1 and rat IgG2A as irrelevant controls.
Cell Lines:
The following cell lines were used in functional adhesion assays:
(1) Murine T cell lymphoma TK1 (Butcher, E. C., et al., *Eur. J. Immunol.*, 10:556-561 (1980); E. Butcher (Stanford, Calif.); (2) RPMI 8866, a human B cell lymphoma line which expresses $\alpha 4\beta 7$ (and not $\alpha 4\beta 1$) (American Type Culture Collection (Rockville, Md.); Erle, D. J., et al., *J. Immunol.*, 153:517 (1994); a gift from D. Erle); (3) JURKAT, a human T cell line which expresses $\alpha 4\beta 1$ (and not $\alpha 4\beta 7$) (American Type Culture Collection (Rockville, Md.)); and (4) Ramos, a human (B lymphocytic) Burkitt lymphoma cell line that expresses $\alpha 4\beta 1$ (and not $\beta 4\beta 7$) (American Type Culture Collection (Rockville, Mass.), Accession No. ATCC CRL 1596).
Functional Adhesion Assays:
For functional adhesion assays, plasmids encoding various species of MAdCAM-1, human VCAM-1, and control plasmids were introduced by transient transfection into CHO/P cells as described above (Example 1) with the following modifications. As several wells were to be transfected for antibody inhibition studies, a master liposome mix with multiples of the wells to be transfected was first made for each plasmid. This ensured that the same liposome mixture was transfected into each well.
48 hours after transfection, the medium was removed. An antibody supernatant (0.25 mls) (containing either anti-human VCAM-1 MAb 2G7 or anti-murine MAdCAM-1 MAb MECA-367), or 0.25 mls of adhesion assay buffer as a control were added, and the mixture was preincubated at 4° C. for 15 minutes.
In parallel, lymphocyte cell lines (RPMI 8866 or Jurkat) were spun down and resuspended at a density of $2\times10^6$/ml in assay buffer consisting of HBSS (without $Ca^{++}$ or $Mg^{++}$) supplemented with 2% bovine calf serum, 20 mM HEPES pH 7.3, 2 mM $Mg^{++}$ and 2 mM $Ca^{++}$. 0.25 ml aliquots ($5\times10^5$ cells) of these RPMI 8866 or JURKAT cell suspensions were preincubated with a small volume of various purified antibodies or with an equal volume of DATK 32 supernatant at 4° C. for 15 minutes. Where DATK 32 was used in a preincubation with a cell line, prior to the start of the assay, the supernatant or buffer present in the wells (containing the transfectants) was aspirated in order to obtain volume of 0.5 ml total for the adhesion assay.
For preincubations, purified antibodies (ACT 1, FIB 504 anti-$\beta 1$) and control IgG antibodies were used at concentrations of 20 µg/ml. 0.25 mls of antibody supernatant (used neat) containing anti-human VCAM-1 (MAb 2G7) or anti-murine MAdCAM-1 (MAb MECA-367) were used in preincubations. 0.25 mls of antibody supernatant of DATK 32 were used in the preincubation.
After the preincubations, cell lines (Jurkat or RPMI 8866) were combined with the transfectants in the wells, and incubation on a rocking platform was continued for an additional 30 minutes at 4° C.
Assays were fixed as described above. Plates were washed by gentle inversion in a large beaker of phosphate buffered saline (PBS), followed by inversion in a beaker of PBS with 1.5% gluteraldehyde for fixation for a minimum of 1 hour. Adhesion was assessed by counting both lymphocytes and CHO cells in a field at 20× magnification. For each assay, the number of lymphocytes bound per CHO/P cell was averaged as a minimum of four fields with standard error. Results in each case are from one of three experiments performed with similar results.

Figure 4B:
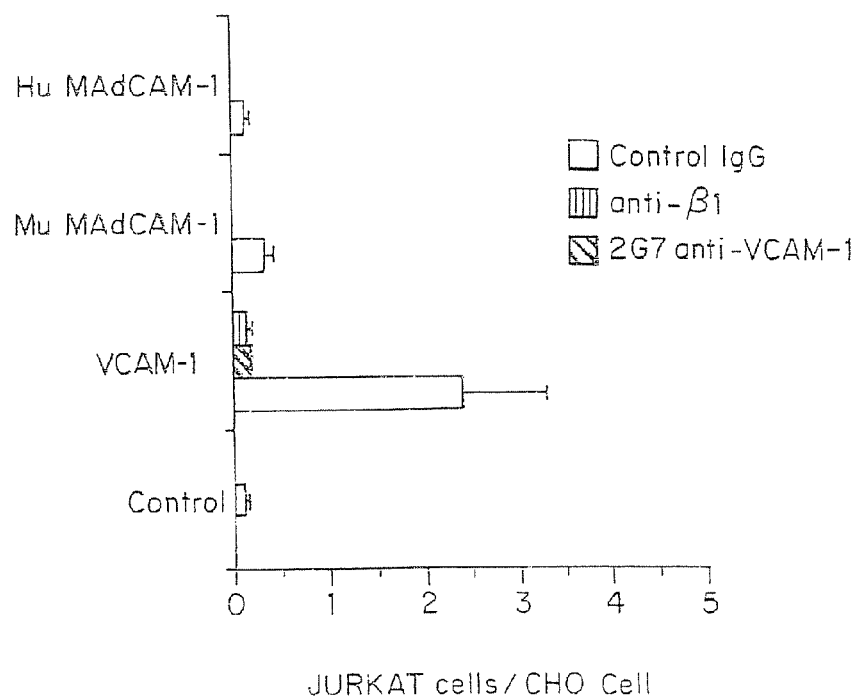

Results
Murine MAdCAM-1 specifically binds lymphocytes expressing $\alpha 4\beta 7$ (and not $\alpha 4\beta 1$). In order to determine the specificity of human MAdCAM-1 lymphocyte interactions, adhesion assays were performed to assess the ability of transiently transfected CHO/P cells expressing human MAdCAM-1 to bind to the RPMI 8866 cell line which only expresses $\alpha 4\beta 7$ (Erle, D. J., et al., *J. Immunol.*, 153:517 (1994)), or to the T cell line Jurkat, which exclusively express $\alpha 4\beta 1$. Binding of these cell lines was compared to that of transiently transfected CHO/P cells expressing murine MAdCAM-1 and human VCAM-1. The results are presented in FIGS. 4A-4B.
RPMI 8866 cells did not bind to control transfectants, but avidly bound to transfectants expressing human or murine MAdCAM-1. This binding was completely inhibited by preincubation with anti-$\alpha 4\beta 7$ MAb ACT-1 (FIG. 4A). VCAM-1 transfectants failed to bind RPMI 8866, which is consistent with the previous demonstration that $\alpha 4\beta 7$/VCAM-1 interactions are activation-dependent (Postigo, A. A., et al., *J. Immunol.*, 151:2471-2483 (1993); Ruegg, C., et al., *J. Cell. Biol.*, 117:179-189 (1992)). The failure of RPMI 8866 cells to bind VCAM-1 was not due to lack of expression, as the same VCAM-1 transfectants were able to bind Jurkat cells, and binding was completely inhibited by preincubation with either anti-VCAM-1 or anti-$\beta 1$ MAbs (FIG. 4B). Murine and human MAdCAM-1 transfectants did not bind Jurkat cells (an $\alpha 4\beta 1$ positive line). These data demonstrate that human MAdCAM-1 can selectively bind to human leukocytes lymphocytes expressing $\alpha 4\beta 7$ integrins.
L1-2 and CHO Cell Transfectants
The mouse L1-2 cell line is derived from a pre-B lymphoma, and was obtained from Dr. Eugene Butcher (Stanford University, Stanford, Calif.). The genes encoding either the macaque or human cDNAs for MAdCAM-1 were subcloned into the pcDNA-3 vector (Invitrogen) as described above. The resulting plasmids (pcD3HuMAd4, pcD3HuMAd20, or pCD3PMad (macaque)) were introduced into L1-2 cells by transfection as follows: L1-2 cells were grown to a density of approximately $10^6$/ml. Either 50, 25 or 12.5 million cells were washed in HBSS and then resuspended in a 0.8 ml of a buffer consisting of Hanks balanced salt solution supplemented with 20 mM HEPES, pH 7.05. A solution consisting of 20 µg of linearized plasmid, 500 µg of tRNA and HBSS to bring the final volume to 200 µl was added to the cell suspension to bring the total volume to 1 ml. After a 10 minute incubation at room temperature the cell/DNA mixture was transferred to an electroporation cuvette (BioRad, Richmond, Calif.) and electroporated at 250 volts, 960 mF in a BioRad gene pulser. Following another 10 minute incubation at room temperature, the cells were diluted to 25 ml in standard L1-2 growth media (RMPI 1640, 10% Hyclone fetal bovine serum, 50 U/ml Penicillin/Styreptomycin (Gibco) and 0.29 mg/ml L Glutamine (Gibco) and returned to the incubator at 37° C. 48 hours later, the cells were pelleted by centrifugation and resuspended in 50 ml of L1-2 media supplemented with G418 (Geneticin; Gibco) at 0.8 mg/ml. Dilutions of the cell suspension were plated in 96-well microtiter plates and single colonies were grown up analyzed for expression of MAdCAM-1.

L1-2 cell clones expressing MAdCAM-1 could be detected by adherence to TK1 cells. L1-2 (non-transfected cells) and TK1 cells both grow as single cell suspensions. Surface expression of MAdCAM-1 can be detected by its ability to mediate adhesion by virtue of its interaction with $\alpha 4\beta 7$ expressed on TK1 cells. Specificity of this interaction was further demonstrated by inhibition by pretreatment of TK1 cells with anti-$\beta 7$ MAb FIB 504.

CHO cells (Chinese Hamster Ovary Cells; American Type Culture Collection (Rockville, Md.)) stably transfected with either the macaque or human MAdCAM-1 clones were prepared by electroporation as described above for the L1-2 cells with the following exceptions. Media for CHO cell growth was $\alpha$-MEM with deoxyribonucleosides (Gibco) and 10% fetal calf serum (Gibco) and 50 U/ml Penicillin/Streptomycin (Gibco) and 0.29 mg/ml L Glutamine (Gibco). Selection media consisted of the same media with 0.55 mg/ml G418 (Gibco). Single clones were grown up and analyzed for their ability to exhibit $\alpha 4\beta 7$-dependent binding of RPMI 8866 cells using the functional adhesion assay described above (for transients), except that cells were plated at 50,000 cells per well in a 24-well plate the day before the assay. Using this criteria, a line called CHO HuMAd 4 was established.

Monoclonal Antibodies Capable of Inhibiting Adhesion

Monoclonal antibodies against human MAdCAM-1 were generated by immunizing C57BL/6 mice with L1-2 MAdCAM-1 transfectants. Mice were immunized intraperitoneally with 10 million cells resuspended in HBSS three times at two week intervals, and a final fourth immunization (of 10 million cells resuspended in HBSS) was injected intravenously. The first immunization was performed with a mixture of two clones (L1-2 cell clone 23 and clone 19) expressing macaque MAdCAM-1. The remaining boosts were done with a single L1-2 clone (L1-2 clone HuMAD4/17) expressing human MAdCAM-1.

A successful fusion was performed which generated approximately 5,000 hybridomas. Four days after the final intravenous injection, the spleen was removed and a single cell suspension was prepared in serum free DMEM media. These cells were fused with the fusion partner SP2/0, according to the method of Galfre et al. (Galfre, G., et al., Nature, 299:550-552 (1977)). 20 ml of spleen cells and 20 ml of SP2/0 cells were combined, spun at 800 g for 5 minutes and the media was removed by aspiration. A solution of 50% polyethylene glycol 1500 (PEG 1500) (Boehringer Mannheim, Indianapolis, Ind.) prewarmed to 37° C. was added to the cell pellet over 2 minutes, followed by 10 ml of DMEM media over 3 minutes. The cell suspension was spun at 600 g for 3 minutes and the supernatant was removed. The pellet was resuspended gently in DMEM media containing 20% fetal calf serum, 2 mM L-glutamine, 100 U/ml penicillin, 100 µg/ml streptomycin sulfate, and HAT selection media (Sigma, St. Louis, Mo.). Cells were plated into ten 96-well flat bottom microtiter plates at 200 µl/well.

Ten days after the fusion, supernatants from the wells were screened for reactivity against CHO human MAdCAM-1 transfectants (CHO HuMAd 4 cells), by fluorescence staining. Staining of 500,000 cells per sample was performed essentially as described, using 50 µl of each supernatant and 50 µl cells (E. Harlow and D. Lane, 1989, In: Antibodies: A Laboratory Manual, Cold Spring Harbor Laboratory, Cold Spring Harbor, N.Y.). The secondary antibody was an FITC-labeled anti-murine IgG (H+L) (Jackson Labs) that was diluted 1:200. Strong reactivity was judged as a 2-3 log increase in fluorescence of as compared with untransfected CHO cells.

48 antibody supernatants were selected for strong reactivity against CHO HuMAd 4 cells. These antibody supernatants were then screened for their ability to block the adhesion of CHO HuMAd 4 cells to RPMI 8866 cells. As a control, the ability of supernatants to inhibit Ramos cell binding to VCAM-1 transfectants was examined, as it should not be affected by a specific anti-human MAdCAM-1 MAb. To identify blocking anti-human MAdCAM-1 monoclonal antibodies, the following assay was performed. To provide control transfectants, CHO/P cells were transfected with pCD3VCAM as described above, and were assayed 48 hours after transfection. 48 hours before the adhesion inhibition assay, 40,000 cells per well of VCAM-1 transient transfectants were plated into 24 well plates. 24 hours before assay, 50,000 cells per well of CHOHuMAd 4 transfectants were plated in 24 well plates. On the day of the assay, each anti-human MAdCAM-1 supernatant (0.25 mls) was added to a well containing either CHOHuMAD 4 transfectants or VCAM-1 transfectants, and the mixture was preincubated at 4° C. for 15 minutes. Adhesion assays were performed, using (1) RPMI 8866 cells with the MAdCAM-1 transfectants or (2) Ramos cells (a human B cell line that expresses $\alpha 4\beta 1$) with the VCAM-1 transfectants.

In parallel, cells (RPMI 8866 or Ramos) were resuspended at a density of $2 \times 10^6$/ml in an assay buffer consisting of HBSS (without Ca$^{++}$ or Mg$^{++}$) supplemented with 2% bovine calf serum, 20 mM HEPES pH 7.3, 2 mM Mg$^{++}$ and 2 mM Ca$^{++}$. After the preincubation of the transfectants with antibody, 0.25 mls of the RPMI 8866 or Ramos cell suspensions ($5 \times 10^5$ cells) were added to each well, and incubation on a rocking platform was continued for an additional 30 minutes at 4° C. The wells were washed, fixed and examined as described above to assess inhibition of binding.

Eleven out of 48 of the hybridoma supernatants examined displayed substantial blocking activity, inhibiting the adhesion of RPMI 8866 cells to transfectants expressing MAdCAM-1. Adhesion of Ramos cells to transfectants expressing VCAM-1 was unaffected, indicating selective inhibition of $\alpha 4\beta 7$-mediated interactions. Selected blocking hybridomas were subcloned by limiting dilution.

Results

Stable cell lines expressing macaque or human MAdCAM-1 were made in the murine pre-B lymphoma L1-2. These cells were used to immunize C57BL/6 mice and prepare hybridomas. The resulting fusion was screened by immunofluorescence staining of CHO HuMAd 4 transfectants expressing human MAdCAM-1. Screening of approximately 1,000 wells produced 48 supernatants exhibiting strong reactivity against the CHO HuMAd 4 transfectants, while non-transfected CHO cells were negative. These supernatants were subsequently tested for their ability to specifically block adhesion of RPMI 8866 cells to human MAdCAM-1 transfectants.

11 of the 48 hybridoma supernatants examined could specifically inhibit the adhesion of RPMI 8866 cells to MAdCAM-1, while adhesion of Ramos cells (which express α4β1) to VCAM-1 transfectants was unaffected by the same supernatants. These hybridomas were designated 10G4, 8C1, 10G3, 9G12, 9E4, 7H12, 10F2, 10A6, 1E5, 2F5, 7G11.

Example 3

Inhibition of Lymphocyte Recruitment to Colon

Induction of Colitis in Mice

BALB/c mice were given access to a 5% solution of dextran sodium sulfate (DSS) in their drinking water for a period of 10 days, as previously described (*Lab. Invest.* 69:238-249, 1993). During this time period, the mice developed clinical symptoms of colitis including softening of stools and bloody diarrhea. Multifocal epithelial injury and ulceration, similar to ulcerative colitis in humans, was evident on histologic examination of colonic mucosa from affected mice. Moreover, affected mice lost 20-30% of their initial body weight by day 10.

Antibody Blockade of β7 and MAdCAM Interactions

To determine the efficacy of β7-specific antibodies in blocking the recruitment of lymphocytes to the colon, BALB/c mice were given daily intraperitoneal (i.p.) injections of 100 µg of monoclonal antibodies against β7, consisting of either FIB21 or FIB30 in saline, as previously characterized and described (Berlin, C., et al., *Cell* 74:185-195, 1993; Michie, S. A., et al., *Am. J. Pathol.* 143:1688-1698, 1993; Hamann, A., et al., *J. Immunol.* 152:3282-3293, 1994) or an isotype-matched control rat monoclonal antibody at the same dose (Andrew et al., supra) over the 10 day course of DSS treatment.

Methods of Evaluation

Two methods were used to evaluate efficacy of the antibody therapy to inhibit leukocyte infiltration and mucosal injury in the colitic mouse. In the first method, treatment was judged histologically by two blinded observers using a scoring system for the evaluation of epithelial injury and degree of leukocyte cellular infiltration (Table 1). For this assessment, colon tissue was first fixed in 10% neutral buffered formalin, dehydrated, embedded in paraffin, sectioned, and the sections were stained with hematoxylin and eosin prior to examination.

TABLE

| PATHOLOGY EVALUATION | | |
|---|---|---|
| Grade | | Definition |
| INFLAMMATION | | |
| Normal | (0) | Absence of clusters of polymorphonoclear leukocytes (PMNs) or mononuclear cells in the lamina propria; absence of intraepithelial PMNs |
| Mild | (1) | Focal aggregates of PMNs and/or mononuclear cells in the lamina propria (equivocal or slight) or presence of isolated intraepithelial PMNs in 3 or fewer crypts per cross-section |
| Moderate | (2) | Focal aggregates of PMNs and/or mononuclear cells in the lamina propria (multi-focal or diffuse 2-5X) or intraepithelial PMNs in more than 3 crypts per cross-section |
| Severe | (3) | Diffuse infiltration of PMNs or mononuclear cells in the lamina propria (diffuse >5X) or crypt abscesses |
| STRUCTURAL OR EPITHELIAL ALTERATIONS | | |
| Normal | (0) | Tight crypts, no erosion, columnar epithelial cells |
| Mild | (1) | Epithelial immaturity; equivocal irregularity of epithelial surface |
| Moderate | (2) | At least two foci of crypt branching or loss of crypts (<50%); loss of surface epithelium |
| Severe | (3) | Diffuse or multifocal branching or loss of crypts (>50%); fibrosis; complete loss of epithelium (focal) |

Additional histologic assessment was performed using immunohistochemistry for the detection and semiquantification of lymphocytes expressing β7 integrins and mucosal venules expressing MAdCAM. As previously described (Ringler, D. J., et al., *Am. J. Pathol.* 134:373-383, 1989), colon tissue was first snap-frozen in OCT compound, sectioned while frozen, and the sections were subsequently fixed in acetone for 10 min at 4° C. After washing in phosphate buffered saline (PBS), nonspecific antibody binding sites were blocked with 10% normal rabbit serum diluted in PBS for 10 min, followed in sequence with washes by FIB21 antibody at 20 µg/ml in PBS for 30 min at room temperature (RT), biotinylated rabbit anti-rat polyclonal antibody, avidin-peroxidase complexes, and finally the chromogen, diaminobenzidine and hydrogen peroxide diluted in Tris buffer.

In the second method, recruitment of lymphocytes to the colon was quantitatively assessed using radiolabeled mesenteric lymph node lymphocytes from syngeneic donor mice. The experimental design of the animal experiments was similar to that described above except that BALB/c mice were placed on 5% DSS for 9 days (instead of 10) and on day 8, mice were given i.p. injections of 100 µg of FIB21 (anti-β7), MECA-367 (anti-MAdCAM), a mixture of both, or an isotype-matched control monoclonal antibody in saline. On day 9, mesenteric lymph node cells were isolated from donor syngeneic BALB/c mice, labeled with $^{51}$Cr, and 5.0×10$^6$ cells/mouse were incubated for 30 minutes at 37° C. with 500 µg control antibody, 250 µg of MECA-367, 500 µg FIB21, or both (total amount is 750 µg) in saline. The labeled cells and antibody were then injected intravenously (i.v.) into the DSS-treated recipient mice. Full-length colons were harvested from all experimental animals 1 hour after injection, and γ-irradiation was measured using a γ-counter.

Data Analysis

Differences between mean scores obtained for each group of animals were assessed for statistical significance using a paired Student's t-test. Differences between means were considered significant when P<0.05.

Results

Histologically, inflammation and epithelial injury to the mucosa were most severe in the descending colon, rectum and cecum. Analysis of frozen tissue sections of colon by immunohistochemistry revealed that the most significant recruitment of $\beta7^+$ lymphocytes was to the right colon. In addition, the level of expression of the mucosal vascular addressin, MAdCAM-1, was found to be expressed only at low levels in vessels in the intestinal mucosa early in DSS treatment (3 days), but increased dramatically after 9 days of DSS treatment, supporting the conclusion that $\beta7$ and MAdCAM-1 interactions are relevant to the inflammatory process in the colonic mucosa during DSS-induced colitis.

Figure 7A:
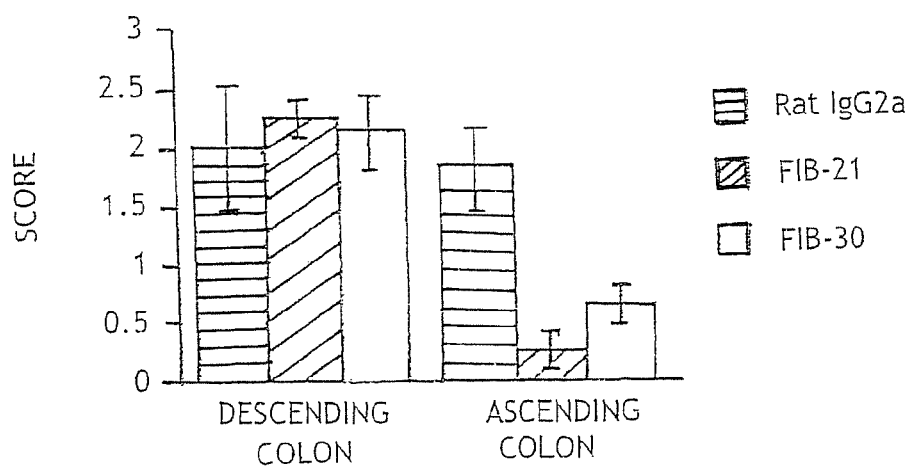
FIGS. 7A and 7B are graphic illustrations of histologic scores of inflammatory activity and epithelial injury from left (descending) and right (ascending) colon of mice exposed to 10 days of DSS in their drinking water. Three groups of mice are shown, consisting of groups receiving an irrelevant rat IgG2a antibody, FIB 21, or FIB 30 antibodies.
Figure 7B:
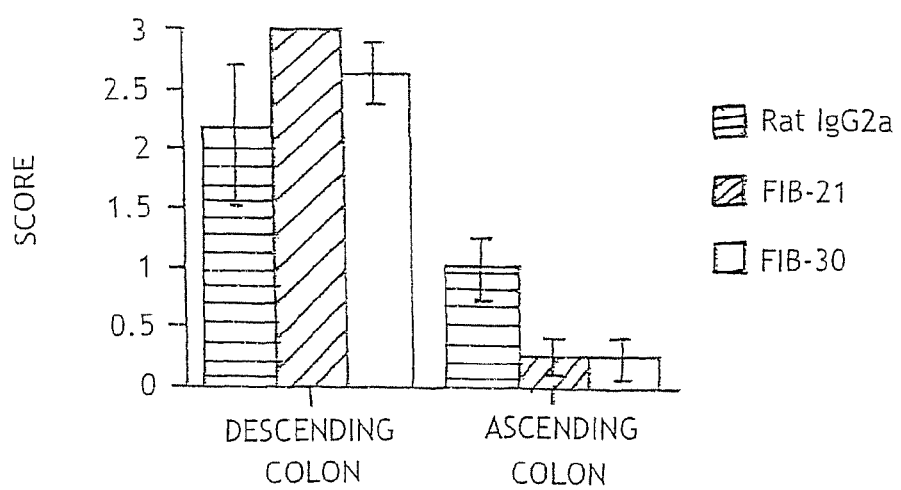

Histologic evaluation of mice exposed to a 10-day course of DSS and daily therapy using $\beta7$-specific antibodies demonstrated that substantial reductions of leukocyte recruitment (P<0.01 for FIB30 and P<0.001 for FIB21) and epithelial injury (P<0.05) occurred in right (ascending) colon compared to animals receiving a control antibody at the same dose (FIGS. 7A and 7B). Furthermore, analysis using immunohistochemistry of frozen sections from these animals suggested that the number of $\beta7^+$ cells recruited to the right colon, but not other sections of colon, during DSS treatment was reduced.

Figure 8:
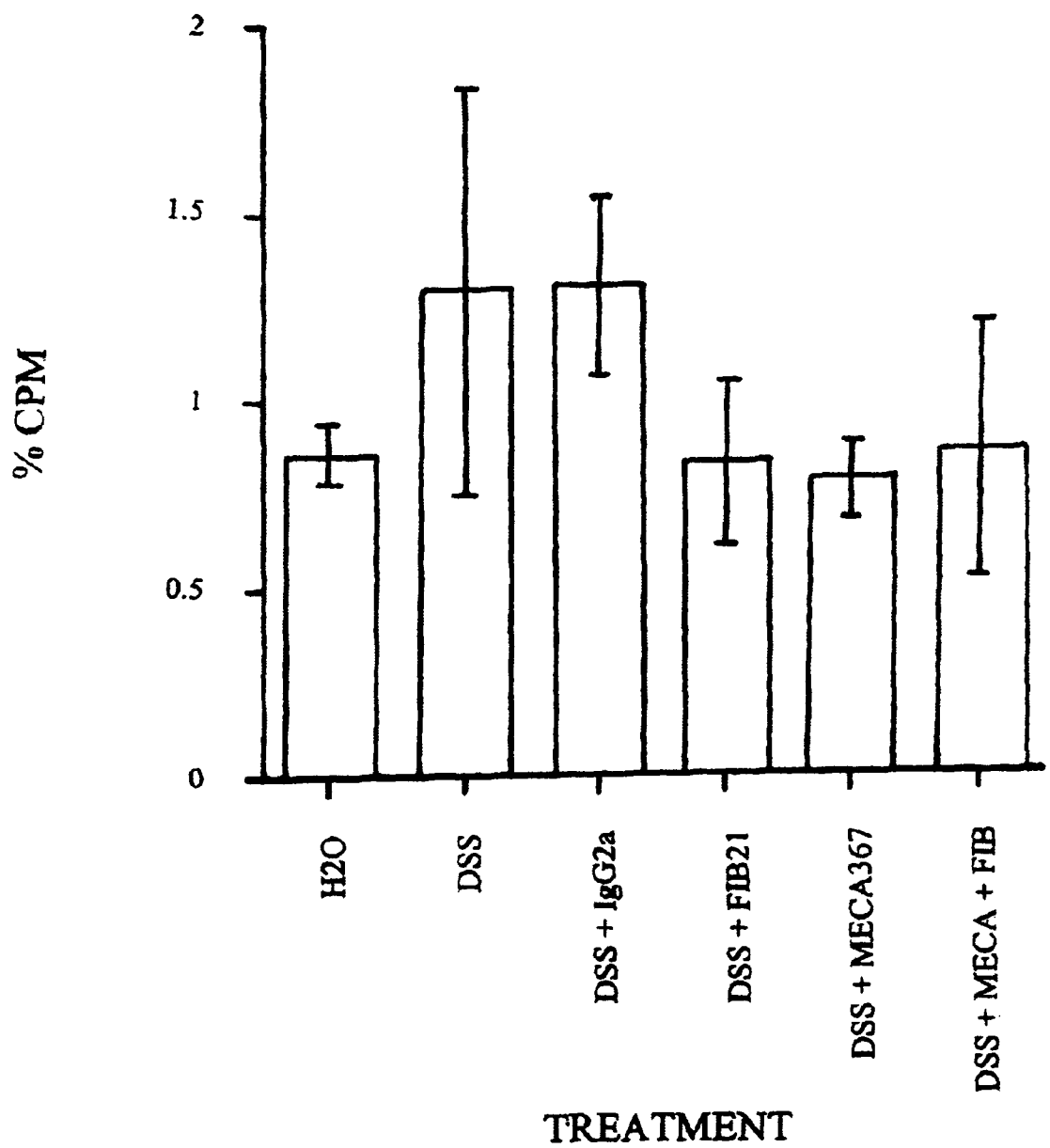
FIG. 8 is a graph of γ counts per minute (cpm) (±1 SEM) as a percentage of input from mice given DSS in the drinking water for 10 days. Six groups consisted of negative controls given water alone, positive controls given DSS alone, test groups given irrelevant rat IgG2a antibody, FIB21, MECA-367, or FIB21 with MECA-367.

Lymphocyte recruitment to inflamed colon was then quantitatively assessed using radiolabeled mesenteric lymphocytes taken from syngeneic donors. One hour after injection of these cells in DSS-treated recipients, there was a trend towards a reduction in the number of $^{51}$Cr-labeled cells recruited to colon in mice that were treated with either $\beta7$-specific antibodies or the MAdCAM-specific antibodies, but not in mice treated with the isotope-matched control antibodies (FIG. 8).

Example 4

Resolution of Villus Alterations in the Common Marmoset (*Callithrix jacchus*) with Malabsorptive Enteritis Description of Model Common marmosets (*Callithrix jacchus*) are a new world nonhuman primate that, under captive conditions at the New England Regional Primate Research Center (NERPRC), develop a steroid-nonresponsive, spontaneous malabsorption syndrome characterized by weight loss, diarrhea, and small intestinal mucosal changes consistent with loss of absorptive capacity. These histologic changes include small intestinal villus atrophy and fusion, and a mononuclear leukocyte infiltrate within the lamina propria similar to Celiac disease (non-tropical sprue) in humans. Retrospective analysis from the pathology archive files at NERPRC demonstrated that up to 80% of common marmosets have, to various degrees, malabsorptive enteritis at the time of postmortem examination.

Antibody Therapy Protocol

Adult common marmosets were selected for study from the colony-at-large at NERPRC. Base-line studies on all animals included physical examination, complete blood count (CBC), blood chemistry profile, serum B12, c-reactive protein, and full-thickness jejunal biopsy by laparotomy. Following recovery from abdominal surgery, the animals were treated for 14 days with 2 mg/kg/day of ACT-1 monoclonal antibody, a blocking monoclonal antibody against a conformational epitope of $\alpha4\beta7$ (Schweighoffer, T., et al., *J. Immunol.* 151: 717-729, 1993). Previous studies indicated that this antibody cross-reacted to Callithrix $\alpha4\beta7$. All assessments that were performed prior to antibody therapy were repeated between the 10th and 14th day of antibody therapy.

Analysis of Jejunal Biopsies

Full-thickness jejunal biopsies from each marmoset were evaluated histologically by two independent pathologists, and villus architecture was scored according to the following grading criteria:

| Villus atrophy | | |
|---|---|---|
| | 0 | normal mucosal thickness and villus height |
| | 1 | mild atrophy; slight shortening of villi; height approximately 75% of normal |
| | 2 | moderate atrophy; villi approximately 33-50% normal height |
| | 3 | severe atrophy; short (<33% normal) or no observable villi |
| Villus fusion | | |
| | 0 | normal; no fusion |
| | 1 | 1-2 villi in specimen fused |
| | 2 | Between 1-2 and 50% of villi in specimen fused |
| | 3 | >50% villi in specimen fused |

Data Analysis

Differences between mean scores obtained for each group of animals were assessed for statistical significance using a paired Student's t-test. Differences between means were considered significant when P<0.05.

Results

Figure 9:
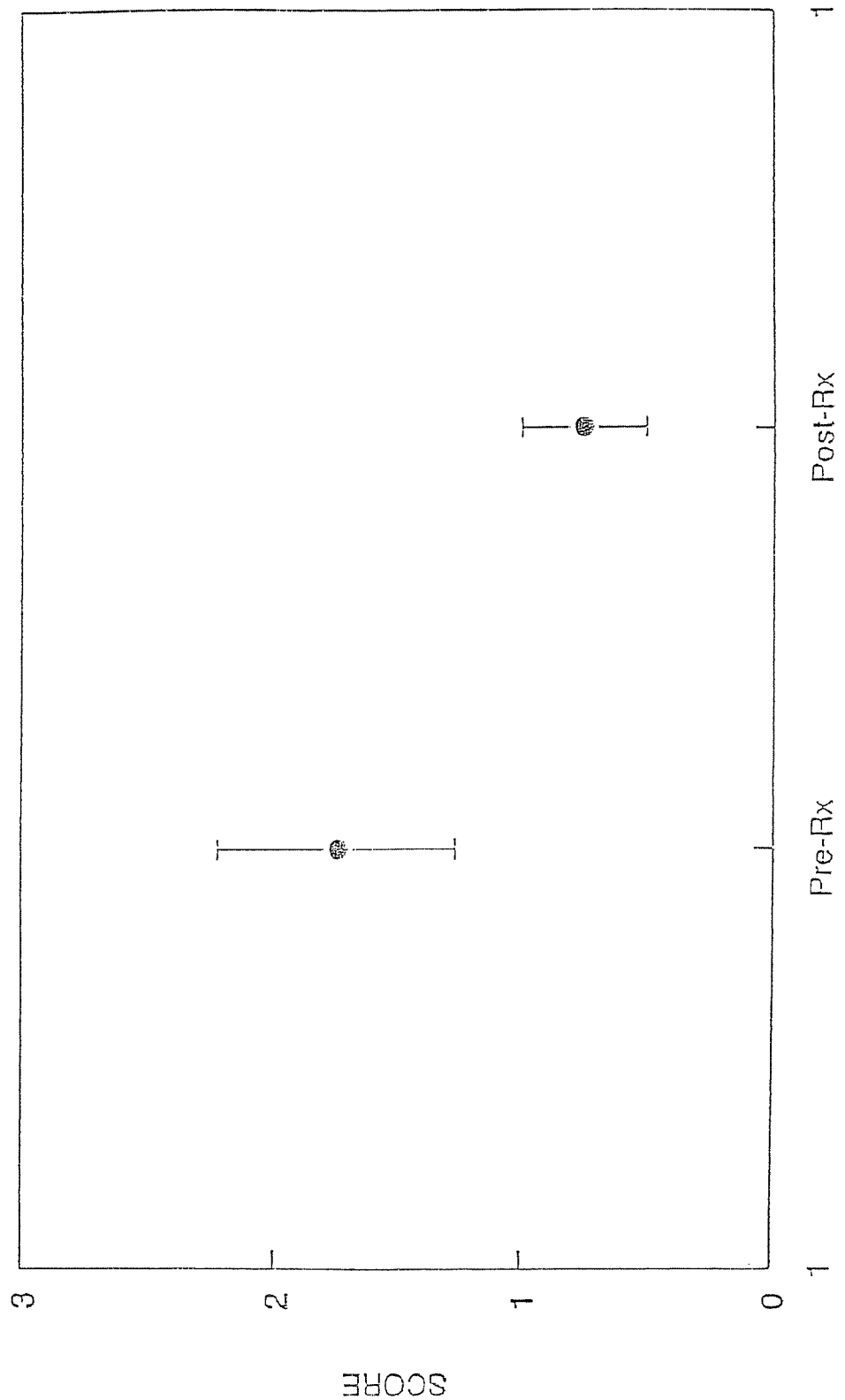
FIG. 9 is a graph depicting the histologic scores (±1 SEM) for villus fusion obtained from jejunal biopsy samples of common marmosets before and on the 14th day of treatment with 2 mg/kg/day of ACT-1 monoclonal antibody.
Figure 10:
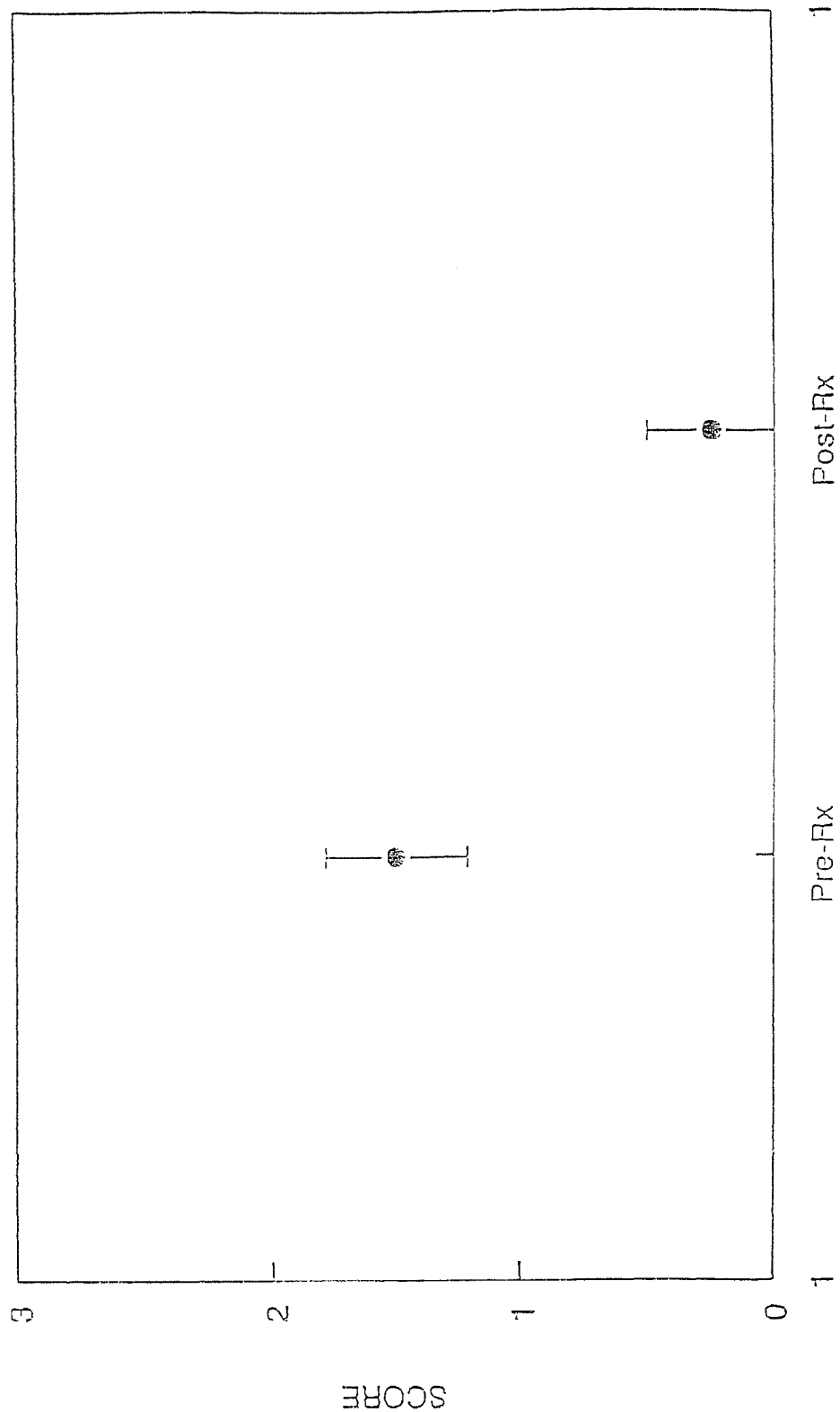
FIG. 10 is a graph depicting the histologic scores (±1 SEM) for villus atrophy obtained from jejunal biopsy samples of common marmosets before and on the 14th day of treatment with 2 mg/kg/day of ACT-1 monoclonal antibody.

The mean scores for villus fusion and atrophy before and after antibody therapy with the ACT-1 monoclonal antibody are shown in FIGS. 9 and 10, respectively. As demonstrated, there was almost complete resolution of villus atrophy (P<0.01) and a trend for improvement of villus fusion after a two-week course of therapy with the ACT-1 antibody. The effect was not secondary to nonspecific effects of exposure to foreign immunoglobulin since other animals treated with various monoclonal antibodies directed against epitopes other than that recognized by ACT-1 were ineffective in reducing villus fusion and atrophy scores.

Example 5

Resolution of Colitis in the Cotton Top Tamarin

Description of Model

The cotton-top tamarin (*Saguinus oedipus*) is a New World nonhuman primate which develops a spontaneous colitis similar to ulcerative colitis in man.

ACT-1 was known to cross-react in the tamarin because of immunohistologic staining with ACT-1 antibody of colitic mucosa from affected animals. These initial pilot studies demonstrated that from 40-80% of mononuclear cells within the lamina propria of colon from affected animals were $\alpha4\beta7+$, similar to human colitic mucosa.

Methods

Colitic animals were chosen from the colony-at-large based upon gross observation of diarrhea and weight loss. All candidate animals were then subjected to colon biopsy to confirm the presence of colitis, as defined as a histologic inflammatory activity score of 2 or 3. The scoring system used was originally described in Madara, J. L. et al., *Gastroenterology* 88:13-19 (1985). Briefly, inflammatory activity scores were based upon the relative numbers of neutrophils within the lamina propria, crypt lumena, crypt epithelium, and surface epithelium. All biopsy samples were scored and categorized into four groups, with 0 representing normal mucosa and 3 representing the most severe and inflamed mucosa. Scores of 0 and 1 do not represent symptomatic colitis, while scores of 2 to 3 represent mild to severe colitic activity. Within 5 days of confirmation of colitis, the animals began immunotherapy with ACT-1 monoclonal antibody.

Four colitic animals received ACT-1 monoclonal antibody at a dose of 2 mg/kg/day intravenously (I.V.) the first day followed by intramuscularly (I.M.) injections for 7 consecutive days thereafter. The dosing regime was the same as that used in the common marmoset study above.

Colon biopsies were again obtained at the time of the first antibody infusion (Day 0) and on days 5, 10 and 20. The biopsies were evaluated by an independent pathologist. Additional colon biopsies were frozen for immunohistology. Animal caretakers evaluated stool consistency on a daily basis by categorizing stool as diarrhea, semi-solid, or solid. Animals were weighed every other day, while blood was drawn at the same intervals for flow cytometry, hematology, and storage of serum or plasma for further analyses, such as antibody concentration, anti-mouse IgG titer, clinical chemistry, or acute phase proteins.

Results/Progress

All four animals maintained either a grade 2 or 3 colitic inflammatory activity in both the pre-treatment and Day 0 biopsy samples, which for 3 animals was separated by 5 days. In addition, changes within the mucosal architecture of all four animals demonstrated that these four animals had colitis of a long-lasting nature. Therefore, all animals appeared to have a chronic disease course.

Figure 11:
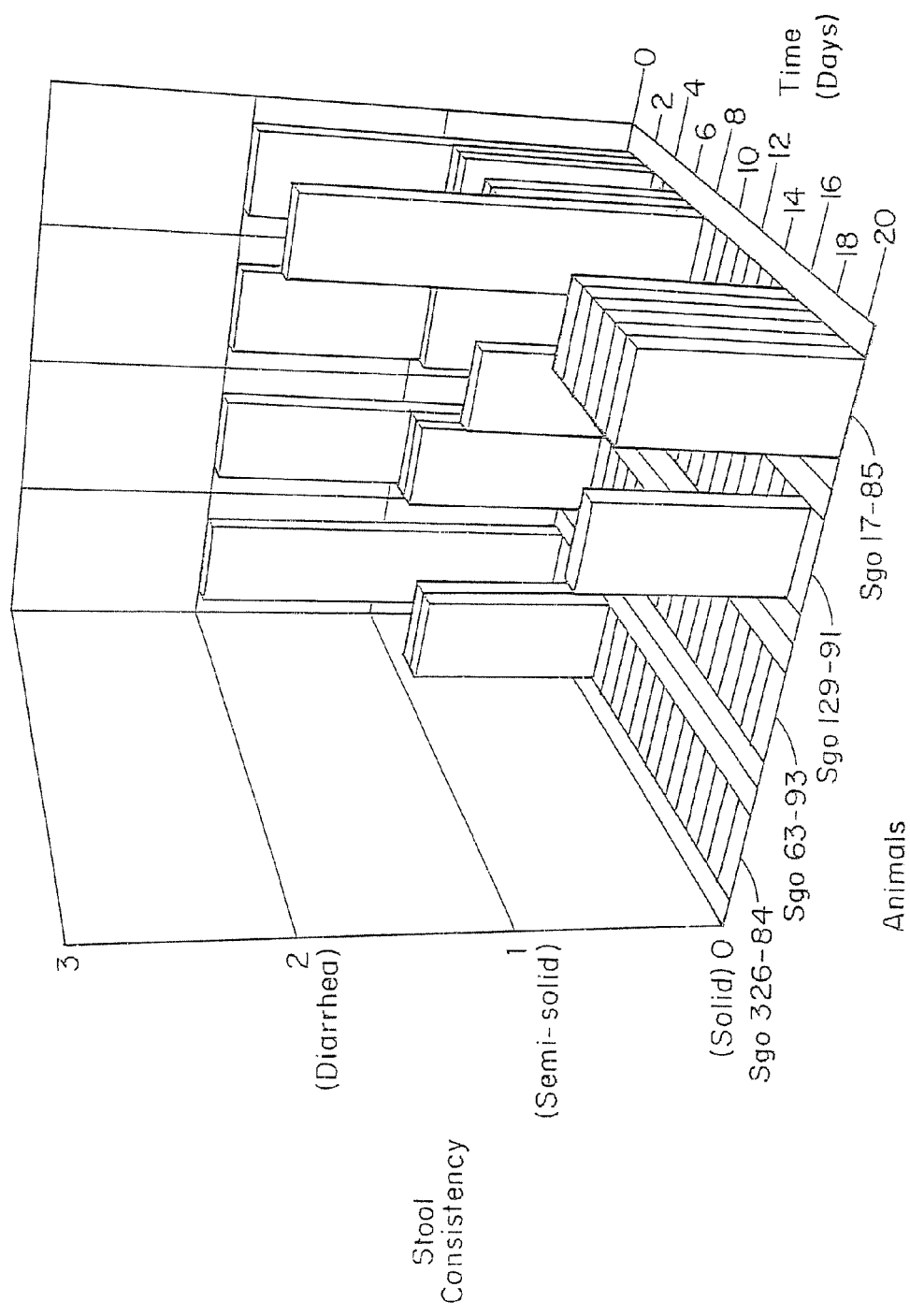
FIGS. 11 and 12 are graphic illustrations of the stool consistency and inflammatory activity in colitic animals (cotton-top tamarins) treated with ACT-1 antibody.

With respect to stool consistency, diarrhea resolved in all four animals by day 8 of ACT-1 immunotherapy (FIG. 11). All animals maintained solid stools for approximately 1 week after termination of antibody injections (FIG. 11). One animal (Sgo 63-93) has had solid stool from Day 4 until the end of the protocol at Day 20 (FIG. 11). Two animals (Sgo 129-91 and Sgo 17-85) had slight relapses to semi-solid stools after Day 14 in the study (FIG. 11). The fourth animal (Sgo 326-84) showed a persistent improvement/resolution of diarrhea from Day 6 to Day 20.

Figure 12:
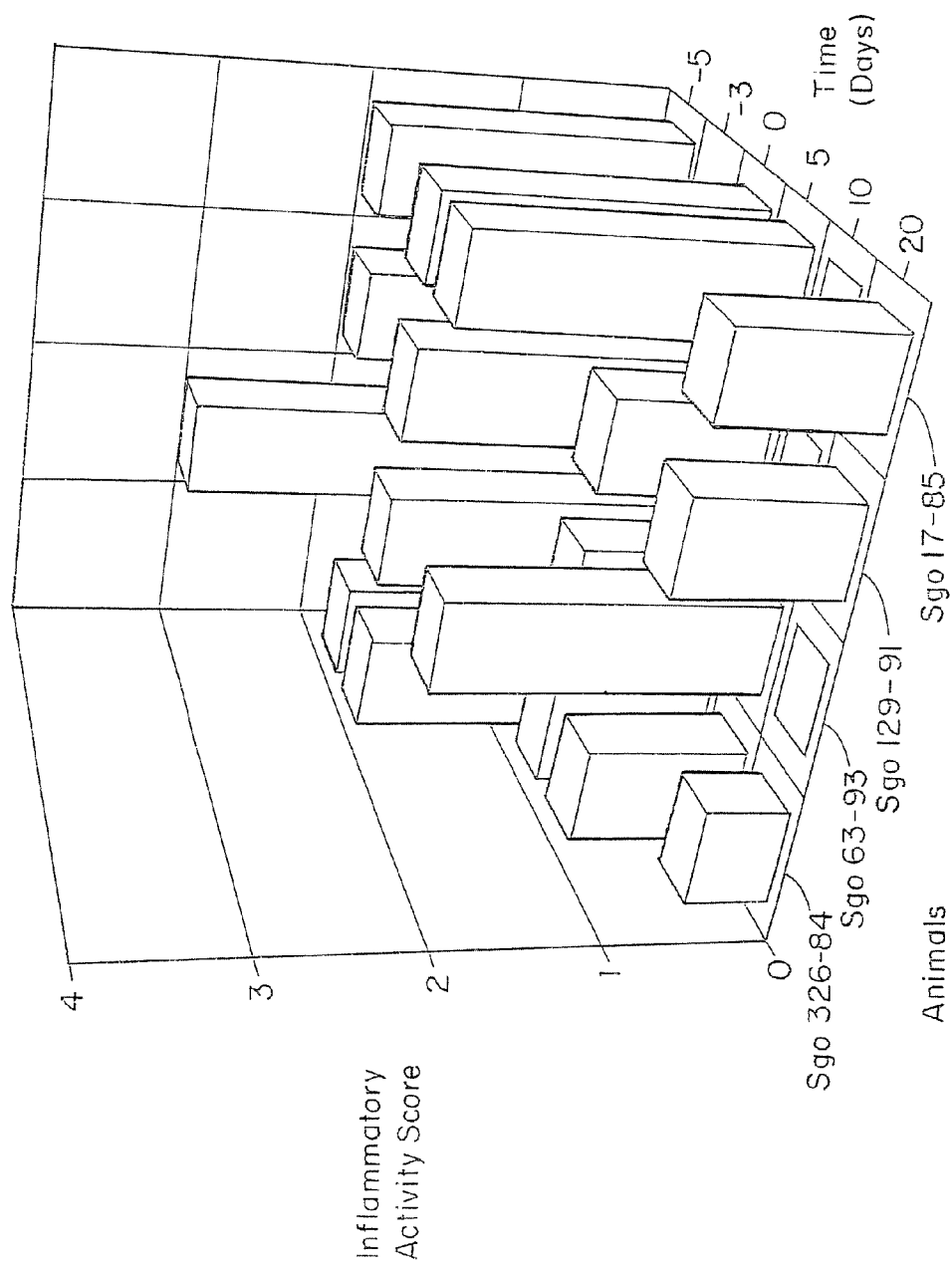

With respect to histologic changes, all four animals have shown improvement in inflammatory activity during or after ACT-1 immunotherapy. The colitis in two animals (Sgo 129-91 and Sgo 17-85) completely resolved by Day 10 (FIG. 12). Another animal (Sgo 63-93) did not show complete abrogation of colitis activity until Day 20 (FIG. 12), while mucosal biopsy scores from the fourth animal (Sgo 326-84) showed improvement during the entire study period (FIG. 12; two biopsies on day 20 in Sgo 326-84 were scored as 0 and 1). Furthermore, animal 326-84 gained 20% of its original body weight during the study period.

To detect antibody administered in vivo, flow cytometry and immunohistology were performed. Flow cytometry without a primary antibody showed excellent labeling to peripheral blood lymphocytes in animals at all time points after antibody administration. Immunohistology on colon biopsies using no primary antibody in the sequence from three animals on samples up to and including Day 10 showed excellent labeling of lymphocytes within the lamina propria on the samples from Days 5 and 10 but not, as expected, from Day 0 prior to antibody infusion. Collectively, these results showed that ACT-1 antibody localized to the target site, namely lymphocytes within the peripheral blood and specifically to the extravascular compartment within colitic mucosa.

SUMMARY

By histologic criteria and stool consistency, ACT-1 was efficacious in improving colitis in the cotton top tamarin.

There appeared to be a good correlation between histologic inflammatory activity scores and stool consistency. Noteworthy is the observation that stool consistency generally improved in 1-2 days in animals receiving ACT-1 antibody.

EQUIVALENTS

Those skilled in the art will be able to recognize, or be able to ascertain, using no more than routine experimentation, many equivalents to the specific embodiments of the invention described herein. Such equivalents are intended to be encompassed by the following claims.

What is claimed is:

1. An isolated nucleic acid which encodes a naturally occurring primate MAdCAM, wherein said nucleic acid encodes the polypeptide shown in FIG. 1 (SEQ ID NO:2), the polypeptide shown in FIG. 2 (SEQ ID NO:4), or the polypeptide shown in FIG. 3 (SEQ ID NO:6).

2. The isolated nucleic acid of claim 1, which is a recombinant nucleic acid.

3. The isolated nucleic acid of claim 1, wherein said nucleic acid is essentially pure.

4. An isolated nucleic acid which encodes a naturally occurring primate MAdCAM, comprising a nucleotide sequence selected from the group consisting of a nucleotide sequence as shown FIG. 1 (SEQ ID NO:1), a nucleotide sequence as shown FIG. 2 (SEQ ID NO:3), a nucleotide sequence as shown FIG. 3 (SEQ ID NO:5), a portion of a nucleotide sequence shown in FIG. 1 (SEQ ID NO:1) comprising the coding sequence, a portion of a nucleotide sequence shown in FIG. 2 (SEQ ID NO:3) comprising the coding sequence and a portion of a nucleotide sequence shown in FIG. 3 (SEQ ID NO:5) comprising the coding sequence.

5. An isolated nucleic acid which encodes a naturally occurring mature primate MAdCAM encoded by any one of SEQ ID NO:1, SEQ ID NO:3 or SEQ ID NO:5.

6. A recombinant nucleic acid construct comprising a nucleic acid which encodes a naturally occurring primate MAdCAM, wherein said nucleic acid encodes a polypeptide having an amino acid sequence as set forth in FIG. 1 (SEQ ID NO:2), FIG. 2 (SEQ ID NO:4), or FIG. 3 (SEQ ID NO:6).

7. The recombinant construct of claim 6, wherein the nucleic acid is operably linked to an expression control sequence.

8. A recombinant nucleic acid construct comprising a recombinant nucleic acid encoding a naturally occurring primate MAdCAM, wherein said nucleic acid has a nucleotide sequence selected from the group consisting of a nucleotide sequence as shown FIG. 1 (SEQ ID NO:1), a nucleotide sequence as shown FIG. 2 (SEQ ID NO:3), a nucleotide sequence as shown FIG. 3 (SEQ ID NO:5), a portion of a nucleotide sequence shown in FIG. 1 (SEQ ID NO: 1) comprising the coding sequence, a portion of a nucleotide sequence shown in FIG. 2 (SEQ ID NO: 3) comprising the coding sequence and a portion of a nucleotide sequence shown in FIG. 3 (SEQ ID NO: 5) comprising the coding sequence.

9. A host cell comprising a recombinant nucleic acid encoding a naturally occurring primate MAdCAM, wherein said nucleic acid encodes the polypeptide shown in FIG. 1 (SEQ ID NO:2), the polypeptide shown in FIG. 2 (SEQ ID NO:4), or the polypeptide shown in FIG. 3 (SEQ ID NO:6).

10. A host cell comprising a recombinant nucleic acid encoding a naturally occurring primate MAdCAM, wherein said nucleic acid comprises a nucleotide sequence selected from the group consisting of a nucleotide sequence as shown FIG. 1 (SEQ ID NO:1), a nucleotide sequence as shown FIG. 2 (SEQ ID NO:3), a nucleotide sequence as shown FIG. 3 (SEQ ID NO:5), a portion of a nucleotide sequence shown in FIG. 1 (SEQ ID NO: 1) comprising the coding sequence, a portion of a nucleotide sequence shown in FIG. 2 (SEQ ID NO: 3) comprising the coding sequence and a portion of a nucleotide sequence shown in FIG. 3 (SEQ ID NO: 5) comprising the coding sequence.

* * * * *

SEQUENCE LISTING

```
(1) GENERAL INFORMATION:

(iii) NUMBER OF SEQUENCES: 14

(2) INFORMATION FOR SEQ ID NO: 1:

(i) SEQUENCE CHARACTERISTICS:
         (A) LENGTH: 1624 base pairs
         (B) TYPE: nucleic acid
         (C) STRANDEDNESS: double
         (D) TOPOLOGY: linear (ii) MOLECULE TYPE: cDNA (ix) FEATURE:
         (A) NAME/KEY: CDS
         (B) LOCATION: 1..1218

(xi) SEQUENCE DESCRIPTION: SEQ ID NO: 1:
```

-continued

```
ATG GAT TTC GGA CTG GCC CTC CTG CTG GCG GGG CTT CTG GGG CTC CTC    48
Met Asp Phe Gly Leu Ala Leu Leu Leu Ala Gly Leu Leu Gly Leu Leu
 1               5                  10                  15

CTC GGC CAG TCC CTC CAG GTG AAG CCC CTG CAG GTG GAG CCC CCG GAG    96
Leu Gly Gln Ser Leu Gln Val Lys Pro Leu Gln Val Glu Pro Pro Glu
                20                  25                  30

CCG GTG GTG GCC GTG GCC TTG GGC GCC TCG CGC CAG CTC ACC TGC CGC   144
Pro Val Val Ala Val Ala Leu Gly Ala Ser Arg Gln Leu Thr Cys Arg
            35                  40                  45

CTG GCC TGC GCG GAC CGC GGG GCC TCG GTG CAG TGG CGG GGC CTG GAC   192
Leu Ala Cys Ala Asp Arg Gly Ala Ser Val Gln Trp Arg Gly Leu Asp
 50                  55                  60

ACC AGC CTG GGC GCG GTG CAG TCG GAC ACG GGC CGC AGC GTC CTC ACC   240
Thr Ser Leu Gly Ala Val Gln Ser Asp Thr Gly Arg Ser Val Leu Thr
 65                  70                  75                  80

GTG CGC AAC GCC TCG CTG TCG GCG GCC GGG ACC CGC GTG TGC GTG GGC   288
Val Arg Asn Ala Ser Leu Ser Ala Ala Gly Thr Arg Val Cys Val Gly
                85                  90                  95

TCC TGC GGG GGC CGC ACC TTC CAG CAC ACC GTG CAG CTC CTT GTG TAC   336
Ser Cys Gly Gly Arg Thr Phe Gln His Thr Val Gln Leu Leu Val Tyr
            100                 105                 110

GCC TTC CCG GAC CAG CTG ACC GTC TCC CCA GCA GCC CTG GTG CCT GGT   384
Ala Phe Pro Asp Gln Leu Thr Val Ser Pro Ala Ala Leu Val Pro Gly
        115                 120                 125

GAC CCG GAG GTG GCC TGT ACG GCC CAC AAA GTC ACG CCC GTG GAC CCC   432
Asp Pro Glu Val Ala Cys Thr Ala His Lys Val Thr Pro Val Asp Pro
    130                 135                 140

AAC GCG CTC TCC TTC TCC CTG CTC GTC GGG GGC CAG GAA CTG GAG GGG   480
Asn Ala Leu Ser Phe Ser Leu Leu Val Gly Gly Gln Glu Leu Glu Gly
145                 150                 155                 160

GCG CAA GCC CTG GGC CCG GAG GTG CAG GAG GAG GAG GAG GAG CCC CAG   528
Ala Gln Ala Leu Gly Pro Glu Val Gln Glu Glu Glu Glu Glu Pro Gln
                165                 170                 175

GGG GAC GAG GAC GTG CTG TTC AGG GTG ACA GAG CGC TGG CGG CTG CCG   576
Gly Asp Glu Asp Val Leu Phe Arg Val Thr Glu Arg Trp Arg Leu Pro
            180                 185                 190

CCC CTG GGG ACC CCT GTC CCG CCC GCC CTC TAC TGC CAG GCC ACG ATG   624
Pro Leu Gly Thr Pro Val Pro Pro Ala Leu Tyr Cys Gln Ala Thr Met
        195                 200                 205

AGG CTG CCT GGC TTG GAG CTC AGC CAC CGC CAG GCC ATC CCC GTC CTG   672
Arg Leu Pro Gly Leu Glu Leu Ser His Arg Gln Ala Ile Pro Val Leu
    210                 215                 220

CAC AGC CCG ACC TCC CCG GAG CCT CCC GAC ACC ACC TCC CCG GAG CCT   720
His Ser Pro Thr Ser Pro Glu Pro Pro Asp Thr Thr Ser Pro Glu Pro
225                 230                 235                 240

CCC AAC ACC ACC TCC CCG GAG TCT CCC GAC ACC ACC TCC CCG GAG TCT   768
Pro Asn Thr Thr Ser Pro Glu Ser Pro Asp Thr Thr Ser Pro Glu Ser
                245                 250                 255

CCC GAC ACC ACC TCC CAG GAG CCT CCC GAC ACC ACC TCC CAG GAG CCT   816
Pro Asp Thr Thr Ser Gln Glu Pro Pro Asp Thr Thr Ser Gln Glu Pro
            260                 265                 270

CCC GAC ACC ACC TCC CAG GAG CCT CCC GAC ACC ACC TCC CCG GAG CCT   864
Pro Asp Thr Thr Ser Gln Glu Pro Pro Asp Thr Thr Ser Pro Glu Pro
        275                 280                 285

CCC GAC AAG ACC TCC CCG GAG CCC GCC CCC CAG CAG GGC TCC ACA CAC   912
Pro Asp Lys Thr Ser Pro Glu Pro Ala Pro Gln Gln Gly Ser Thr His
    290                 295                 300

ACC CCC AGG AGC CCA GGC TCC ACC AGG ACT CGC CGC CCT GAG ATC TCC   960
Thr Pro Arg Ser Pro Gly Ser Thr Arg Thr Arg Arg Pro Glu Ile Ser
```

-continued

| | | | |
|---|---|---|---|
| 305 | 310 | 315 | 320 |

CAG GCT GGG CCC ACG CAG GGA GAA GTG ATC CCA ACA GGC TCG TCC AAA      1008
Gln Ala Gly Pro Thr Gln Gly Glu Val Ile Pro Thr Gly Ser Ser Lys
            325                 330                 335

CCT GCG GGT GAC CAG CTG CCC GCG GCT CTG TGG ACC AGC AGT GCG GTG      1056
Pro Ala Gly Asp Gln Leu Pro Ala Ala Leu Trp Thr Ser Ser Ala Val
        340                 345                 350

CTG GGA CTG CTC CTG GCC TTG CCC ACG TAT CAC CTC TGG AAA CGC          1104
Leu Gly Leu Leu Leu Ala Leu Pro Thr Tyr His Leu Trp Lys Arg
            355                 360                 365

TGC CGG CAC CTG GCT GAG GAC GAC ACC CAC CCA GCT TCT CTG AGG          1152
Cys Arg His Leu Ala Glu Asp Asp Thr His Pro Pro Ala Ser Leu Arg
        370                 375                 380

CTT CTG CCC CAG GTG TCG GCC TGG GCT GGG TTA AGG GGG ACC GGC CAG      1200
Leu Leu Pro Gln Val Ser Ala Trp Ala Gly Leu Arg Gly Thr Gly Gln
385                 390                 395                 400

GTC GGG ATC AGC CCC TCC TGAGTGGCCA GCCTTTCCCC CTGTGAAAGC             1248
Val Gly Ile Ser Pro Ser
            405

AAAATAGCTT GGACCCCTTC AAGTTGAGAA CTGGTCAGGG CAAACCTGCC TCCCATTCTA    1308

CTCAAAGTCA TCCCTCTGCT CACAGAGATG GATGCATGTT CTGATTGCCT CTTTGGAGAA    1368

GCTCATCAGA AACTCAAAAG AAGGCCACTG TTTGTCTCAC CTACCCATGA CCTGAAGCCC    1428

CTCCCTGAGT GGTCCCCACC TTTCTGGACG GAACCACGTA CTTTTTACAT ACATTGATTC    1488

ATGTCTCACG TCTCCCTAAA AATGCGTAAG ACCAAGCTGT GCCCTGACCA CCCTGGGCCC    1548

CTGTCGTCAG GACCTCCTGA GGCTTTGGCA ATAAACCTC CTAAAATGAT AAAAAAAAA     1608

AAAAAAAAAA AAAAA                                                     1624

(2) INFORMATION FOR SEQ ID NO: 2:

(i) SEQUENCE CHARACTERISTICS:
        (A) LENGTH: 406 amino acids
        (B) TYPE: amino acid
        (D) TOPOLOGY: linear (ii) MOLECULE TYPE: protein (xi) SEQUENCE DESCRIPTION: SEQ ID NO: 2:

Met Asp Phe Gly Leu Ala Leu Leu Ala Gly Leu Leu Gly Leu Leu
 1               5                  10                  15

Leu Gly Gln Ser Leu Gln Val Lys Pro Leu Gln Val Glu Pro Glu
                20                  25                  30

Pro Val Val Ala Val Ala Leu Gly Ala Ser Arg Gln Leu Thr Cys Arg
            35                  40                  45

Leu Ala Cys Ala Asp Arg Gly Ala Ser Val Gln Trp Arg Gly Leu Asp
    50                  55                  60

Thr Ser Leu Gly Ala Val Gln Ser Asp Thr Gly Arg Ser Val Leu Thr
65                  70                  75                  80

Val Arg Asn Ala Ser Leu Ser Ala Ala Gly Thr Arg Val Cys Val Gly
                85                  90                  95

Ser Cys Gly Gly Arg Thr Phe Gln His Thr Val Gln Leu Leu Val Tyr
            100                 105                 110

Ala Phe Pro Asp Gln Leu Thr Val Ser Pro Ala Ala Leu Val Pro Gly
        115                 120                 125

Asp Pro Glu Val Ala Cys Thr Ala His Lys Val Thr Pro Val Asp Pro
    130                 135                 140

-continued

```
Asn Ala Leu Ser Phe Ser Leu Leu Val Gly Gly Gln Glu Leu Glu Gly
145                 150                 155                 160

Ala Gln Ala Leu Gly Pro Glu Val Gln Glu Glu Glu Glu Pro Gln
                165                 170                 175

Gly Asp Glu Asp Val Leu Phe Arg Val Thr Glu Arg Trp Arg Leu Pro
            180                 185                 190

Pro Leu Gly Thr Pro Val Pro Pro Ala Leu Tyr Cys Gln Ala Thr Met
        195                 200                 205

Arg Leu Pro Gly Leu Glu Leu Ser His Arg Gln Ala Ile Pro Val Leu
    210                 215                 220

His Ser Pro Thr Ser Pro Glu Pro Pro Asp Thr Thr Ser Pro Glu Pro
225                 230                 235                 240

Pro Asn Thr Thr Ser Pro Glu Ser Pro Asp Thr Thr Ser Pro Glu Ser
                245                 250                 255

Pro Asp Thr Thr Ser Gln Glu Pro Pro Asp Thr Thr Ser Gln Glu Pro
            260                 265                 270

Pro Asp Thr Thr Ser Gln Glu Pro Pro Asp Thr Thr Ser Pro Glu Pro
        275                 280                 285

Pro Asp Lys Thr Ser Pro Glu Pro Ala Pro Gln Gln Gly Ser Thr His
    290                 295                 300

Thr Pro Arg Ser Pro Gly Ser Thr Arg Thr Arg Arg Pro Glu Ile Ser
305                 310                 315                 320

Gln Ala Gly Pro Thr Gln Gly Glu Val Ile Pro Thr Gly Ser Ser Lys
                325                 330                 335

Pro Ala Gly Asp Gln Leu Pro Ala Ala Leu Trp Thr Ser Ser Ala Val
            340                 345                 350

Leu Gly Leu Leu Leu Leu Ala Leu Pro Thr Tyr His Leu Trp Lys Arg
        355                 360                 365

Cys Arg His Leu Ala Glu Asp Asp Thr His Pro Pro Ala Ser Leu Arg
    370                 375                 380

Leu Leu Pro Gln Val Ser Ala Trp Ala Gly Leu Arg Gly Thr Gly Gln
385                 390                 395                 400

Val Gly Ile Ser Pro Ser
                405
```

(2) INFORMATION FOR SEQ ID NO: 3:

(i) SEQUENCE CHARACTERISTICS:
(A) LENGTH: 1539 base pairs
(B) TYPE: nucleic acid
(C) STRANDEDNESS: double
(D) TOPOLOGY: linear (ii) MOLECULE TYPE: cDNA (ix) FEATURE:
(A) NAME/KEY: CDS
(B) LOCATION: 1..1146

(xi) SEQUENCE DESCRIPTION: SEQ ID NO: 3:

```
ATG GAT TTC GGA CTG GCC CTC CTG CTG GCG GGG CTT CTG GGG CTC CTC       48
Met Asp Phe Gly Leu Ala Leu Leu Leu Ala Gly Leu Leu Gly Leu Leu
1               5                   10                  15

CTC GGC CAG TCC CTC CAG GTG AAG CCC CTG CAG GTG GAG CCC CCG GAG       96
Leu Gly Gln Ser Leu Gln Val Lys Pro Leu Gln Val Glu Pro Pro Glu
            20                  25                  30

CCG GTG GTG GCC GTG GCC TTG GGC GCC TCG CGC CAG CTC ACC TGC CGC      144
Pro Val Val Ala Val Ala Leu Gly Ala Ser Arg Gln Leu Thr Cys Arg
        35                  40                  45
```

-continued

| | |
|---|---|
| CTG GCC TGC GCG GAC CGC GGG GCC TCG GTG CAG TGG CGG GGC CTG GAC<br>Leu Ala Cys Ala Asp Arg Gly Ala Ser Val Gln Trp Arg Gly Leu Asp<br>50               55                   60 | 192 |
| ACC AGC CTG GGC GCG GTG CAG TCG GAC ACG GGC CGC AGC GTC CTC ACC<br>Thr Ser Leu Gly Ala Val Gln Ser Asp Thr Gly Arg Ser Val Leu Thr<br>65               70                   75                   80 | 240 |
| GTG CGC AAC GCC TCG CTG TCG GCG GCC GGG ACC CGC GTG TGC GTG GGC<br>Val Arg Asn Ala Ser Leu Ser Ala Ala Gly Thr Arg Val Cys Val Gly<br>85               90                   95 | 288 |
| TCC TGC GGG GGC CGC ACC TTC CAG CAC ACC GTG CAG CTC CTT GTG TAC<br>Ser Cys Gly Gly Arg Thr Phe Gln His Thr Val Gln Leu Leu Val Tyr<br>100             105                 110 | 336 |
| GCC TTC CCG GAC CAG CTG ACC GTC TCC CCA GCA GCC CTG GTG CCT GGT<br>Ala Phe Pro Asp Gln Leu Thr Val Ser Pro Ala Ala Leu Val Pro Gly<br>115             120                 125 | 384 |
| GAC CCG GAG GTG GCC TGT ACG GCC CAC AAA GTC ACG CCC GTG GAC CCC<br>Asp Pro Glu Val Ala Cys Thr Ala His Lys Val Thr Pro Val Asp Pro<br>130             135                 140 | 432 |
| AAC GCG CTC TCC TTC TCC CTG CTC GTC GGG GGC CAG GAA CTG GAG GGG<br>Asn Ala Leu Ser Phe Ser Leu Leu Val Gly Gly Gln Glu Leu Glu Gly<br>145             150               155               160 | 480 |
| GCG CAA GCC CTG GGC CCG GAG GTG CAG GAG GAG GAG GAG CCC CAG<br>Ala Gln Ala Leu Gly Pro Glu Val Gln Glu Glu Glu Glu Pro Gln<br>165             170               175 | 528 |
| GGG GAC GAG GAC GTG CTG TTC AGG GTG ACA GAG CGC TGG CGG CTG CCG<br>Gly Asp Glu Asp Val Leu Phe Arg Val Thr Glu Arg Trp Arg Leu Pro<br>180             185               190 | 576 |
| CCC CTG GGG ACC CCT GTC CCG CCC GCC CTC TAC TGC CAG GCC ACG ATG<br>Pro Leu Gly Thr Pro Val Pro Pro Ala Leu Tyr Cys Gln Ala Thr Met<br>195             200               205 | 624 |
| AGG CTG CCT GGC TTG GAG CTC AGC CAC CGC CAG GCC ATC CCC GTC CTG<br>Arg Leu Pro Gly Leu Glu Leu Ser His Arg Gln Ala Ile Pro Val Leu<br>210             215               220 | 672 |
| CAC AGC CCG ACC TCC CCG GAG CCT CCC GAC ACC ACC TCC CCG GAG TCT<br>His Ser Pro Thr Ser Pro Glu Pro Pro Asp Thr Thr Ser Pro Glu Ser<br>225             230               235               240 | 720 |
| CCC GAC ACC ACC TCC CCG GAG TCT CCC GAC ACC ACC TCC CAG GAG CCT<br>Pro Asp Thr Thr Ser Pro Glu Ser Pro Asp Thr Thr Ser Gln Glu Pro<br>245             250               255 | 768 |
| CCC GAC ACC ACC TCC CCG GAG CCT CCC GAC AAG ACC TCC CCG GAG CCC<br>Pro Asp Thr Thr Ser Pro Glu Pro Pro Asp Lys Thr Ser Pro Glu Pro<br>260             265               270 | 816 |
| GCC CCC CAG CAG GGC TCC ACA CAC ACC CCC AGG AGC CCA GGC TCC ACC<br>Ala Pro Gln Gln Gly Ser Thr His Thr Pro Arg Ser Pro Gly Ser Thr<br>275             280               285 | 864 |
| AGG ACT CGC CGC CCT GAG ATC TCC CAG GCT GGG CCC ACG CAG GGA GAA<br>Arg Thr Arg Arg Pro Glu Ile Ser Gln Ala Gly Pro Thr Gln Gly Glu<br>290             295               300 | 912 |
| GTG ATC CCA ACA GGC TCG TCC AAA CCT GCG GGT GAC CAG CTG CCC GCG<br>Val Ile Pro Thr Gly Ser Ser Lys Pro Ala Gly Asp Gln Leu Pro Ala<br>305             310               315               320 | 960 |
| GCT CTG TGG ACC AGC AGT GCG GTG CTG GGA CTG CTC CTG GCC TTG<br>Ala Leu Trp Thr Ser Ser Ala Val Leu Gly Leu Leu Leu Ala Leu<br>325             330               335 | 1008 |
| CCC ACC TAT CAC CTC TGG AAA CGC TGC CGG CAC CTG GCT GAG GAC GAC<br>Pro Thr Tyr His Leu Trp Lys Arg Cys Arg His Leu Ala Glu Asp Asp<br>340             345               350 | 1056 |
| ACC CAC CCA CCA GCT TCT CTG AGG CTT CTG CCC CAG GTG TCG GCC TGG<br>Thr His Pro Pro Ala Ser Leu Arg Leu Leu Pro Gln Val Ser Ala Trp | 1104 |

-continued

```
                  355                 360                 365
GCT GGG TTA AGG GGG ACC GGC CAG GTC GGG ATC AGC CCC TCC              1146
Ala Gly Leu Arg Gly Thr Gly Gln Val Gly Ile Ser Pro Ser
                  370                 375             380

TGAGTGGCCA GCCTTTCCCC CTGTGAAAGC AAAATAGCTT GGACCCCTTC AAGTTGAGAA   1206

CTGGTCAGGG CAAACCTGCC TCCCATTCTA CTCAAAGTCA TCCCTCTGTT CACAGAGATG   1266

GATGCATGTT CTGATTGCCT CTTTGGAGAA GCTCATCAGA AACTCAAAAG AAGGCCACTG   1326

TTTGTCTCAC CTACCCATGA CCTGAAGCCC CTCCCTGAGT GGTCCCCACC TTTCTGGACG   1386

GAACCACGTA CTTTTTACAT ACATTGATTC ATGTCTCACG TCTCCCTAAA AATGCGTAAG   1446

ACCAAGCTGT GCCCTGACCA CCCTGGGCCC CTGTCGTCAG GACCTCCTGA GGCTTTGGCA   1506

AATAAACCTC CTAAAATGAA AAAAAAAAAA AAA                                1539

(2) INFORMATION FOR SEQ ID NO: 4:

(i) SEQUENCE CHARACTERISTICS:
        (A) LENGTH: 382 amino acids
        (B) TYPE: amino acid
        (D) TOPOLOGY: linear (ii) MOLECULE TYPE: protein (xi) SEQUENCE DESCRIPTION: SEQ ID NO: 4:

Met Asp Phe Gly Leu Ala Leu Leu Ala Gly Leu Leu Gly Leu Leu
  1               5                  10                  15

Leu Gly Gln Ser Leu Gln Val Lys Pro Leu Gln Val Glu Pro Glu
                 20                  25                  30

Pro Val Val Ala Val Ala Leu Gly Ala Ser Arg Gln Leu Thr Cys Arg
                 35                  40                      45

Leu Ala Cys Ala Asp Arg Gly Ala Ser Val Gln Trp Arg Gly Leu Asp
                 50                  55                      60

Thr Ser Leu Gly Ala Val Gln Ser Asp Thr Gly Arg Ser Val Leu Thr
 65                  70                  75                  80

Val Arg Asn Ala Ser Leu Ser Ala Ala Gly Thr Arg Val Cys Val Gly
                 85                  90                      95

Ser Cys Gly Gly Arg Thr Phe Gln His Thr Val Gln Leu Leu Val Tyr
                100                 105                 110

Ala Phe Pro Asp Gln Leu Thr Val Ser Pro Ala Ala Leu Val Pro Gly
                115                 120                 125

Asp Pro Glu Val Ala Cys Thr Ala His Lys Val Thr Pro Val Asp Pro
                130                 135                 140

Asn Ala Leu Ser Phe Ser Leu Leu Val Gly Gly Gln Glu Leu Glu Gly
145                 150                 155                 160

Ala Gln Ala Leu Gly Pro Glu Val Gln Glu Glu Glu Glu Pro Gln
                165                 170                 175

Gly Asp Glu Asp Val Leu Phe Arg Val Thr Glu Arg Trp Arg Leu Pro
                180                 185                 190

Pro Leu Gly Thr Pro Val Pro Pro Ala Leu Tyr Cys Gln Ala Thr Met
                195                 200                 205

Arg Leu Pro Gly Leu Glu Leu Ser His Arg Gln Ala Ile Pro Val Leu
                210                 215                 220

His Ser Pro Thr Ser Pro Glu Pro Asp Thr Thr Ser Pro Glu Ser
225                 230                 235                 240

Pro Asp Thr Thr Ser Pro Glu Ser Pro Asp Thr Thr Ser Gln Glu Pro
                245                 250                 255
```

```
Pro Asp Thr Thr Ser Pro Glu Pro Pro Asp Lys Thr Ser Pro Glu Pro
            260                 265                 270

Ala Pro Gln Gln Gly Ser Thr His Thr Pro Arg Ser Pro Gly Ser Thr
        275                 280                 285

Arg Thr Arg Arg Pro Glu Ile Ser Gln Ala Gly Pro Thr Gln Gly Glu
        290                 295                 300

Val Ile Pro Thr Gly Ser Ser Lys Pro Ala Gly Asp Gln Leu Pro Ala
305                 310                 315                 320

Ala Leu Trp Thr Ser Ser Ala Val Leu Gly Leu Leu Leu Ala Leu
                325                 330                 335

Pro Thr Tyr His Leu Trp Lys Arg Cys Arg His Leu Ala Glu Asp Asp
            340                 345                 350

Thr His Pro Pro Ala Ser Leu Arg Leu Leu Pro Gln Val Ser Ala Trp
        355                 360                 365

Ala Gly Leu Arg Gly Thr Gly Gln Val Gly Ile Ser Pro Ser
        370                 375                 380
```

(2) INFORMATION FOR SEQ ID NO: 5:

(i) SEQUENCE CHARACTERISTICS:
        (A) LENGTH: 1721 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 4..1038

(xi) SEQUENCE DESCRIPTION: SEQ ID NO: 5:

```
AGC ATG GAT CGG GGC CTG GCC CTC CTG CTG GCG GGG CTT CTG GGG CTC      48
    Met Asp Arg Gly Leu Ala Leu Leu Leu Ala Gly Leu Leu Gly Leu
     1               5                  10                  15

CTC CAG CCG GGC TGC GGC CAG TCC CTC CAG GTG AAG CCC CTG CAG GTG      96
Leu Gln Pro Gly Cys Gly Gln Ser Leu Gln Val Lys Pro Leu Gln Val
             20                  25                  30

GAG CCC CCG GAG CCG GTG GTG GCC GTG GCC CTG GGC GCC TCT CGC CAG     144
Glu Pro Pro Glu Pro Val Val Ala Val Ala Leu Gly Ala Ser Arg Gln
         35                  40                  45

CTC ACC TGC CGC CTG GAC TGC GCG GAC CGC GGG GCC ACG GTG CAG TGG     192
Leu Thr Cys Arg Leu Asp Cys Ala Asp Arg Gly Ala Thr Val Gln Trp
     50                  55                  60

CGG GGC CTG GAC ACC AGC CTG GGC GCG GTG CAG TCG GAC GCG GGC CGC     240
Arg Gly Leu Asp Thr Ser Leu Gly Ala Val Gln Ser Asp Ala Gly Arg
 65                  70                  75

AGC GTC CTC ACC GTG CGC AAC GCC TCG CTG TCG GCG GCC GGG ACC CGT     288
Ser Val Leu Thr Val Arg Asn Ala Ser Leu Ser Ala Ala Gly Thr Arg
 80                  85                  90                  95

GTG TGC GTG GGC TCC TGC GGG GGC CGC ACC TTC CAG CAC ACC GTG CGG     336
Val Cys Val Gly Ser Cys Gly Gly Arg Thr Phe Gln His Thr Val Arg
                100                 105                 110

CTC CTT GTG TAC GCC TTC CCG GAC CAG CTG ACC ATC TCC CCG GCA GCC     384
Leu Leu Val Tyr Ala Phe Pro Asp Gln Leu Thr Ile Ser Pro Ala Ala
            115                 120                 125

CTG GTG CCT GGT GAC CCG GAG GTG GCC TGT ACG GCC CAC AAA GTC ACG     432
Leu Val Pro Gly Asp Pro Glu Val Ala Cys Thr Ala His Lys Val Thr
        130                 135                 140

CCT GTG GAC CCC AAT GCG CTC TCC TTC TCC CTG CTC CTG GGG GAC CAG     480
```

```
Pro Val Asp Pro Asn Ala Leu Ser Phe Ser Leu Leu Leu Gly Asp Gln
    145                 150                 155

GAA CTG GAG GGG GCC CAG GCT CTG GGC CCG GAG GTG GAG GAG GAG GAG       528
Glu Leu Glu Gly Ala Gln Ala Leu Gly Pro Glu Val Glu Glu Glu Glu
160                 165                 170                 175

GAG GAG CCC CAG GAG GAG GAG GAC GTG CTG TTC AGG GTG ACA GAG CGC       576
Glu Glu Pro Gln Glu Glu Glu Asp Val Leu Phe Arg Val Thr Glu Arg
                180                 185                 190

TGG CGG CTG CCG ACC CTG GCA ACC CCT GTC CTG CCC GCG CTC TAC TGC       624
Trp Arg Leu Pro Thr Leu Ala Thr Pro Val Leu Pro Ala Leu Tyr Cys
            195                 200                 205

CAG GCC ACG ATG AGG CTG CCT GGC TTG GAG CTC AGC CAC CGC CAG GCC       672
Gln Ala Thr Met Arg Leu Pro Gly Leu Glu Leu Ser His Arg Gln Ala
                210                 215                 220

ATC CCG GTC CTG CAC GGC CCG ACC TCC CGG GAG CCC CCC GAC ACG ACC       720
Ile Pro Val Leu His Gly Pro Thr Ser Arg Glu Pro Pro Asp Thr Thr
        225                 230                 235

TCC CCG GAA CCC CGG GCC GCG ACC TCC CCG GAG ACC ACC CCC CAG CAG       768
Ser Pro Glu Pro Arg Ala Ala Thr Ser Pro Glu Thr Thr Pro Gln Gln
240                 245                 250                 255

GGC TCC ACA CAC AGC CCC AGG AGC CCG GGC TCT ACC AGG ACT TGC CGC       816
Gly Ser Thr His Ser Pro Arg Ser Pro Gly Ser Thr Arg Thr Cys Arg
                260                 265                 270

CCT GAG ATC TCC CAG GCT GGG CCC ACG CAG GGA GAA GTG ATC CCA ACA       864
Pro Glu Ile Ser Gln Ala Gly Pro Thr Gln Gly Glu Val Ile Pro Thr
            275                 280                 285

GGC TCG TCC AAA CCT ACG GGT GAC CAG CTG CCC GCG GCT CTG TGG ACC       912
Gly Ser Ser Lys Pro Thr Gly Asp Gln Leu Pro Ala Ala Leu Trp Thr
        290                 295                 300

AGC AGT GCG GTG CTG GGA CTG CTG CTC CTG GCT TTG CCC ACC TAC CAC       960
Ser Ser Ala Val Leu Gly Leu Leu Leu Leu Ala Leu Pro Thr Tyr His
305                 310                 315

CTC TGG AAA CGT TGC CGG CAC CTG GCT GAG GAC GGC GCC CAC CCA CCA      1008
Leu Trp Lys Arg Cys Arg His Leu Ala Glu Asp Gly Ala His Pro Pro
320                 325                 330                 335

GCT TCT CTG AGT AGC CAG CCC TTC CCC CTG TGAAGGGAAA ATAGGTTGGA        1058
Ala Ser Leu Ser Ser Gln Pro Phe Pro Leu
                340                 345

CCCCTTCAAG CTGAGAACTG GTCGGGGCAA ACCTGCCTCC CATTCTATTC AAAGTCATCG   1118

CTCTGGTCAC AGAGAGGGAC GCACATTCTG ATTGCCTCCT TTGGAAAGGC TCATCAGAAA   1178

CTCAAAAGAA GGTGATCGTT TGTCCCGCCT ACCCGTGACC TGGAAGCCCC CGCCCCGCTC   1238

GAGTGACCCC TGACTTTCTG GACGGAACCA ACGTACTTCT TACATATATT GATTCATGTG   1298

TCATATCTCC CTAAAATGCG TAAAACCAGC TGTGCCCCGA CCACCTTGGG CCCCTGCCAT   1358

CAGGACCTCC TGAGGCTTTG GCAAATAAAC CTCCTAAAAG GATAGAAACT GAAACTTGTG   1418

GCCGGGCGCG GTGGCTCAAG CCTGTAATCC CAGCACTTTG GGAGGCCGAG GTGGGTGGAT   1478

CACGAGGTCA GGAGATCGAG ACCATCCTGG CTAACCCGTG AAACCCCGTC TCTACTAAAA   1538

AAATACAAAA ATTAGCCGGG AGCGGTGGCG GGCGCCTGTA GTCCCAGCTA CTCGGGAGGC   1598

TGAGGCAGGA GAATGGCGTG AACCCGGGAG GCGGAGCTTG CAGTGAGCTG AGATCCGGCC   1658

ACTGCACTCC AGCCTGGGGG ACAGAGCGAG ACTCCGTCTC AAAAAAAAAA AAAAAAAAA   1718

AAA                                                                1721
```

(2) INFORMATION FOR SEQ ID NO: 6:

(i) SEQUENCE CHARACTERISTICS:

(A) LENGTH: 345 amino acids
(B) TYPE: amino acid
(D) TOPOLOGY: linear (ii) MOLECULE TYPE: protein (xi) SEQUENCE DESCRIPTION: SEQ ID NO: 6:

```
Met Asp Arg Gly Leu Ala Leu Leu Ala Gly Leu Gly Leu Leu
 1               5                  10                  15

Gln Pro Gly Cys Gly Gln Ser Leu Gln Val Lys Pro Leu Gln Val Glu
             20                  25                  30

Pro Pro Glu Pro Val Val Ala Val Ala Leu Gly Ala Ser Arg Gln Leu
             35                  40                  45

Thr Cys Arg Leu Asp Cys Ala Asp Arg Gly Ala Thr Val Gln Trp Arg
         50                  55                  60

Gly Leu Asp Thr Ser Leu Gly Ala Val Gln Ser Asp Ala Gly Arg Ser
 65                  70                  75                  80

Val Leu Thr Val Arg Asn Ala Ser Leu Ser Ala Ala Gly Thr Arg Val
                 85                  90                  95

Cys Val Gly Ser Cys Gly Gly Arg Thr Phe Gln His Thr Val Arg Leu
             100                 105                 110

Leu Val Tyr Ala Phe Pro Asp Gln Leu Thr Ile Ser Pro Ala Ala Leu
         115                 120                 125

Val Pro Gly Asp Pro Glu Val Ala Cys Thr Ala His Lys Val Thr Pro
     130                 135                 140

Val Asp Pro Asn Ala Leu Ser Phe Ser Leu Leu Leu Gly Asp Gln Glu
145                 150                 155                 160

Leu Glu Gly Ala Gln Ala Leu Gly Pro Glu Val Glu Glu Glu Glu
                165                 170                 175

Glu Pro Gln Glu Glu Asp Val Leu Phe Arg Val Thr Glu Arg Trp
             180                 185                 190

Arg Leu Pro Thr Leu Ala Thr Pro Val Leu Pro Ala Leu Tyr Cys Gln
         195                 200                 205

Ala Thr Met Arg Leu Pro Gly Leu Glu Leu Ser His Arg Gln Ala Ile
     210                 215                 220

Pro Val Leu His Gly Pro Thr Ser Arg Glu Pro Pro Asp Thr Thr Ser
225                 230                 235                 240

Pro Glu Pro Arg Ala Ala Thr Ser Pro Glu Thr Thr Pro Gln Gln Gly
                245                 250                 255

Ser Thr His Ser Pro Arg Ser Pro Gly Ser Thr Arg Thr Cys Arg Pro
             260                 265                 270

Glu Ile Ser Gln Ala Gly Pro Thr Gln Gly Glu Val Ile Pro Thr Gly
         275                 280                 285

Ser Ser Lys Pro Thr Gly Asp Gln Leu Pro Ala Ala Leu Trp Thr Ser
     290                 295                 300

Ser Ala Val Leu Gly Leu Leu Leu Ala Leu Pro Thr Tyr His Leu
305                 310                 315                 320

Trp Lys Arg Cys Arg His Leu Ala Glu Asp Gly Ala His Pro Pro Ala
                325                 330                 335

Ser Leu Ser Ser Gln Pro Phe Pro Leu
             340                 345
```

(2) INFORMATION FOR SEQ ID NO: 7:

(i) SEQUENCE CHARACTERISTICS:
(A) LENGTH: 18 base pairs (B) TYPE: nucleic acid
        (C) STRANDEDNESS: single
        (D) TOPOLOGY: unknown (xi) SEQUENCE DESCRIPTION: SEQ ID NO: 7:

CTCTACTGCC AGGCCACG                                                             18

(2) INFORMATION FOR SEQ ID NO: 8:

(i) SEQUENCE CHARACTERISTICS:
        (A) LENGTH: 19 base pairs
        (B) TYPE: nucleic acid
        (C) STRANDEDNESS: single
        (D) TOPOLOGY: unknown (xi) SEQUENCE DESCRIPTION: SEQ ID NO: 8:

AGCCTGGGAG ATCTCAGGG                                                            19

(2) INFORMATION FOR SEQ ID NO: 9:

(i) SEQUENCE CHARACTERISTICS:
        (A) LENGTH: 20 base pairs
        (B) TYPE: nucleic acid
        (C) STRANDEDNESS: single
        (D) TOPOLOGY: unknown (xi) SEQUENCE DESCRIPTION: SEQ ID NO: 9:

GCCACGATGA GGCTGCCTGG                                                           20

(2) INFORMATION FOR SEQ ID NO: 10:

(i) SEQUENCE CHARACTERISTICS:
        (A) LENGTH: 20 base pairs
        (B) TYPE: nucleic acid
        (C) STRANDEDNESS: single
        (D) TOPOLOGY: unknown (xi) SEQUENCE DESCRIPTION: SEQ ID NO: 10:

GTGGAGCCTG GGCTCCTGGG                                                           20

(2) INFORMATION FOR SEQ ID NO: 11:

(i) SEQUENCE CHARACTERISTICS:
        (A) LENGTH: 6 amino acids
        (B) TYPE: amino acid
        (C) STRANDEDNESS: <Unknown>
        (D) TOPOLOGY: linear (xi) SEQUENCE DESCRIPTION: SEQ ID NO: 11:

Gly Leu Asp Thr Ser Leu
1               5

(2) INFORMATION FOR SEQ ID NO: 12:

(i) SEQUENCE CHARACTERISTICS:
        (A) LENGTH: 6 amino acids
        (B) TYPE: amino acid
        (C) STRANDEDNESS: <Unknown>
        (D) TOPOLOGY: linear (ix) FEATURE:
        (A) NAME/KEY: Region
        (B) LOCATION: 2
        (D) OTHER INFORMATION: /product= "OTHER"
            /label= variable
            /note= "Xaa = Ile or Leu"

(ix) FEATURE:
        (A) NAME/KEY: Region

```
            (B) LOCATION: 3
            (D) OTHER INFORMATION: /product= "OTHER"
                /label= variable
                /note= "Xaa = Asp or Glu"

(ix) FEATURE:
            (A) NAME/KEY: Region
            (B) LOCATION: 4
            (D) OTHER INFORMATION: /product= "OTHER"
                /label= variable
                /note= "Xaa = Thr or Ser"

(ix) FEATURE:
            (A) NAME/KEY: Region
            (B) LOCATION: 5
            (D) OTHER INFORMATION: /product= "OTHER"
                /label= variable
                /note= "Xaa = Pro or Ser"

(xi) SEQUENCE DESCRIPTION: SEQ ID NO: 12:

Gly Xaa Xaa Xaa Xaa Leu
1               5

(2) INFORMATION FOR SEQ ID NO: 13:

(i) SEQUENCE CHARACTERISTICS:
            (A) LENGTH: 6 amino acids
            (B) TYPE: amino acid
            (C) STRANDEDNESS: <Unknown>
            (D) TOPOLOGY: linear (xi) SEQUENCE DESCRIPTION: SEQ ID NO: 13:

Gln Ile Asp Ser Pro Leu
1               5

(2) INFORMATION FOR SEQ ID NO: 14:

(i) SEQUENCE CHARACTERISTICS:
            (A) LENGTH: 5 amino acids
            (B) TYPE: amino acid
            (C) STRANDEDNESS: <Unknown>
            (D) TOPOLOGY: linear (xi) SEQUENCE DESCRIPTION: SEQ ID NO: 14:

Leu Asp Thr Ser Leu
1               5
```